US009856508B2

(12) United States Patent
Juo et al.

(10) Patent No.: US 9,856,508 B2
(45) Date of Patent: Jan. 2, 2018

(54) CHEMILUMINESCENT COMPOSITIONS, METHODS, ASSAYS AND KITS FOR OXIDATIVE ENZYMES

(71) Applicant: LIFE TECHNOLOGIES CORPORATION, Carlsbad, CA (US)

(72) Inventors: Rouh-Rong Juo, Allston, MA (US); Brooks Edwards, Cambridge, MA (US); Melissa Gee, Bedford, MA (US); Zhixian Wang, Bedford, MA (US); Kathleen Skaare, W. Newton, MA (US)

(73) Assignee: LIFE TECHNOLOGIES CORPORATION, Carlsbad, CA (US)

( * ) Notice: Subject to any disclaimer, the term of this patent is extended or adjusted under 35 U.S.C. 154(b) by 0 days.

(21) Appl. No.: 15/345,098

(22) Filed: Nov. 7, 2016

(65) Prior Publication Data

US 2017/0137862 A1    May 18, 2017

Related U.S. Application Data

(60) Division of application No. 14/694,758, filed on Apr. 23, 2015, now Pat. No. 9,518,285, which is a continuation of application No. 13/254,154, filed as application No. PCT/US2010/025791 on Mar. 1, 2010, now Pat. No. 9,067,910.

(51) Int. Cl.
*C12Q 1/26* (2006.01)

(52) U.S. Cl.
CPC ..... *C12Q 1/26* (2013.01); *G01N 2333/90251* (2013.01)

(58) Field of Classification Search
CPC ........................................................ C12C 1/26
USPC ........................................................ 549/330
See application file for complete search history.

(56) References Cited

U.S. PATENT DOCUMENTS

| 4,931,223 | A | 6/1990 | Bronstein |
| 4,931,569 | A | 6/1990 | Edwards et al. |
| 4,952,707 | A | 8/1990 | Edwards et al. |
| 4,956,477 | A | 9/1990 | Bronstein et al. |
| 4,978,614 | A | 12/1990 | Bronstein et al. |
| 5,112,960 | A | 5/1992 | Bronstein et al. |
| 5,145,772 | A | 9/1992 | Voyta et al. |
| 5,220,005 | A | 6/1993 | Bronstein et al. |
| 5,225,584 | A | 7/1993 | Brooks et al. |
| 5,326,882 | A | 7/1994 | Bronstein et al. |
| 5,330,900 | A | 7/1994 | Bronstein et al. |
| 5,336,596 | A | 8/1994 | Bronstein et al. |
| 5,543,295 | A | 8/1996 | Bronstein et al. |
| 5,547,836 | A | 8/1996 | Bronstein et al. |
| 5,578,253 | A | 11/1996 | Schaap et al. |
| 5,582,980 | A | 12/1996 | Bronstein et al. |
| 5,795,987 | A | 8/1998 | Schaap et al. |
| 5,936,101 | A | 8/1999 | Akhavan-Tafti et al. |
| 5,994,073 | A | 11/1999 | Bronstein et al. |
| 6,124,478 | A | 9/2000 | Bronstein et al. |
| 6,140,495 | A | 10/2000 | Bronstein et al. |
| 6,355,441 | B1 | 3/2002 | Edwards et al. |
| 7,053,208 | B2 | 5/2006 | Bronstein et al. |
| 7,214,546 | B2 | 5/2007 | Sparks |
| 7,416,898 | B2 | 8/2008 | Giri |
| 9,067,910 | B2 | 6/2015 | Juo et al. |
| 9,518,285 | B2 | 12/2016 | Juo et al. |
| 2007/0112061 | A1 | 5/2007 | Kimura et al. |
| 2015/0084766 | A1 | 10/2015 | Cordaro et al. |

FOREIGN PATENT DOCUMENTS

| EP | 0671395 | 9/1995 |
| WO | 1996015122 | 5/1996 |
| WO | 2006073424 | 7/2006 |
| WO | 2006129036 | 12/2006 |

(Continued)

OTHER PUBLICATIONS

Caplus, A., "Abstract of ITE Letters on Batteries" New Technologies & Medicine, vol. 5, 2004, pp. 581-584.
Ciscato, L., et al. "Sythesis and studies of fenchyl-derived 1,2-diotetanes", CA Accession No. 148:10784, 2007, 1.
FDA "Draft Guidance for Industry: Drug Interaction Studies-Study Design, Data Analysis, and Implications for Dosing and Labeling", http://www.fda.gov/cder/biologics/qa.hotm.
Kimura, M et al., "Relationship between heat of reaction and chemiluminescence efficiency of chemiluminescent reactions", CA Accession No. 144: 311603, 2005, 1.

(Continued)

*Primary Examiner* — Taofiq A Solola

(57) ABSTRACT

Chemiluminescent compositions, methods, assays and kits for oxidative enzymes are described. Further disclosed are dioxetane compounds of the form:

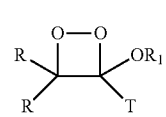

(I)

where R can independently be any branched alkyl or cycloalkyl group which provides stabilization for the dioxetane or where both R groups together form a cycloalkyl or polycycloalkyl moiety spiro bound to the dioxetane ring, wherein each R group or the spiro bound moiety can be unsubstituted or substituted with one or more electron-withdrawing groups or electron donating groups, or groups providing preferential oxidative isozyme substrate recognition, and wherein $R_1$ is an aryl group, or an alkyl group of 1-20 carbon atoms, which can be optionally substituted with 1 or more halogen atoms, and wherein T is an aryl or heteroaryl ring capable of emitting light upon enzyme activated decomposition of the dioxetane I.
Kits, methods and assays are also disclosed that comprise the dioxetane compounds.

23 Claims, 16 Drawing Sheets

(56) References Cited

FOREIGN PATENT DOCUMENTS

WO    2010101839    10/2010

OTHER PUBLICATIONS

Matsumoto, M. et al., "Synthesis of 3-ethoxy-4,4-diisopropyl-1,2-dioxetanes bearing a Benzo(b)furan-2-yl or a benzo(b)thiophen-2-yl group: CIEEL-active dioxetanes emitting red light", Luminescence, 14, 1999, 345-348.

Matsumoto, M. et al., "Effect of Allylic Oxygen on the Reaction Pathways of Singlet Oxygenation: Selective Formation of 1,2-Dioxetanes from . . . ", Tetrahedron Letters, vol. 37, No. 3, 1996, 397-400.

Paradise, E. et al., "Cytochrome P450 Inhibition Assays Using Traditional and Fluorescent Substrates", Current Protocols in Pharmacology, 2007, 12 pgs.

Richard, et al., "Self-cleavable chemiluminescent probes suitable for protease sensing", Org. Biomol. Chem 7(14), 2009, 2941-2957.

Richard, J. et al., "Chemiluminescent Probe for the in Vitro Detection of Protease Activity", Organic Letters, vol. 9, No. 23, 2007, pp. 4853-4855.

Watanabe, Nobuko et al., "Electron-Transfer-Induced Chemiluminescent Decomposition of Dioxetanes Bearing a 3-Hydroxyphenyl Substituted with a Podand-type Group", ITE Letters on Batteries, New Technologies & Medicine, vol. 5, No. 6, 2004, 581-584.

Watanabe, Nobuko et al., "Synthesis of 3-Alkoxy-3-aryl-4,4-diisopropyl-1,2-dioxetanes and their Base-Induced Chemiluminescence", Tetrahedron, 55, 1999, 4287-4298.

Wu, J. et al., "High-Throughput Cytochrome P450 Inhibition Assays Using Laser Diode Thermal Desorption-Atmospheric Pressure Chemical Ionization-Tandem Mass Spectrometry", Analytical Chemistry, 2007, 4657-4665.

Yao, M. et al., "Development and full validation of six inhibition assays for five major cytochrome P450 enzymes in human liver microsomes using an automated 96-well microplate incubation format and LC—MS/MS analysis", Journal of Pharmaceutical and Biomedical Analysis, vol. 44, 2007, pp. 211-223.

AMPPD-Bn 1

CDP-*Star*-Me 2

CDP-*Star*-Et 3

CDP-*Star*-Bn 4

Cl-BZT-Me 5

Cl-BZT-EOM 6

BZT-Me 7

EG-Ad-Cl-Ph-OEOM 8

EG-Ad-Ph-OMe 9

EG-Ad-Ph-OBn 10 bis-CO$_2$Me-Ad-Ph-OEOM 11

Q$^+$-Amino-Ad-Ph-OEt 12

Q$^+$-Amino-Ad-Ph-OEOM 13 bis-CO$_2$Na-Ad-Ph-OEt 14 bis-CO$_2$Na-Ad-Ph-OEOM 15

| Isozyme | Isozyme Conc. final | Substrate | $K_m$ range ($\mu M$) | Substrate Conc. final | Time (@25°C) | Typical S/B |
|---|---|---|---|---|---|---|
| CYP3A4 | 5nM | AMPPD-Bn | 1.05-2.7 | 2μM | 10 min | 853 |
| CYP2C19 | 5nM | BZT-Me | 1.54-8.4 | 1μM | 10 min | 19000 |
| CYP2C9 | 10nM | BZT-Me | 1.2-1.48 | 2μM | 12 min | 50 |
| CYP2D6 | 10nM | Cl-BZT-EOM | 2.39-11.2 | 5μM | 15 min | 108 |
| CYP1A2 | 5nM | Cl-BZT-Me | N/A | 1.25μM | 10 min | 250 |

TABLE 1
Isoenzyme Specificity of Cytochrome P450 substrates

| Substrate | Compound Number | Aqueous Solubility | Primary Isozyme Specificity | | Secondary Isozyme Specificity | |
|---|---|---|---|---|---|---|
| | | | Isozyme | S/B | Isozyme | S/B |
| AMPPD-Bn | 1 | limited | 3A | 2,240 | 2C19 | 1,750 |
| BZT-Me | 7 | limited | 2C19 | 29,500 | 2C18 | 1,800 |
| Cl-BZT-EOM | 6 | limited | 3A5 | 3,040 | 2C19 | 2,400 |
| Cl-BZT-Me | 5 | limited | 2C19 | 9,900 | 2C18 | 3,000 |
| CDP-Star-Me | 2 | limited | 2C19 | 4,340 | 3A4 | 610 |
| CDP-Star-Et | 3 | limited | 2C19 | 3,200 | 3A4 | 400 |
| CDP-Star-Bn | 4 | limited | 3A | 2,400 | 2C19 | 680 |
| EG-Ad-Cl-Ph-OEOM | 8 | good | 3A | 4,080 | 2C19 | 240 |
| EG-Ad-Ph-OBn | 10 | good | 3A | 270 | 3A7 | 12 |
| bis-CO₂Me-Ad-Ph-OEOM | 11 | good | 3A | 1,250 | 2C8 | 200 |
| Q+-Amino-Ad-Ph-OEt | 12 | good | 3A | 280 | 2D6 | 4 |
| Q+-Amino-Ad-Ph-OEOM | 13 | good | 3A | 490 | 2D6 | 12 |
| EG-Ad-Ph-OMe | 9 | good | 2C19 | 1400 | 3A4 | 200 |
| bis-CO₂Na-Ad-Ph-OEt | 14 | good | 2C8 | 475 | 3A7 | 21 |
| bis-CO₂Na-Ad-Ph-OEOM | 15 | good | 2C8 | 860 | 3A7 | 40 |

*Assays performed using same conditions (25° C, 5 nM rhCyp, 10 μM substrate, 25 min endpoint assay, with isozyme-specific buffers, Luminoscan plate reader), but on different days.

TABLE 2
Comparison of CYP3A4 Substrates

| Substrate | 3A4 | | 3A5 | | Nxt Highest Activity | | |
|---|---|---|---|---|---|---|---|
| | ~RLU | S/B | RLU | S/B | Isozyme | RLU | S/B |
| EG-Ad-Cl-Ph-OEOM | 23,600 | 4,080 | 7,400 | 1,300 | 2C19 | 1,400 | 240 |
| EG-Ad-Ph-OBn | 11,300 | 270 | 1,300 | 30 | 3A7 | 500 | 12 |
| bis-CO$_2$Me-Ad-Ph-OEOM | 9,250 | 1,250 | 3,300 | 450 | 2C8 | 1,450 | 200 |
| Q+-Amino-Ad-Ph-OEt | 1,300 | 280 | 500 | 104 | 2D6 | 20 | 4 |
| Q+-Amino-Ad-Ph-OEOM | 2,000 | 490 | 670 | 170 | 2D6 | 50 | 12 |
| AMPPD-Bn | 7,400 | 2,240 | 925 | 280 | 2C19 | 5,800 | 1,750 |
| Cl-BZT-EOM | 4,700 | 590 | 24,000 | 3,040 | 2C19 | 18,600 | 2,400 |
| CDP-Star-Bn | 9,660 | 2,400 | 9,110 | 2,300 | 2C19 | 2,700 | 680 |

*Assays performed using same conditions (25° C, 5 nM rhCyp, 10 μM substrate, 25 min endpoint assay, with isozyme-specific buffers, Luminoscan plate reader), but on different days.

FIG. 16

CHEMILUMINESCENT COMPOSITIONS, METHODS, ASSAYS AND KITS FOR OXIDATIVE ENZYMES

CROSS-REFERENCE TO RELATED APPLICATIONS

This application is a divisional application of U.S. patent application Ser. No. 14/694,758 filed Apr. 23, 2015, which is a continuation application of U.S. patent application Ser. No. 13/254,154, filed Nov. 11, 2011 (now U.S. Pat. No. 9,067,910), which is a national stage filing of International Application No. PCT/US2010/025791, filed Mar. 1, 2010, which claims priority to U.S. Provisional Application No. 61/156,836, filed Mar. 2, 2009; which disclosures are hereby incorporated by reference in their entirety.

The section headings used herein are for organizational purposes only and should not be construed as limiting the subject matter described herein in any way.

BACKGROUND

Cytochrome P450 (CYP450) enzymes are responsible for breakdown of most of the current drugs on the market. Consequently, each new molecular entity or drug candidate must endure rigorous toxicity testing in preclinical trials that includes testing for potential drug-drug interactions as a result of CYP450 inhibition or activation. As a result, there has been increasing demand for easy to use and more efficacious compositions, methods, kits and assays that are amenable to high throughput screening to monitor CYP450 enzyme inhibition and activation.

OBJECTS OF THE EMBODIMENTS

It is an object of the embodiments to provide more user-friendly, more sensitive and more efficacious bioassays for oxidative enzymes in which enzymatically cleavable 1,2-dioxetanes are used as reporter molecules.

It is also an object of the embodiments to provide new and improved enzymatically cleavable chemiluminescent 1,2-dioxetanes for use as substrates for oxidative enzyme-based assays, which provide improved signal to background behavior, improved detection levels, and improved isozyme specificity in biologically relevant assays.

A further object of the embodiments is the provision of dioxetanes whose emission wavelengths are shifted toward the green wavelengths.

Another object of the embodiments is to provide novel intermediates useful in synthesizing these improved enzymatically cleavable 1,2-dioxetanes, and methods of preparing these intermediates and chemiluminescent 1,2-dioxetanes thereof.

SUMMARY

A dioxetane is provided as described by the formula:

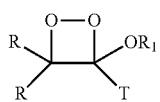

(I)

where R can independently be any branched alkyl or cycloalkyl group which provides stabilization for the dioxetane or where both R groups together form a cycloalkyl or polycycloalkyl moiety spiro bound to the dioxetane ring, wherein each R group or the spiro bound moiety can be unsubstituted or substituted with one or more electron-withdrawing groups, or electron donating groups, or groups providing preferential oxidative isozyme substrate recognition, and wherein $R_1$ is an aryl group, or an alkyl group of 1-20 carbon atoms, which can be optionally substituted with 1 or more halogen atoms, and wherein T is an aryl or heteroaryl ring capable of emitting light upon enzyme activated decomposition of the dioxetane (I).

Novel intermediates and methods of synthesis are provided for synthesizing the various dioxetane substrates.

Assays are provided for the detection of the presence of various enzymes in an aqueous sample, comprising adding to the sample a dioxetane of compound (I).

Assays are also provided for detecting changes in enzyme activity (e.g., inhibition, activation, and the like.) in an aqueous sample, comprising adding to the sample a dioxetane of compound (I).

Kits are provided that comprise the above described dioxetane compound (I).

Kits are also provided that comprise the dioxetane compound (I) and assays.

These and other features of the present teachings are set forth herein.

BRIEF DESCRIPTION OF THE DRAWINGS

The skilled artisan will understand that the drawings, described below, are for illustration purposes only. The drawings are not intended to limit the scope of the present teachings in any way.

FIG. 2A shows AMPPD-Bn 1; FIG. 2B shows CDP-Star-Me 2.

FIG. 3A is a graphic representation of isozyme specificity of EG-AD-Cl-Ph-OEOM in rhCYP microsomes. Assays were performed at 25° C. for 25 min using 10 µM EG-Ad-Cl-Ph-OEOM, 5 nM rhCYP450, and isozyme-preferred potassium phosphate buffer, pH 7.4. This substrate shows a strong specificity for CYP3A4/5 isozymes. FIG. 3B is a graphic representation of isozyme specificity of EG-AD-Cl-Ph-OEOM in pooled human liver microsomes (HLMs). Assays were performed for 10 min at 25° C. using 2 µM EG-Ad-Cl-Ph-OEOM and 100 mM potassium phosphate buffer, pH 7.4. Positive (3A4) and negative (2C19, 2D6, and microsome only) controls were performed using 5 nM rhCYP450 microsomes. Pooled HLMs were assayed at 0.5, 0.25, 0.125, or 0.0625 mg/ml. Assays were performed either with or without 2 µM ketoconazole to show CYP3A family specificity. All assays were performed using the 2-step assay method (Example 48, Format A).

FIG. 4A is a graphic representation of isozyme specificity of AMPPD-Bn in rhCYP microsomes. Assays were performed at 25° C. for 25 min using 10 μM AMPPD-Bn, 5 nM rhCYP450 and isozyme-preferred potassium phosphate buffer, pH 7.4. AMPPD-Bn shows a strong specificity for CYP3A4 and CYP2C19 isozymes. FIG. 4B is a graphic representation of isozyme specificity of AMPPD-Bn in pooled human liver microsomes (HLMs). Assays were performed for 25 min at 25° C. using 20 μM AMPPD-Bn and 100 mM potassium phosphate buffer, pH 7.4. Positive (3A4) and negative (2C19, 2D6 and microsome only) controls were performed using 5 nM rhCYP450 microsomes. Pooled HLMs were assayed at 0.5, 0.25, 0.125, or 0.0625 mg/ml. Assays were performed either with or without 2 μM ketoconazole to indicate CYP3A family specificity. CYP2C19 activity does not significantly contribute to AMPPD-Bn oxidation in HLMs due to the large excess of CYP3A4 present relative to CYP2C19. All assays were performed using the 2-step assay method (Example 48, Format A).

FIG. 5A is a graphic representation of isozyme specificity of BZT-Me in rhCYP microsomes. Assays were performed ate 25° C. for 25 min using 10 μM BZT-Me, 5 nM rhCYP450, and isozyme-preferred potassium phosphate buffer, pH 7.4. BZT-Me shows a strong specificity for the CYP2C19 isozyme, but is also oxidized by other CYP isozyme. FIG. 5B is a graphic representation of isozyme specificity of BZT-Me in pooled human liver microsomes (HLMs). Assays were performed for 25 min at 25° C. using 20 μM BZT-Me and 50 mM potassium phosphate buffer, pH 7.4. Positive (2C19) and negative (3A4, 2D6, and microsome only) controls were performed using 5 nM rhCYP450 microsomes. Pooled HLMs or low 2C19 HLMs were assayed at 0.5, 0.25, 0.125, or 0.0625 mg/ml. Assays were performed with or without 2 μM ketoconazole to indicate CYP3A family specificity or 0.5 μM miconozole. All assays were performed using the 2-step assay method (Example 48, Format A).

FIG. 6A and FIG. 6B show CYP450 inhibition assay conditions using recombinant enzyme and the $IC_{50}$ curves for CYPs 3A4, 2C19, 2C9, 2D6, and 1A2, using recombinant enzyme. FIG. 6A shows inhibition assay conditions derived for CYPs 3A4, 2C19, 2C9, 2D6, and 1A2 using rhCYP microsomes. Assays are performed using the 2-step assay format (Example 48). FIG. 6B shows IC50 determination of known inhibitors of CYPs 3A4, 2C19, 2D6, and 1A2 using the above inhibition assay conditions. *As published in Yao et al., Journal of Pharmaceutical and Biochemical Analysis, 2007. As published in Wu et al., Analytical Chemistry, 2007. *As published in Paradise et al., Current Protocols in Pharmacology, 2007.

FIG. 7A is a graphic representation of the AMPPD-Bn 3A4 assay. The assay was performed at 25° C. for 10 min using 0.1 mg/ml pooled HLMs (Cellzdirect), 2 μM AMPPD, 100 mM Potassium Phosphate Buffer, pH 7.4 and 1:3 dilutions of ketoconazole. The assay was performed using the 2-step assay format (Example 48). FIG. 7B shows the IC50 determination of ketoconazole for CYP3A in Human Liver Microsomes which was performed using an un-optimized assay protocol. The assay was performed at 25° C. for 10 min using 0.1 mg/ml pooled HLMs (Cellzdirect), 2 μM EG-AD-Cl-Ph-OEOM, 100 mM Potassium Phosphate Buffer pH 7.4, and 1:3 dilutions of ketoconazole. The assay was performed using the 2-step assay format (Example 48).

FIG. 15 shows Table 1 "Isozyme Specificity of Cytochrome P450 Substrates". Assays were performed using the same conditions (25° C., 5 nM rhCyp, 10 μM substrate, 25 min endpoint assay, with isozyme-specific buffers, Luminoscan plate reader) but on different days.

FIG. 16 shows Table 2 "Comparison of CYP3A4 Substrates". Assays were performed using the same conditions (25° C., 5 nM rhCyp, 10 μM substrate, 25 min endpoint assay, with isozyme-specific buffers, Luminoscan plate reader) but on different days.

DESCRIPTION OF VARIOUS EMBODIMENTS

Figure 1:
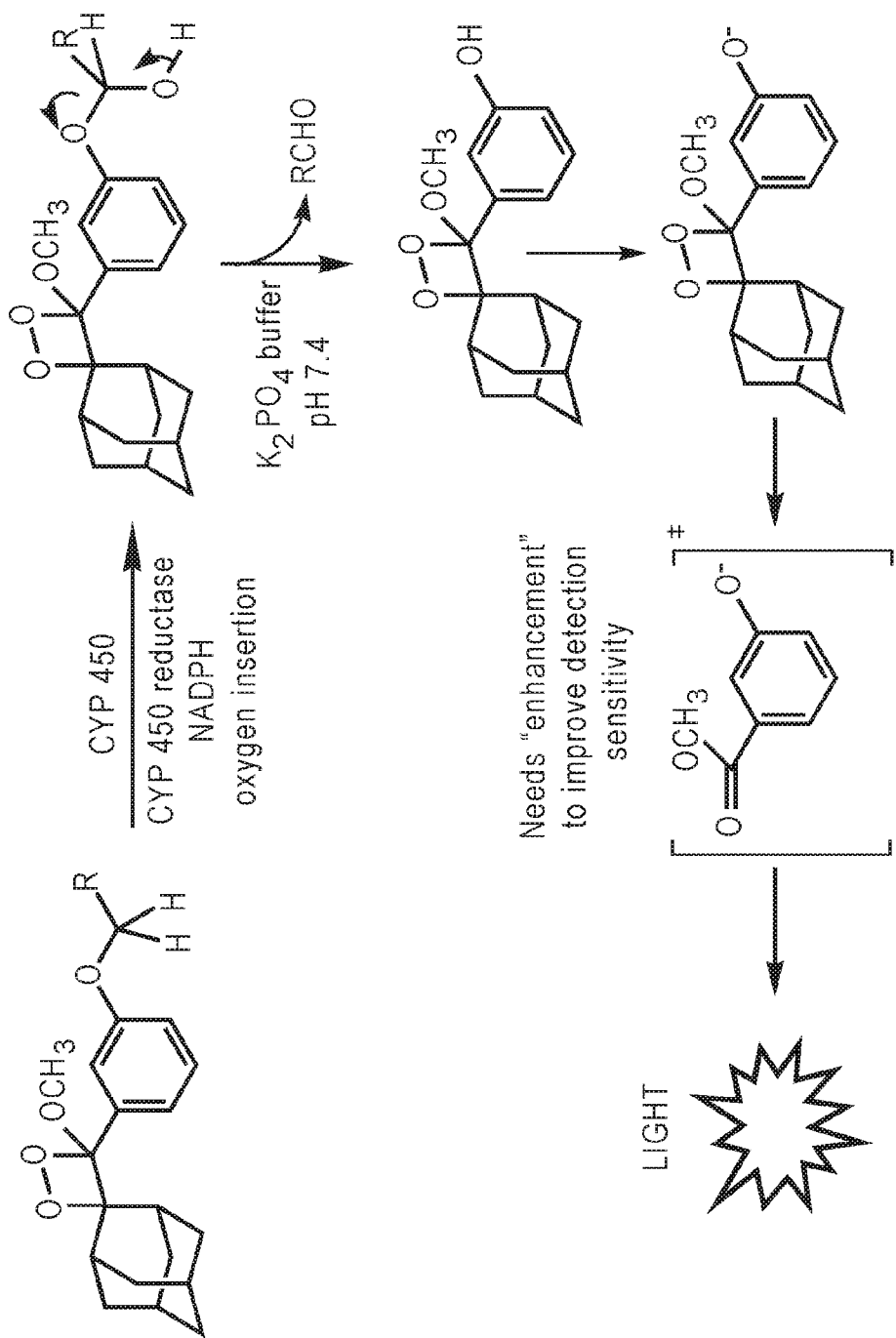
FIG. 1 shows the mechanism of oxidative enzyme activation of a 1,2-dioxetane chemiluminescent substrate with resulting light emission.
Figure 2A:
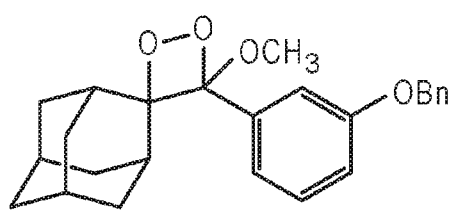
FIG. 2A and FIG. 2B show examples of some CYP450 dioxetane substrates.
Figure 2B:
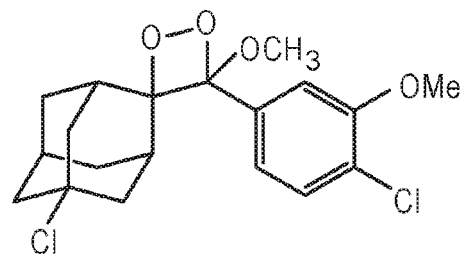
Figure 2C:
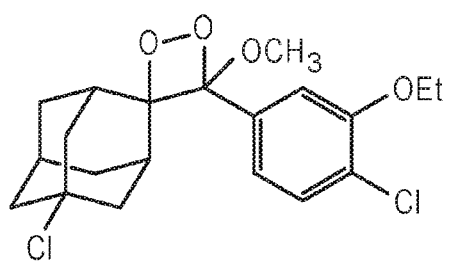
FIG. 2C shows CDP-Star-Et 3.
Figure 2D:
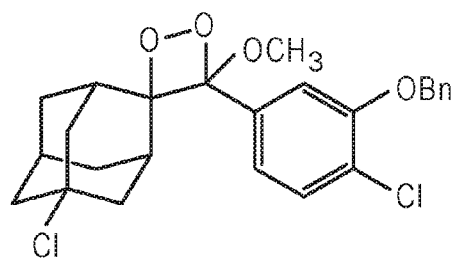
FIG. 2D shows CDP-Star-Bn 4.
Figure 2E:
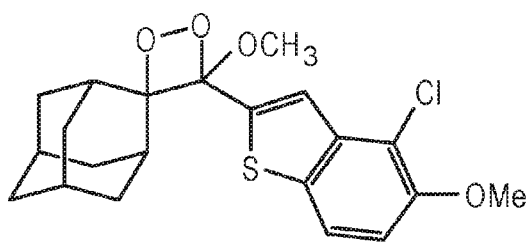
FIG. 2E shows Cl-BZT-Me 5.
Figure 2F:
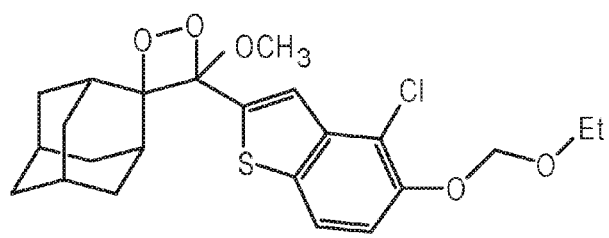
FIG. 2F shows Cl-BZT-EOM 6.
Figure 2G:
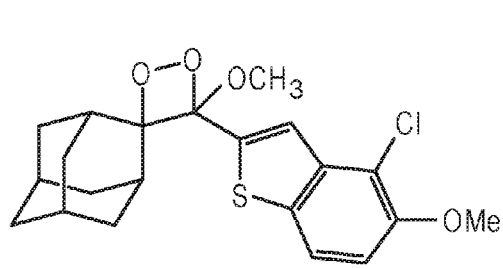
FIG. 2G shows BZT-Me 7.
Figure 2H:
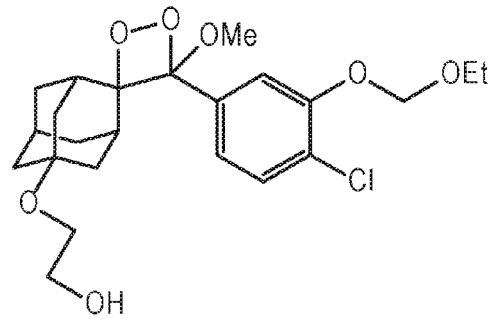
FIG. 2H shows EG-Ad-Cl-Ph-OEOM 8.
Figure 2I:
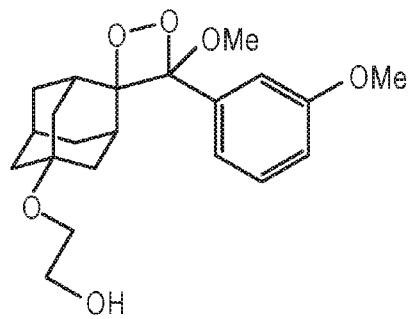
FIG. 2I shows EG-Ad-Ph-OMe 9.
Figure 2J:
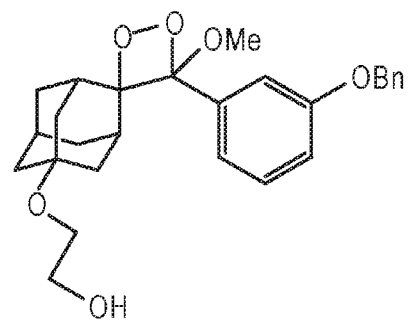
FIG. 2J shows EG-Ad-Ph-OBn 10.
Figure 2K:
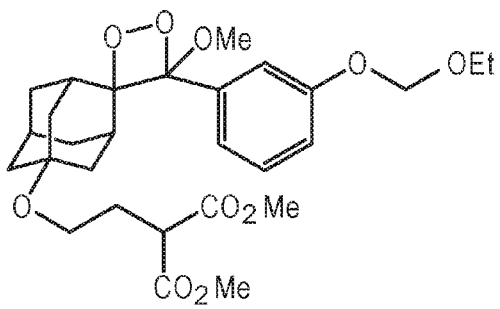
FIG. 2K shows bis-$CO_2$ Me-Ad-Ph-OEOM 11.
Figure 2L:
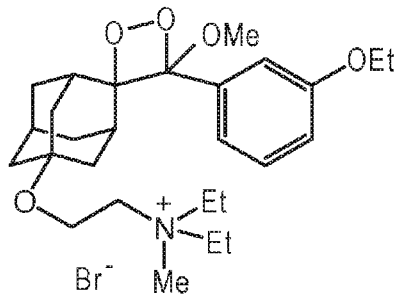
FIG. 2L shows $Q^+$-Amino-Ad-Ph-OEt 12.
Figure 2M:
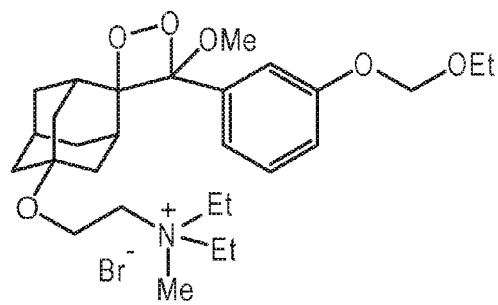
FIG. 2M shows $Q^+$-Amino-Ad-Ph-OEOM 13.
Figure 2N:
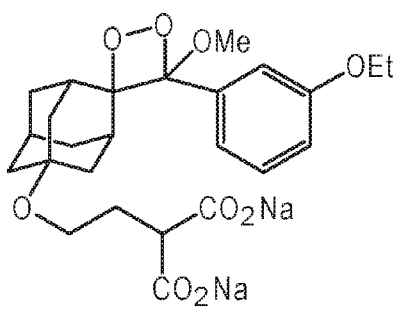
FIG. 2N shows bis-$CO_2$ Na-Ad-Ph-EOt 14.
Figure 2O:
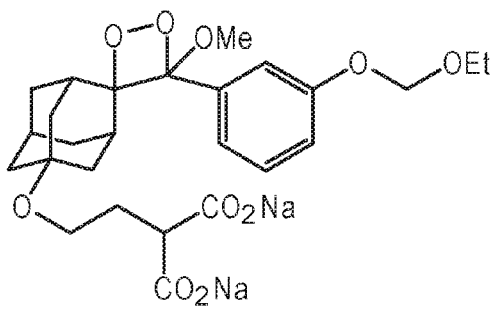
FIG. 2O shows bis-CO2 Na-Ad-Ph-OEOM 15.

For the purpose of interpreting this specification, the following definitions will apply and whenever appropriate, terms used in the singular will also include the plural and vice versa. In the event that any definition set forth below conflicts with the usage of that word in any other document, including any document incorporated herein by reference, the definition set forth below shall always control for purposes of interpreting this specification and its associated claims unless a contrary meaning is clearly intended (for example in the document where the term is originally used). The use of "or" means "and/or" unless stated otherwise. The use of "a" herein means "one or more" unless stated otherwise or where the use of "one or more" is clearly inappropriate. The use of "comprise," "comprises," "comprising," "include," "includes," and "including" are interchangeable and not intended to be limiting. Furthermore, where the description of one or more embodiments uses the term "comprising," those skilled in the art would understand that, in some specific instances, the embodiment or embodiments can be alternatively described using the language "consisting essentially of" and/or "consisting of."

In describing and claiming the embodiments, the following terminology will be used with the definitions set out below.

The term "substrate" refers to a compound or substance that can be enzymatically cleaved to generate a chemiluminescent signal.

The term "enhancer" refers to any substance that enhances the intensity of any released detectable electromagnetic energy over the intensity of any detectable electromagnetic energy released in the absence of the enhancer substance. A macromolecular enhancer substance comprises a naturally-occurring or synthetic macromolecular substance that can provide a hydrophobic microenvironment for the light-emitting substrate.

The term "oxidative enzyme" refers to any enzyme that by oxidative activation of the substrate, releases an intermediate that generates a chemiluminescent signal.

The term "enzyme assay" refers to an assay that comprises the use of an enzyme to cleave a dioxetane compound.

The term "induction assay" refers to any assay that comprises induction. For instance, Cyp1A is a member of the P450 family of enzymes in the liver. It is induced by a variety of agents such as cigarette smoke, omeprazole, methylcholanthrene, and TCDD; it is inhibited by furafylline. One of the Cyp1A substrates is ethoxyresorufin (ERes) which, in the presence of Cyp1A, is converted to the fluorescent compound resorufin. This specific reaction makes ERes an excellent probe for measuring Cyp1A activity. A detectable substrate for Cyp1A can, therefore, be used to measure Cyp1A activity and induction. Induction assays apply a variety of compounds to induce changes in enzymes or enzyme functions.

The term "inhibition assay" refers to any assay that halts or inhibits the start, progress or completion of an assay or enzyme in an assay. The term can refer to assays that can measure the decrease of chemiluminescent signal over time. An inhibitor or similar type molecule is generally added to an assay and the decrease in signal relative to inhibition of the enzyme is measured over time.

The embodiments are described with reference to the figures. In certain instances, The figures may not be to scale and have been exaggerated for clarity of presentation.

CYP450's are membrane-associated heme proteins that metabolize physiologically important compounds in many species of microorganisms, plants and animals. Mammalian CYP450's recognize and metabolize diverse xenobiotics such as drug molecules, environmental compounds and pollutants. Human CYP450 proteins CYP1A2, CYP2C9, CYP2C19, CYP2D6, and CYP3A4, are the major drug metabolizing isoforms (or isozymes), and contribute to the oxidative metabolism of most drugs in clinical use today. Polymorphic variants have also been reported for some CYP450 isoforms, which has implications for the efficacy of drugs in individuals and for the co-administration of drugs.

DESCRIPTION OF VARIOUS EMBODIMENTS

Prior to the late 1990's, cytochrome enzyme inhibition to monitor drug-drug interactions was primarily assayed using LC/MS/MS or HPLC methods using non-labeled, established cytochrome isozyme specific drug substrates. With the advent of fluorescent substrates, pharmaceutical companies rapidly adopted higher throughput fluorescent assays for drug candidate evaluation in earlier phases of discovery; these fluorescent assays are now commercialized by various companies. Additionally, some companies have offered a bioluminescent, secondary enzyme detection assay addressing further assay needs in recent years. Although these substrates have been revolutionary in providing high throughput methods of detecting potential drug-drug interactions and also allowing for screening much earlier in the drug discovery process, they are still limited in their signal to noise ratios, correlation with drug-probe substrate assay results, and lack of isozyme selectivity requiring the use of recombinant enzymes. The fluorescent assays can also give erroneous results when screening lead compounds that can be fluorescent themselves.

The decomposition of chemiluminescent chemical compounds to release electromagnetic, and especially optically detectable, energy—usually luminescence in the form of visible light—is well known and understood. The incorporation of such light emitting reactants in art-recognized immunoassays, chemical assays, nucleic acid probe assays and chemical/physical probe techniques has been widely adopted as a sensitive detection method, usually with significant advantages over colorimetric and fluorescence detection. This is true particularly with the advent of enzymatically-cleavable 1,2-dioxetanes. Applications naming one or more of the inventors herein, as inventors, have clearly established 1,2-dioxetanes as chemiluminescent compounds which can be used as reporters and labels in ultra sensitive assays that can be conducted quickly, without resort to exotic conditions or elaborate apparatus, for the detection of a variety of biological materials. Among these are U.S. Pat. Nos. 4,931,223; 4,931,569; 4,952,707; 4,956,477; 4,978,614; 5,112,960; 5,145,772; 5,220,005; 5,225,584; 5,326,882; 5,330,900; 5,336,596; 5,543,295; 5,547,836; 5,582,980, 5,994,073; 6,140,495; and 6,355,441. All of these patents are incorporated herein by reference. Together this wealth of patent literature addresses 1,2-dioxetanes, stabilized by a typically polycyclic group, such as spiroadamantane bonded to one of the carbons of the dioxetane ring, and a moiety bonded to the remainder carbon of the dioxetane ring which is electron sensitive, such that the activation of the electron sensitive moiety, typically an aryl group, leads to an anion, generally an oxyanion, which is unstable, and decomposes. Through decomposition, the O—O bond is broken and a photon is generated. The same carbon atom to which this electron sensitive moiety is bonded can bear an alkoxy or other electron-active group.

Various compositions and embodiments are described that comprise a dioxetane compound of the form:

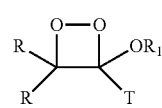

(I)

where R can independently be any branched alkyl or cycloalkyl group which provides stabilization for the dioxetane or where both R groups together form a cycloalkyl or polycycloalkyl moiety spiro bound to the dioxetane ring, wherein each R group or the spiro bound moiety can be unsubstituted or substituted with one or more electron-withdrawing groups or electron donating groups, or groups providing preferential oxidative isozyme substrate recognition, and wherein $R_1$ is an aryl group, or an alkyl group of 1-20 carbon atoms, which can be optionally substituted with 1 or more halogen atoms, and wherein T is an aryl or heteroaryl ring capable of emitting light upon oxidative enzyme activated decomposition of the dioxetane (I).

In various embodiments the compositions can comprise a dioxetane compound wherein the aryl ring of T comprises phenyl or naphthyl, or wherein the heteroaryl ring of T can comprise benzothiazole or benzothiophene. When T comprises a benzothiazole or benzothiophene group, the chemiluminescent emission wavelengths can be shifted toward green wavelengths.

Other compositions and embodiments can comprise a dioxetane compound of the form:

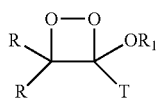

(I)

wherein T is

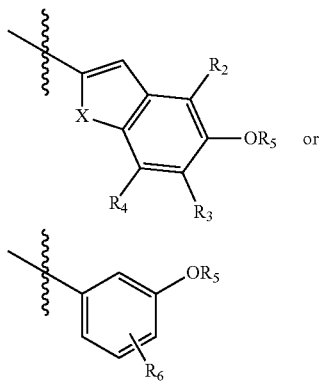

where R can independently be any branched alkyl or cycloalkyl group which provides stabilization for the dioxetane or where both R groups together form a cycloalkyl or polycycloalkyl moiety spiro bound to the dioxetane ring, wherein each R group or the spiro bound moiety can be unsubstituted or substituted with one or more electron-withdrawing groups or electron donating groups, or groups providing preferential oxidative isozyme substrate recognition, and wherein $R_1$ is an aryl group, or an alkyl group of 1-20 carbon atoms, which can be optionally substituted with 1 or more halogen atoms; and wherein $R_2$, $R_3$, $R_4$, and $R_6$ can be independently H, or an electroactive group, which can be electron-withdrawing or electron-donating. Examples of $R_2$, $R_3$, $R_4$, and $R_6$ groups are halo (F, Cl, Br, I), trialkylammonium (—$NR_3^+$), trialkylphosphonium (—$PR_3^+$), alkylamido (—NHCOR, —NRCOR), arylamido (—NHCOAr, NRCOAr, NArCOAr), arylcarbamoyl (—NHCOOAr, —NRCOOAr), alkylcarbamoyl (—NHCOOR, NRCOOR), cyano (—CN), nitro (—$NO_2$), ester (—COOR, COOAr), alkyl- or arylsulfonamido (—$NHSO_2R$, —$NHSO_2Ar$), trifluoromethyl (—$CF_3$), alkyl (—R), aryl (—Ar), trialkyl-, triaryl- or alkylarylsilyl (—$SiR_3$, —$SiAr_3$, —$SiArR_2$), alkyl- or arylamidosulfonyl (—$SO_2NHCOR$, —$SO_2NHCOAr$), alkyl- or arylsulfonyl (—$SO_2R$, —$SO_2Ar$), alkyl- or arylthioethers (—SR, —SAr), alkoxy (—OR), or aryloxy (—OAr) substituents. $R_5$ is a group that can be removed upon activation by an oxidative enzyme. $R_5$ can comprise an alkyl group, such as methyl (-Me), ethyl (-Et), or any alkyl group of 1-20 carbon atoms. $R_5$ can also comprise an arylmethylene group (—$CH_2Ar$) such as benzyl (—$CH_2Phe$). $R_5$ can be unsubstituted or substituted. For example, $R_5$ can be substituted with ethers such as alkoxymethyl (—$CH_2OR$), methoxymethyl (—$CH_2OMe$), ethoxymethyl (—$CH_2OEt$), aryloxymethyl (—$CH_2OCH_2Ar$), and benzyloxymethyl (—$CH_2OCH_2Phe$). $R_5$ can be substituted with other groups consisting of halo (F, Cl, Br, I), trialkylammonium (—$NR_3^+$), trialkylphosphonium (—$PR_3^+$), alkylamido (—NHCOR, —NRCOR), arylamido (—NHCOAr, NRCOAr, NArCOAr), arylcarbamoyl (—NHCOOAr, —NRCOOAr), alkylcarbamoyl (—NHCOOR, NRCOOR), cyano (—CN), nitro (—$NO_2$), ester (—COOR, COOAr), alkyl- or arylsulfonamido (—$NHSO_2R$, —$NHSO_2Ar$), trifluoromethyl (—$CF_3$), alkyl (—R), aryl (—Ar), trialkyl-, triaryl- or alkylarylsilyl (—$SiR_3$, —$SiAr_3$, —$SiArR_2$), alkyl- or arylamidosulfonyl (—$SO_2NHCOR$, —$SO_2NHCOAr$), alkyl- or arylsulfonyl (—$SO_2R$, —$SO_2Ar$), alkyl- or arylthioethers (—SR, —SAr), alkoxy (—OR), or aryloxy (—OAr) substituents, as long as the oxidative enzyme activity to release an aryloxy intermediate is preserved.

Various compositions are described wherein $R_2$ comprises H or halogen. Halogens can comprise bromine, fluorine, chlorine and iodine.

Other compositions are described wherein X is selected from the group consisting of S, N, and O. In some embodiments, $R_6$ can comprise a substituted or unsubstituted aryl group. Examples of oxidative enzyme chemiluminescent substrates are illustrated in FIG. 2.

Other compositions are also described wherein R is selected from cycloalkyl or polycyclic spiro bound moieties. In one embodiment, both R groups together form a spiroadamantyl group, which can be unsubstituted, or substituted at either head carbon, or both, with an electron active (electron withdrawing or electron donating) group, including alkoxy of 1-7 carbon atoms, halo, alkyl, and the like. Exemplary substituents on the adamantyl group are set forth in U.S. Pat. Nos. 5,112,960 and 5,330,900, and are incorporated herein by reference. Other substituents include groups that provide oxidative isozyme specificity. These can include, but are not limited to, substituted alkoxy substituents, having polar or charged groups such as ester, mono- or dicarboxylic acid, mono- or dicarboxylate, and ammonium groups. Beyond spiroadamantyl groups, the identity of each R group is selected so as to provide steric stabilization for the dioxetane to prevent premature decomposition (see FIG. 2 for examples of dioxetane substrate structures).

The enzymatic reaction scheme for an oxidative enzyme and a chemiluminescent 1, 2 dioxetane substrate is shown in FIG. 1. The alkyl group (R—$CH_2$ or R—CHX) is the enzyme reaction site, and can be a factor for conferring isozyme specificity. Activation by the oxidative enzyme and subsequent in situ hydrolysis results in conversion of the substrate to a meta-stable phenol dioxetane at neutral pH, or an unstable phenolate dioxetane at basic pH. Phenolate dioxetane, generated in situ under basic assay conditions, or generated by addition of a basic solution such as Accelerator II, rapidly breaks down to a nascent emitter in the singlet excited state, which then gives off light upon decay to ground state. Quantum light emission, resulting in better detection sensitivity, can be improved by inclusion of a polymeric enhancer.

Dioxetanes are typically used with enhancement agents, which are configured so as to sequester the dioxetane in hydrophobic regions, to avoid the chemiluminescent quenching that can be observed in the presence of water. These enhancement molecules can include onium quaternary polymers, including phosphonium, sulfonium and ammonium polymers, poly(vinylbenzyltrimethylammonium chloride) (TMQ), poly(vinylbenzyltributylammonium chloride) (TBQ), poly(vinylbenzyltributylphosphonium chloride), poly(vinylbenzyltrioctyl phosphonium chloride), and poly(vinylbenzyldimethylbenzylammonium chloride) (BDMQ), a natural substance such as bovine serum albumin or similar type biological or protein based molecules or compounds, a fatty-free bovine serum albumin, or any enhancement additive which improves the enhancement of detected chemiluminescence emission effected by the enhancing substance. Representative polymers and their effects are set forth in U.S. Pat. Nos. 5,145,772 and 5,547,836, which are incorporated herein by reference. These polymers can be used alone, or together with a surfactant additive, to further improve the enhancement value, as disclosed in U.S. Pat. No. 5,994,073, also incorporated herein by reference.

These embodiments are also directed to the use of chemiluminescent, enzymatically cleavable substituted 1,2-dioxetanes in art-recognized assays, including assays for detecting enzymes or levels of enzyme activity in samples, to kits for use in such assays, and to like uses and methods for accomplishing such uses.

For example, when using the various embodiments to detect an enzyme in a sample, the sample is contacted with a dioxetane bearing a group capable of being cleaved by the oxidative enzyme being detected. The enzyme cleaves the dioxetane's enzyme oxidizable group to form a negatively charged substituent (e.g., an oxygen anion) bonded to the dioxetane. This negatively charged substituent in turn destabilizes the dioxetane, causing the dioxetane to decompose to form a fluorescent chromophore group that emits light energy (see FIG. 1). It is the luminescence of this chromophore group that is detected (using, e.g., a cuvette, or light-sensitive film in a camera luminometer, or a photodiode or photoelectric cell, or a photomultiplier tube) as an indication of the presence of the enzyme. By measuring the intensity of luminescence, the concentration of the enzyme in the sample can also be determined.

A wide variety of assays exist which use visually detectable methods and devices to determine the presence or concentration of a particular oxidative enzyme in a sample. The above-described dioxetanes can be used in any of these assays. Examples of such assays include direct enzyme activity assays, enzyme inhibition or activation assays, and enzyme induction or reduction assays. Chemiluminescent CYP450 assays using novel 1,2-dioxetane substrates can be used to monitor CYP450 isozyme activity from various samples including recombinant human (or other) CYP450 microsomes, bodily fluids, tissue (liver, stomach, and the like), tissue microsomal fractions, tissue extracts, cells (hepatocytes, stem cells, and the like), cell extracts, tissue or cell supernatants, organism, or other test samples. Such assays are often used for determining CYP450 isozyme induction in response to a drug, other compound, or stimulus (see FDA's Draft Guidance for Industry: Drug Interaction Studies—Study Design, Data Analysis, and Implications for Dosing and Labeling" Available online at http://www.fda.gov/cder/biologics/qa.htm), but can also be used to quantify enzyme from various sources. Assays for monitoring CYP450 isozyme activity from crude samples, such as human liver microsomes (HLMs), should ideally be based on substrates that have strong isozyme or isozyme-family selectivity for the CYP450 being addressed. Monitoring isozyme activity from more pure samples, such as rhCYP450X microsomes, does not require that the substrate have the same degree of isozyme selectivity. Several novel 1, 2 dioxetane substrates including BZT-Me (7), Cl-BZT-Me (4), CDP-Star-Me (2), and CDP-Star-Et (3) show a strong specificity for 2C19 and 2C18 isozymes. Substrates EG-Ad-Cl-Ph-OEOM (8), Q+-Amino-Ad-Ph-OEt (12) and Q+-Amino-Ad-Ph-OEOM (13) show strong specificity for the CYP3A family isozymes. Substrates AMPPD-Bn (1) and CDP-Star-Bn (4) also show strong specificity for the CYP3A family isozymes, but show significant activity from CYP2C19 under CYP2C19 assay conditions. Substrates bis-$CO_2$Na-Ad-Ph-OEt dxt (14) and bis-$CO_2$Na-Ad-Ph-OEOM dxt (15) show high specificity for CYP2C8. To ensure that monitored enzyme activity is, indeed, attributed to the enzyme of interest, the isozyme-specific inhibitor negative control should always be performed. The assays are typically performed in aqueous environments, but assays in mixed solvent or non-aqueous environments are also included in the various embodiments. Assays performed in a solid matrix or on solid support are also included.

CYP450 enzyme activity assays determine if enzyme is present, and if so, to what extent. Direct enzyme activity assays are especially applicable for drug-drug interaction (DDI) induction assays to determine if a drug increases the amount of a specific CYP450 isozyme. Increased or decreased production of a given CYP450 can lead to toxicity.

Enzyme inhibition or activation assays can be performed on a test molecule or plurality/library of test molecules in the drug discovery phase, where it is desirable to know if a molecule, compound, or drug lead inhibits or activates CYP450 enzymes of interest, as such effects can lead to adverse patient side affects referred to as drug-drug interactions (DDIs). Some CYP450 enzymes are, themselves, potential drug targets for various indications, such that a researcher may want to screen for CYP450 enzyme inhibitors or activators in order to find drug leads for that indication. For these reasons, researchers can screen molecules, mixtures of molecules (such as plant extracts), or molecule libraries to determine if a molecule affects CYP450 activity. The various embodiments describe inhibition assays (e.g., IC50 assays) that can be performed using not only rhCYP microsome enzyme sources, but more biologically relevant non-rhCYP microsome enzyme sources such as human liver microsomes, bodily fluids, tissue (liver, stomach, and the like), tissue microsomal fractions, tissue extracts, cells (hepatocytes, stem cells, or other), cell extracts, tissue or cell supernatants, or other test samples. Crude samples, such as the enzyme sources mentioned above in which the enzyme is not purified, will perform more optimally using dioxetane CYP450 substrates that are isozyme-specific under the assay conditions (see Table 1 for substrate specificity). The assay can also be performed in a 2-step (endpoint) or 1-step (kinetic or endpoint) mode as described herein.

Enzyme induction assays can be performed on a test molecule, mixture of molecules, or plurality/library of test molecules in the drug discovery phase, where it is desirable to know if a molecule, compound, or drug lead results in increased or decreased CYP450 enzyme levels. As with enzyme inhibition or activation effects (manifest as changes in enzyme activity), such changes in enzyme levels can also lead to adverse drug-drug interactions due to increased or decreased drug clearance. For this reason, researchers can screen molecules, mixtures of molecules (such as plant extracts), or molecule libraries to determine if a molecule affects CYP450 enzyme levels.

Various embodiments are provided comprising kits. Kits can be used to conduct assays involving chemiluminescent reporter molecules, such as an oxidative enzyme chemiluminescent substrate as disclosed in the various embodiments. Kits can further comprise an enhancement substance for increasing the chemiluminescent signal obtained from the dioxetane substrate upon activation by an oxidative enzyme.

Kits can comprise an oxidative enzyme substrate, an enhancer, a substrate formulation with or without an enhancer for detecting a substance in a sample comprising various dioxetane compounds. Kits can further comprise oxidative enzymes which in the presence of the dioxetanes cause the dioxetane to decompose, and water soluble enhancers which enhance chemiluminescence emission detectable from the decomposition of the dioxetane. Kits can optionally comprise instructions, packaging, or various types of labeling and/or reagents.

EXAMPLES

Example 1

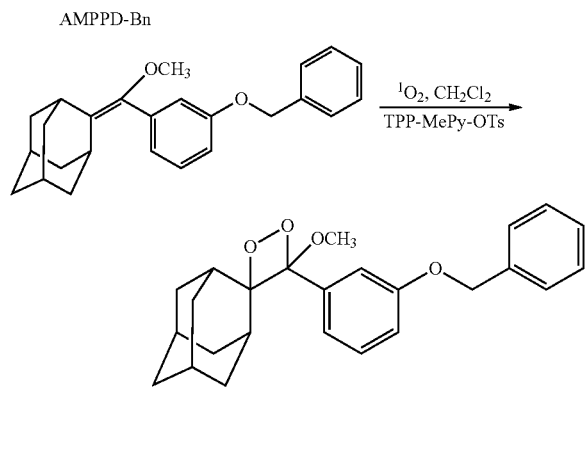

AMPPD-Bn (Compound 1)

To a solution of AMPPD-Bn Enol Ether 1a[1] (1.02 g, 2.84 mmole) in 15 ml of $CH_2Cl_2$ was added 25 drops of sensitizer TPP-MePy-OTs (5, 10, 15, 20-Tetrakis(1-methyl-4-pyridinio) porphyrin tetra(p-toluenesulfonate) stock solution (2 mg/ml MeOH). The mixture was cooled below 10° C. and irradiated with a 400 W sodium lamp under continuous oxygen bubbling. Thin layer chromatography (TLC) after 50 minutes of irradiation showed the reaction was not complete, because some of the sensitizer had stuck to the glass wall of the reaction vessel. An additional 10 ml of $CH_2Cl_2$, 2 ml of MeOH and 5 drops of TPP-Me-Py-OTs stock solution were added, the mixture was continuously irradiated for 40 minutes. TLC showed the reaction was complete this time. The reaction mixture was concentrated by rotary evaporation below 20° C., and purified by silica gel chromatography, eluting with 5-10% EtOAC in hexanes to give 1.21 g of light yellow gum. After trituration of the product with a mixture of hexanes and a few drops of $CH_2Cl_2$, yellow solid dropped out of solution. The suspension was cooled in the freezer overnight. The precipitate was collected by filtration and dried under vacuum at room temperature for 60 minutes, to yield 1 g (89.3%) of the product 1 as a light yellow powder. For more information, see R-R Juo and B Edwards, U.S. Pat. No. 5,225,584, for substituting m-benzyloxybenzaldehyde for m-anisaldehyde in Example 4.

Example 2

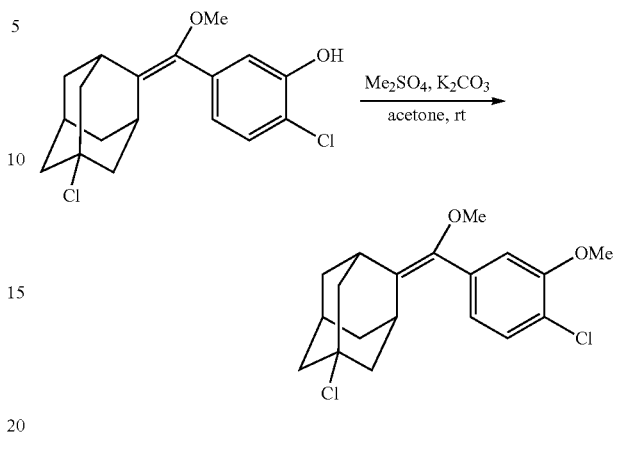

CDP-Star-Me EE (Compound 2b)

To a suspended mixture of the CDP-Star Phenol Enol Ether 2a[2] (1.05 g, 3.1 mmole) and $K_2CO_3$ (0.86 g, 6.2 mmole, 2 equiv.) in 10 ml of acetone, dimethyl sulfate (0.44 ml, 4.6 mmole, 1.5 equiv.) was added slowly at room temperature. The reaction vessel was sealed with a septum and stirred overnight for 23 hours. TLC showed the reaction was complete. The reaction mixture was concentrated by rotary evaporator; the residue was partitioned between saturated $NaHCO_3$ solution and $CH_2Cl_2$. The aqueous layer was extracted three times with $CH_2Cl_2$. The combined $CH_2Cl_2$ solution was then washed with brine, dried over anhydrous $Na_2SO_4$ and concentrated. The crude product was purified by silica gel chromatography, eluting with 3-10% EtOAc in hexanes to yield 1.08 g (98%) of the product 2b as a white solid.

IR ($CHCl_3$): 3005, 2935, 2858, 2830, 1590, 1573, 1485, 1465, 1450, 1400, 1297, 1249, 1177, 1092, 1080, 1062, 1032, 1022, 865, 825 $cm^{-1}$.

$^1$H NMR (400 MHz, $CDCl_3$): δ 7.34 (d, J=8 Hz, 1H), 6.88, (d, J=1.6 Hz, 1H), 6.81 (dd, J=8, 2 Hz, 1H), 3.91 (s, 3H), 3.46 (br. s, 1H), 3.31 (s, 3H), 2.78 (br. s, 1H), 2.11-2.33 (m, 7H), 1.64-1.92 (m, 4H). For more information, see A Sparks, B Edwards, I Bronstein, U.S. Pat. No. 5,582,980.

Example 3

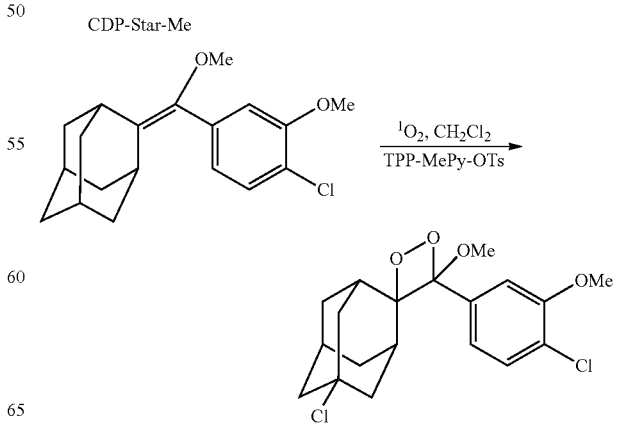

CDP-Star-Me (Compound 2)

To a solution of CDP-Star-Me Enol Ether 2b (988 mg, 2.8 mmole) in 22 ml of 10% MeOH in $CH_2Cl_2$ was added 22 drops of sensitizer TPP-MePy-OTs [5, 10, 15, 20-tetrakis(1-methyl-4-pyridinio) porphyrin tetra(p-toluenesulfonate)] stock solution (2 mg/ml MeOH). The mixture was cooled below 10° C. and irradiated with a 400 W sodium lamp under continuous oxygen bubbling. TLC after 60 minutes of irradiation showed the reaction was complete. The reaction mixture was concentrated by rotary evaporation below 20° C. and purified by silica gel chromatography, eluting with 7-10% EtOAC in hexanes to give a light yellow gum. Upon trituration with MeOH, the gum solidified. After filtration, 1 g (95.3%) of product 2 was obtained as a light yellow powder.

Example 4

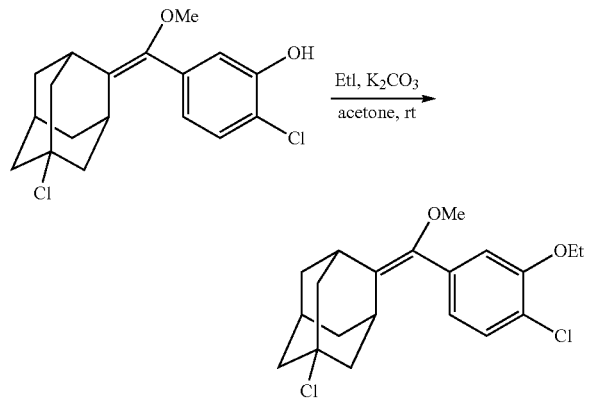

CDP-Star-Et EE (Compound 3b)

To a suspended mixture of the CDP-Star Phenol Enol Ether 2a (905 mg, 2.7 mmole) and $K_2CO_3$ (737 mg, 5.3 mmole, 2 equiv.) in 10 ml of acetone, iodoethane (0.32 ml, 4 mmole, 1.5 equiv.) was added slowly at room temperature. The reaction vessel was sealed with a septum and stirred overnight for 69.5 hours. TLC showed the reaction was incomplete. An additional 20 drops of iodoethane and 100 mg of $K_2CO_3$ was added, the reaction mixture was continued to stir overnight. TLC showed only trace of the starting material remained this time. The reaction mixture was concentrated by rotary evaporator; the residue was partitioned between saturated $NaHCO_3$ solution and $CH_2Cl_2$. The aqueous layer was extracted three times with $CH_2Cl_2$. The combined $CH_2Cl_2$ solution was then washed with brine, dried over anhydrous $Na_2SO_4$ and concentrated. The crude product was purified by silica gel chromatography, eluting with 0-5% EtOAc in hexanes to yield 932 mg (95.1%) of the product 3b as a white powder.

IR ($CHCl_3$): 2990, 2935, 2858, 2830, 1590, 1573, 1485, 1475, 1448, 1408, 1395, 1290, 1249, 1178, 1092, 1082, 1060, 1024, 825 $cm^{-1}$.

$^1$H NMR (400 MHz, $CDCl_3$): δ 7.36 (d, J=7.9 Hz, 1H), 6.86, (d, J=1.8 Hz, 1H), 6.80 (dd, J=8, 1.8 Hz, 1H), 4.12 (q, J=6.9 Hz, 2H), 3.45 (br. s, 1H), 3.30 (s, 3H), 2.78 (br. s, 1H), 2.11-2.33 (m, 7H), 1.64-1.91 (m, 4H), 1.49 (t, J=6.9 Hz, 3H).

Example 5

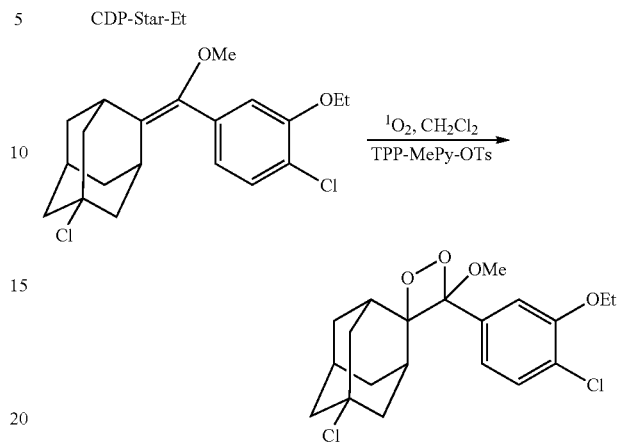

CDP-Star-ET (Compound 3)

To a solution of CDP-Star-Et Enol Ether 3b (705 mg, 1.9 mmole) in 20 ml of 10% MeOH in $CH_2Cl_2$ was added 30 drops of sensitizer TPP-MePy-OTs [5,10,15,20-tetrakis(1-methyl-4-pyridinio) porphyrin tetra(p-toluenesulfonate)] stock solution (2 mg/ml MeOH). The mixture was cooled below 10° C. and irradiated with a 400 W sodium lamp under continuous oxygen bubbling. TLC after 80 minutes of irradiation showed the reaction was complete. The reaction mixture was concentrated by rotary evaporation below 20° C. and purified by silica gel chromatography, eluting with 3-5% EtOAC in hexanes to give a soft yellow powder. Upon further trituration with hexanes, 702 mg (91.5%) of the product 3 was obtained as a light yellow powder.

Example 6

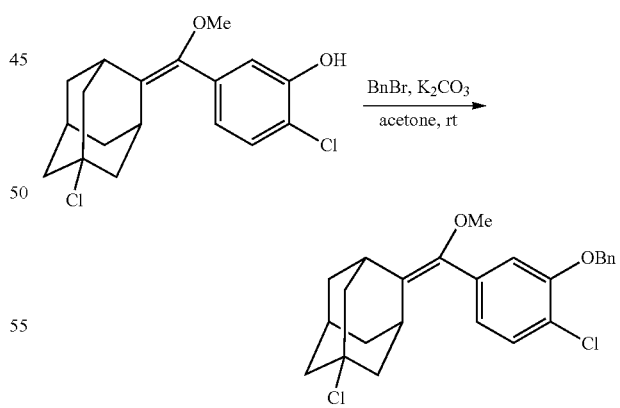

CDP-Star-Bn EE (Compound 4a)

To a suspended mixture of the CDP-Star Phenol Enol Ether 2a (1.03 g, 3 mmole) and $K_2CO_3$ (840 mg, 6 mmole, 2 equiv.) in 10 ml of acetone, benzylbromide (0.54 ml, 4.6 mmole, 1.5 equiv.) was added slowly at room temperature. The reaction vessel was sealed with a septum and stirred overnight for 23 hours. TLC showed the reaction was complete. The reaction mixture was concentrated by rotary evaporator; the residue was partitioned between saturated NaHCO₃ solution and CH₂Cl₂. The aqueous layer was extracted three times with CH₂Cl₂. The combined CH₂Cl₂ solution was then washed with brine, dried over anhydrous Na₂SO₄ and concentrated. The crude product was purified by silica gel chromatography, eluting with 5-10% EtOAc in hexanes to yield 1.35 g (>100%) of the product 4a as a colorless gum.

IR (CHCl₃): 3000, 2935, 2858, 2832, 1590, 1572, 1484, 1450, 1406, 1382, 1290, 1266, 1178, 1094, 1082, 1060, 1023, 825, 695 cm⁻¹.

¹H NMR (400 MHz, CDCl₃): δ 7.28-7.49 (m, 6H), 6.87 (d, J=1.9 Hz, 1H), 6.81 (dd, J=8.2, 1.9 Hz, 1H), 5.19 (s, 2H), 3.42 (br. s, 1H), 3.21 (s, 3H), 2.66 (br. s, 1H), 2.14-2.30 (m, 5H), 2.04-2.09 (m, 2H), 1.56-1.88 (m, 4H).

Example 7

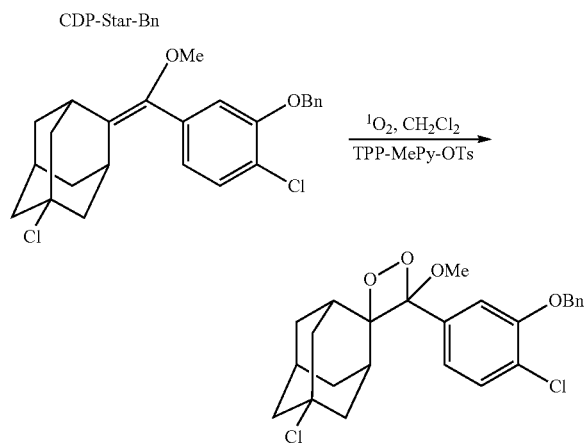

CDP-Star-Bn (Compound 4)

To a solution of CDP-Star-Bn Enol Ether 4a (1.26 g, 2.9 mmole) in 22 ml of 10% MeOH in CH₂Cl₂ was added 25 drops of sensitizer TPP-MePy-OTs [5, 10, 15, 20-tetrakis (1-methyl-4-pyridinio) porphyrin tetra(p-toluenesulfonate)] stock solution (2 mg/ml MeOH). The mixture was cooled below 10° C. and irradiated with a 400 W sodium lamp under continuous oxygen bubbling. TLC after 60 minutes of irradiation showed the reaction was complete. The reaction mixture was concentrated by rotary evaporation below 20° C. and purified by silica gel chromatography, eluting with 5-10% EtOAC in hexanes to give a light yellow powder. The product 4 was further purified by trituration with hexanes, to yield 1.2 g (89.2%) of light yellow powder.

Example 8

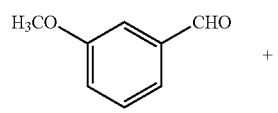

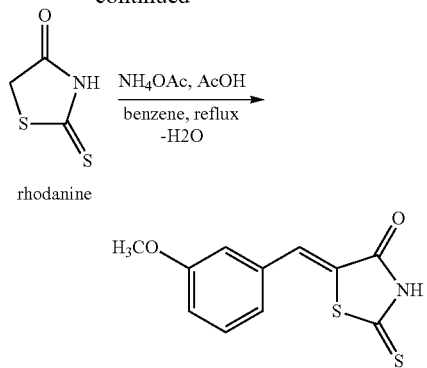

5-(3-Methoxybenzylidene) rhodanine (compound 2

1): In a 500 ml three-neck round-bottomed flask, equipped with Dean-Stark condenser, dropping funnel, argon gas outlet and a large egg-shaped stirring bar, was placed rhodanine (Aldrich, 21.89 g, 164 mmole, 1 equiv.), ammonium acetate (1.29 g, 16.8 mmole, 0.1 equiv.), glacial acetic acid (4 ml) and benzene (165 ml). The suspended mixture was vigorously stirred and heated to reflux in an oil bath; m-anisaldehyde (Aldrich, 20 ml, 164 mmole) was added via dropping funnel over 10 minutes to the refluxing mixture. The mixture became cloudy after 90 minutes and approximately 4.5 ml of water was collected in the Dean-Stark trap. After cooling slowly to 0° C., the precipitate was collected by filtration and rinsed with cold water. After air-drying over the weekend, 39.78 g (96.3%) of rhodanine adduct 20 was obtained as a yellow powder.

¹H NMR (400 MHz, DMSO-d₆): δ 7.63 (s, 1H), 7.43-7.49 (m, 1H), 7.14-7.18 (m, 2H), 7.06-7.10 (m, 1H), 3.81 (s, 3H).

Example 9

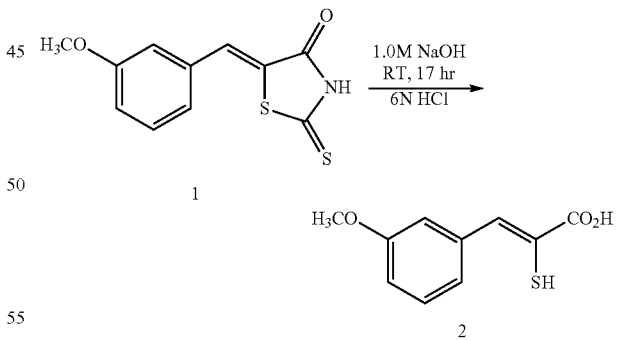

β-(3-Methoxyphenyl)-α-mercaptoacrylic acid (compound 21)

A yellow suspended solution of the rhodanine adduct 20 in 1 N NaOH solution (27.8 g in 700 ml H₂O, 4.5 equiv.) was stirred at room temperature under an argon atmosphere. Mild heating and swirling of the reaction mixture (20 minutes) facilitated the stirring; a clear dark orange solution was obtained after 140 minutes at room temperature. The mixture continued stirring overnight for a total of 18 hours. After overnight stirring, TLC showed the reaction was complete. The mixture was acidified carefully with 6N HCl at 0° C. Fine white particles dropped out of the solution initially, then changed to a sticky brown gum. The gum was scratched until it solidified, and then the chunky solid was pressed to a powder and collected by filtration. After air-drying, 30.97 g (95%) of the acid 21 was obtained as a tan solid. The proton NMR of 21 in DMSO-$d_6$ was complicated; it probably was a mixture composed of the product tautomers and the air-oxidized disulfide byproducts. The impure product was used immediately for the next benzothiophene ring closure reaction.

Example 10

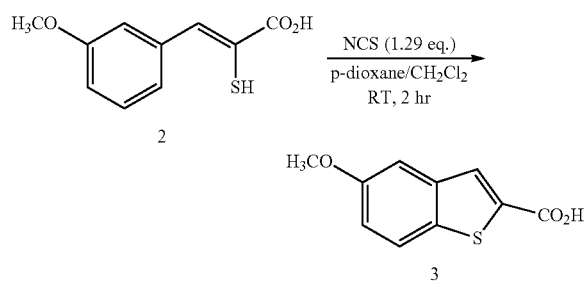

5-Methoxy-benzo[b]thiophene-2-carboxylic acid (compound 22)

To a tan solution of the acid 21 (30.6 g, 145.8 mmole) in 1,4-dioxane (350 ml), a suspended solution of N-chlorosuccinimide (25.11 g, 188 mmole, 1.29 equiv.) was added over 30 minutes via pipette at room temperature. The mixture became a cloudy orange color during the addition. After 2 hours of stirring, the color of the mixture lightened. The volatile components were removed on a rotary evaporator; the orange residue was pumped under vacuum until it solidified. The crude product was then partitioned between EtOAc (400 ml) and saturated NaHCO$_3$ solution (150 ml). After the aqueous layer was separated, the organic phase was further extracted with saturated NaHCO$_3$ solution twice (2×150 ml). All of the aqueous extracts were combined and carefully acidified with 6 N HCl at 0° C. (watch out for violent CO$_2$ evolution!). Solid was collected by filtration and washed with water. After air-drying over the weekend, 31.63 g (~100%) of the benzothiophene acid 22 was obtained as a light orange powder. The product 22 was contaminated with the inseparable benzothiophene regio-isomer, and was used for the next esterification and chlorination without purification.

Example 11

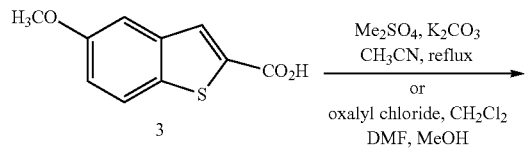

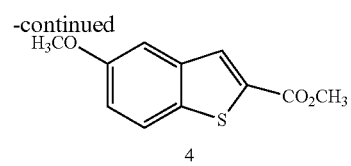

Methyl 5-methoxy-benzo[b]thiophene-2-carboxylate (BZT ester) (compound 23)

To a suspended solution of the benzothiophene acid 22 (31.5 g, 145.8 mmole based on the previous reaction) in CH$_3$CN (500 ml) and K$_2$CO$_3$ (40.3 g, 291.6 mmole, 2 equiv.), was added dimethyl sulfate (20.7 ml, 218.7 mmole, 1.5 equiv.) at room temperature under an argon atmosphere. The yellow slurry was refluxed for 3.5 hours. After cooling to room temperature, the K$_2$CO$_3$ salts were removed by filtration and rinsed with CH$_2$Cl$_2$. The combined filtrates were concentrated to generate 34.94 g of orange solid. The crude product was triturated with 70% CH$_2$Cl$_2$ in hexanes, and the insoluble white crystalline solid, collected upon filtration, was discarded. The filtrate was concentrated to yield 33.51 g (>100%) of brown solid. The crude product mixture of three close RF value components based on TLC was used for the next chlorination without purification.

The benzothiophene acid 22 can also be converted to the methyl ester 23 by the oxalyl chloride-MeOH method: To a suspended solution of the benzothiophene acid 22 (9 g, 43.3 mmole) in CH$_2$Cl$_2$, oxalyl chloride (4.7 ml, 54 mmole, 1.25 equiv.) was added dropwise at room temperature under an argon atmosphere. When the mixture was treated with a catalytic amount of DMF (0.1 ml), moderate gas evolution occurred. After 2 hours of stirring, gas evolution subsided, and a clear red solution resulted. Anhydrous MeOH (25.5 ml, 14.5 equiv.) was added slowly and the mixture was heated at 40° C. for 1.5 hr, and stirred at room temperature overnight. The volatile components were removed on a rotary evaporator to yield an orange gum, which solidified under vacuum to afford 11.64 g (>100%) of impure methyl ester 23.

Example 12

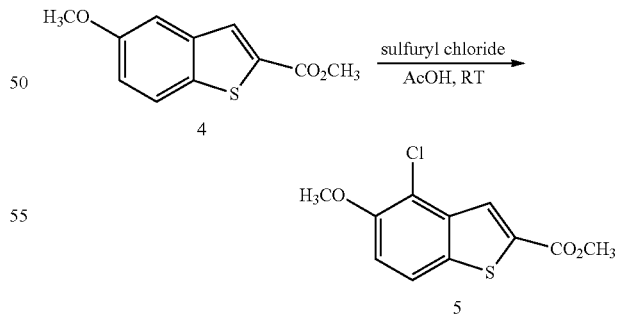

Methyl 4-chloro-5-methoxy-benzo[b]thiophene-2-carboxylate (Cl-BZT ester) (compound 11)

A suspended solution of the BZT ester 23 (33.51 g, 145.8 mmole based on the acid 22) in glacial acetic acid (420 ml) was heated gently until a clear solution resulted. Upon cooling back to room temperature, sulfuryl chloride (SO$_2$Cl$_2$, 14.6 ml, 182.3 mmole) was added dropwise to the solution over 15 minutes under an argon atmosphere. Heavy precipitate dropped out of the solution in the middle of addition, the slurry was vigorously stirred for 3 hours; then poured into a flask containing 500 ml of cold water. Orange precipitate was collected by filtration and rinsed with cold water. The solid was air-dried overnight to generate 28.07 g of the crude BZT ester 24. The product was purified by triturations in MeOH twice (2×150 ml) and hexanes three times (3×200 ml) successively, to produce 14.49 g (38.7% overall yield started from the acid 22) of the Cl-BZT ester 24. The purity was >95% based on its proton NMR spectrum. Additional crops could be pulled out from the mother liquors by tedious silica gel purifications and triturations.

IR (CHCl$_3$): 3034, 3015, 2960, 2844, 1719, 1603, 1527, 1462, 1435, 1420, 1329, 1303, 1250, 1184, 1064, 963, 928, 868 cm$^{-1}$.

$^1$H NMR (400 MHz, CDCl$_3$): δ 8.18 (d, J=0.7 Hz, 1H), 7.72 (dd, J=9.1, 0.7 Hz, 1H), 7.22 (d, J=9 Hz, 1H), 4.00 (s, 3H), 3.98 (s, 3H).

The dichloro regioisomer (3.08 g) was partially isolated as a white powder in >78% purity after silica gel purification (50~60% CH$_2$Cl$_2$ in hexanes) and trituration twice with 10% CH$_2$Cl$_2$ in hexanes and 100% hexanes, respectively on its enriched residue. Both IR & proton NMR spectra clearly confirmed the structure shown below.

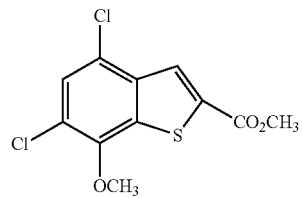

5i

IR (CHCl$_3$): 3032, 3013, 2957, 1725, 1582, 1525, 1462, 1432, 1352, 1300, 1254, 1178, 1137, 1077, 1066, 968, 978, 864 cm$^{-1}$.

$^1$H NMR (400 MHz, CDCl$_3$): δ 8.13 (s, 1H), 7.43 (s, 1H), 4.04 (s, 3H), 3.97 (s, 3H).

Example 13

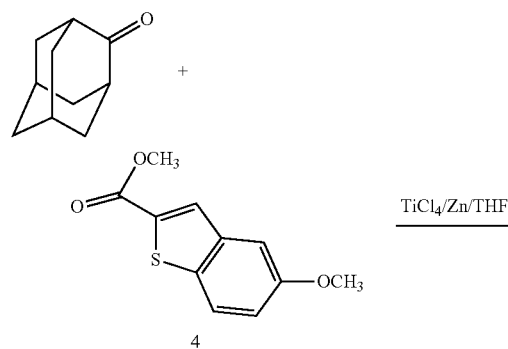

4

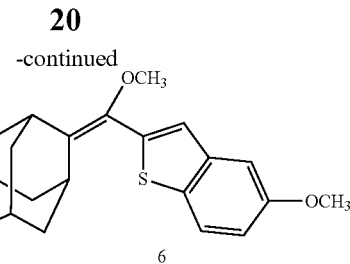

6

BZT Methoxyenol Ether (Compound 7a)

TiCl$_4$ (10 mL, 91 mmole) was added to a suspension of Zn (24 g, 367 mmole) in THF (100 mL). A yellow solid was formed upon the addition. More THF (30 mL) was used for rinsing. The mixture was heated to reflux until the yellow solid was all dissolved. Triethylamine (50 mL, 360 mmole) was added and the mixture was refluxed for 0.5 h. A mixture of BZT ester 23 (2 g, 9 mmole) and 2-adamantanone (3.4 g, 22.7 mmole) in THF (12 mL) was added dropwise to the TiCl$_4$/Zn mixture. More 2-adamantanone (0.6 g, 4 mmole) in THF (5 mL) was added slowly over 15 minutes. The resulting mixture was refluxed for 1 h, and then cooled to room temperature. Dichloromethane (30 mL), hexane (50 mL) and water (30 mL) were added. The organic solution was decanted off the solids and evaporated on a rotavap. The inorganic slurry was washed with the organic solvents recovered from the evaporation, and the washing was pooled with the product fraction and evaporated again. The slurry washing process was repeated once more. A yellowish semi-solid was recovered upon evaporation. This crude product was purified by silica gel chromatography using hexane and a mixture of hexane/dichloromethane as eluting solvents. About 3.1 g (9 mmole) of 7a were recovered as a yellowish solid.

$^1$H NMR (400 MHz, CDCl$_3$): δ 7.66 (d, J=8.76 Hz, 1H), 7.22 (d, J=2.55 Hz, 1H), 7.13 (s, 1H), 6.96 (dd, J=8.76, 2.49 Hz, 1H), 3.88 (s, 3H), 3.47 (s, 3H), 3.26 (s, broad, 1H), 3.03 (s, broad, 1H), 2.0-1.84 (m, broad, 12H).

Example 14

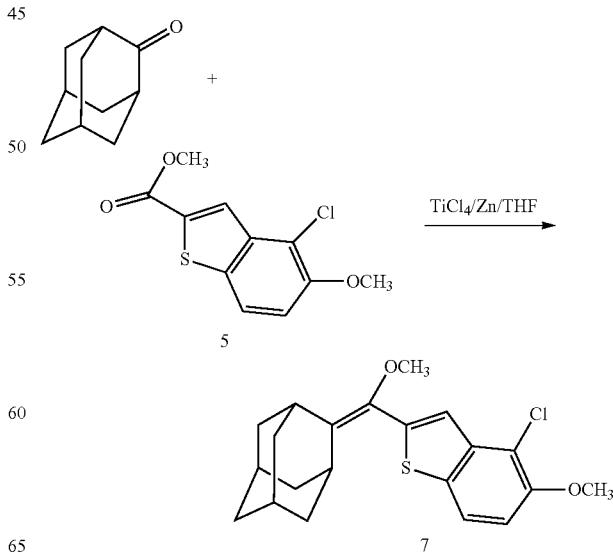

Cl-BZT Methoxyenol Ether (Compound 5a)

TiCl$_4$ (8.6 mL, 78 Mmole) was Added to a suspension of Zn (20 g, 306 mmole) in THF (60 mL) A yellow solid was formed upon the addition. More THF (40 mL) was used for rinsing. The mixture was heated to reflux until the yellow solid was all dissolved. Triethylamine (44 mL, 317 mmole) was added and the mixture was refluxed for 0.5 h. A mixture of Cl-BZT ester 24 (2 g, 7.8 mmole) and 2-adamantanone (3 g, 20 mmole) in THF (35 mL) was added dropwise to the TiCl$_4$/Zn mixture. More 2-adamantanone (0.5 g, 3.3 mmole) in THF (5 mL) was added slowly over 15 minutes. The resulting mixture was refluxed for 1 h, and then cooled to room temperature. Dichloromethane (30 mL), hexane (50 mL) and water (30 mL) were added. The organic solution was decanted, and rotary evaporated. The inorganic slurry was washed with the organic solvents recovered from the evaporation, and the washing was pooled with the product fraction and evaporated again. The slurry washing process was repeated once more. A yellowish solid was recovered. The crude solid was purified by silica gel chromatography using hexane and a mixture of hexane/dichloromethane as eluting solvents. About 2.65 g (7.1 mmole) of 5a was recovered as a slightly yellowish solid.

$^1$H NMR (400 MHz, CDCl$_3$, ppm): δ 7.68 (d, J=8.6 Hz, 1H), 7.36 (s, 1H), 7.09 (d, J=9 Hz, 1H), 4.03 (s, 3H), 3.54 (s, 3H), 3.33 (s, broad, 1H), 3.11 (s, broad, 1H), 2.06-1.89 (m, broad, 12H).

Example 15

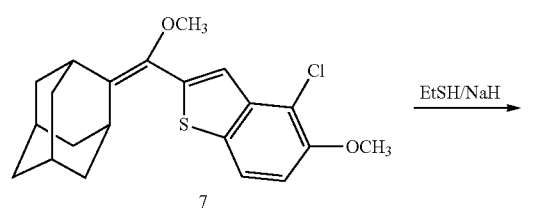

Cl-BZT Hydroxyenol Ether (Compound 5b)

Cl-BZT-OMe 5a (2.65 g, 7.1 mmole) was dissolved in DMF (15 mL). This solution was added to a mixture of: [Ethanethiol (1 mL, 13.5 mM) added to a solution of DMF (10 mL) with NaH (60% in mineral oil) (1.13 g, 28.3 mM)]. The resulting mixture was heated to 95-105° C. for 45 minutes (TLC indicated that the reaction was complete), then cooled to room temperature, diluted with water (100 mL) and saturated sodium bicarbonate (100 mL). A yellowish gum was collected by filtration, purified by chromatography through a plug silica gel column, eluting with a mixture of hexane/dichloromethane. About (2.4 g, 6.7 mmole) of 5b was recovered as a slightly yellowish solid.

$^1$H NMR (400 MHz, CDCl$_3$, ppm): δ 7.61 (dd, J=8.55, 0.5 Hz, 1H), 7.27 (d, J=0.6 Hz, 1H), 7.09 (d, J=8.5 Hz, 1H), 5.59 (s, 1H), 3.53 (s, 3H), 3.31 (s, broad, 1H), 3.06 (s, broad, 1H), 2.05-1.88 (m, broad, 12H).

Example 16

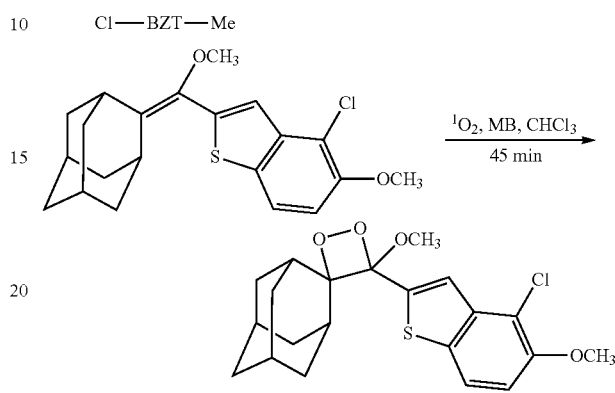

Cl-BZT-Me (Compound 5)

To a solution of Cl-BZT-Me EE 5a (99 mg, 0.26 mmole) in 8 ml of CHCl$_3$ was added 12 drops of sensitizer Methylene Blue stock solution (2 mg/ml MeOH). The mixture was cooled below 10° C. and irradiated with a 400 W sodium lamp under continuous oxygen bubbling. TLC after 45 minutes of irradiation showed the reaction was complete. The reaction mixture was concentrated by rotary evaporator below 20° C. and purified by silica gel chromatography, eluting with 5-10% EtOAC in hexanes to give 102.4 mg (95.3%) of the product 5 as a light yellow gum.

Example 17

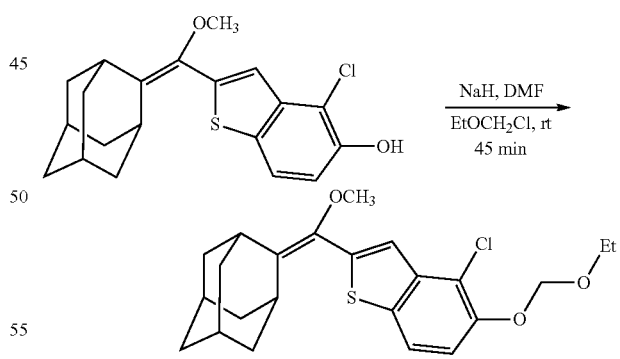

Cl-BZT-EOM EE (Compound 6a)

60% NaH in mineral oil (85.6 mg, 2.1 mmole, 5 equiv.) was rinsed three times with hexanes; the resulting wet gray powder was blown to dryness by argon. After suspending the dry NaH in 4 ml of DMF, the slurry was added to a solution of Cl-BZT-phenol EE 5b (154.5 mg, 0.43 mmole) in 2 ml of DMF at room temperature under an argon atmosphere. The color of the reaction mixture changed to yellow immediately. An extra 1.5 ml of DMF was used to rinse the sample vial and added to the mixture. After 50 minutes of stirring, the slurry was added EtOCH$_2$Cl (0.12 ml, 1.3 mmole, 3 equiv.) dropwise. The color of the reaction mixture discharged immediately. The reaction was quenched with H$_2$O carefully at 0° C. after 45 minutes of stirring at room temperature. The aqueous layer was extracted three times with 10% EtOAc in hexanes. The combined organic solution was washed with brine, dried over anhydrous Na$_2$SO$_4$, and concentrated, to yield 6a as a colorless gum.

The crude product was purified by silica gel chromatography, eluting with 0-5% EtOAc in hexanes, to give 166.1 mg (92.6%) of the product 6a as a colorless gum.

$^1$H NMR (400 MHz, CDCl$_3$): δ 7.61 (d, 1H, J=8.8 Hz), 7.33 (s, 1H), 7.26 (d, J=8.7 Hz, 1H), 5.34 (s, 2H), 3.84 (q, J=7.4 Hz, 2H), 3.49 (s, 3H), 3.28 (br. s, 1H), 3.05 (br. s, 1H), 1.81-2.05 (m, 12H), 1.26 (t, J=7.3 Hz, 3H).

Example 18

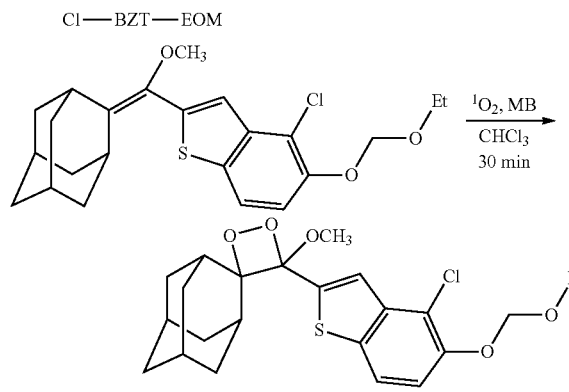

Cl-BZT-EOM (Compound 6)

To a solution of Cl-BZT-EOM EE 6a (148.9 mg, 0.36 mmole) in 8 ml of CHCl$_3$ was added 17 drops of sensitizer Methylene Blue stock solution (2 mg/ml MeOH). The mixture was cooled below 10° C. and irradiated with a 400 W sodium lamp under continuous oxygen bubbling. TLC after 30 minutes of irradiation showed the reaction was complete. The reaction mixture was concentrated by rotary evaporator below 20° C. and purified by silica gel chromatography, eluting with 0-5% EtOAC in hexanes to give 140 mg (87.3%) of the product 6 as a light yellow gum.

Example 19

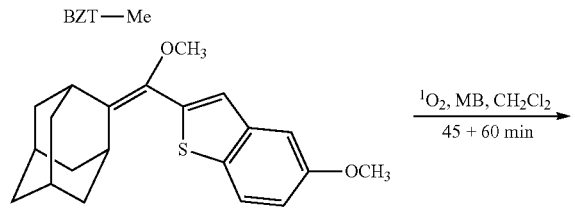

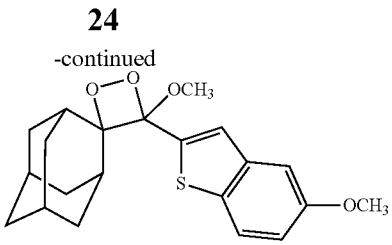

BZT-Me (Compound 7)

To a solution of BZT-Me EE 7a (125 mg, 0.37 mmole) in 6 ml of CH$_2$Cl$_2$ was added 15 drops of sensitizer Methylene Blue stock solution (2 mg/ml CD$_3$OD/CH$_2$Cl$_2$). The mixture was cooled to about 0° C. and irradiated with a 400 W sodium lamp under continuous oxygen bubbling for 105 minutes. More sensitizer solution, 40 drops, was added during the reaction. TLC (3% EtOAc/hexane) showed the reaction was complete. The reaction mixture was concentrated by rotary evaporator and purified by silica gel chromatography, eluting with 1% EtOAC in hexanes to give 86 mg (63%) of the product 7 as a white foam.

Example 20

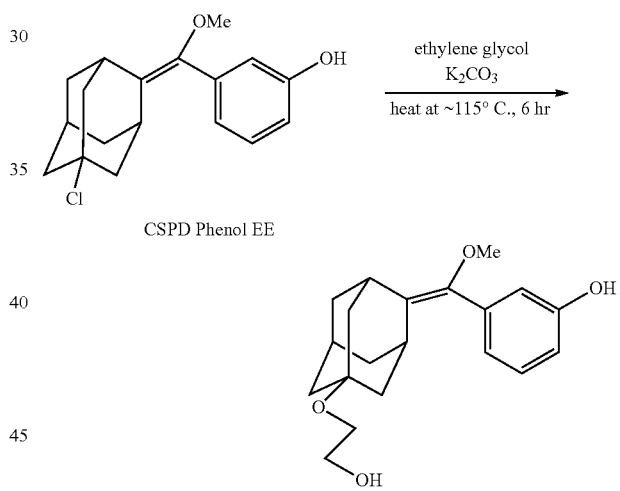

EG-Ad-Phenol EE (Compound 26)

A mixture of the starting material CSPD phenol EE 25[3] (4 g, 13.1 mmole), K$_2$CO$_3$ (3.63 g, 26.2 mmole, 2 equiv.) and ethylene glycol (16 ml, 287 mmole, 22 equiv.) was placed in a 100 ml round-bottomed flask and heated to 110-115° C. in an oil bath. The suspended mixture became clear at ~85° C. TLC after 6 hours of heating showed that the reaction was complete. The reaction mixture was cooled to room temperature; about 10 ml of ethylene glycol were pumped off under vacuum with gentle heating. The remaining residue was partitioned between EtOAc and NaHCO$_3$ solution. The aqueous layer was extracted three times with EtOAc. The combined EtOAc solution was washed by brine, dried over anhydrous Na$_2$SO$_4$ and concentrated. The crude gummy product was purified by a silica gel plug, eluting with 20~35% acetone in CH$_2$Cl$_2$, to yield 4.06 g (93.7%) of the product 26 as an orange gum.

IR (CHCl$_3$): 3600, 3340, 3005, 2930, 2858, 1595, 1585, 1495, 1357, 1300, 1096, 888 cm$^{-1}$.

$^1$H NMR (400 MHz, CDCl$_3$): δ 7.20-7.26 (m, 1H), 6.84-6.89 (m, 1H), 6.77-6.83 (m, 2H), 3.67-3.75 (m, 2H), 3.52-3.57 (m, 2H), 3.47 (br. s, 1H), 3.32 (s, 3H), 2.85 (br. s, 1H), 2.28 (br. s, 1H), 1.60-1.94 (m, 10H).

For more information, see Juo, B Edwards, I Y Bronstein, U.S. Pat. No. 5,330,900.

Example 21

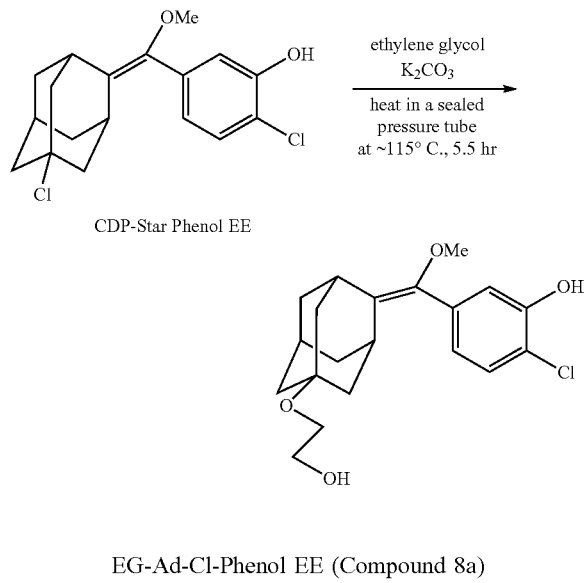

EG-Ad-Cl-Phenol EE (Compound 8a)

A mixture of CDP-Star phenol EE 2a (1.08 g, 3.2 mmole), K$_2$CO$_3$ (883 mg, 6.4 mmole, 2 equiv.) and ethylene glycol (8 ml, 143 mmole, 45 equiv.) in a sealed pressure tube was heated at 105~115° C. for 5.5 hours. Workup was done in the same manner as the previous reaction, the crude product was purified by silica gel chromatography, eluting with 3060% EtOAc in hexanes, to give 1.19 g (100%) of product 8a as a light yellow gum.

IR (CHCl$_3$): 3540, 3340, 3005, 2930, 2858, 1575, 1482, 1410, 1310, 1247, 1170, 1095, 1062, 1046, 895, 886 cm$^{-1}$.

$^1$H NMR (400 MHz, CDCl$_3$): δ 7.30 (d, J=7.7 Hz, 1H), 6.96 (d, J=1.8 Hz, 1H), 6.82 (dd, J=8.2, 1.8 Hz, 1H), 3.66-3.73 (m, 2H), 3.52-3.56 (m, 2H), 3.45 (br. s, 1H), 3.30 (s, 3H), 2.81 (br. s, 1H), 2.27 (br. s, 1H), 1.65-1.93 (m, 10H).

Example 22

Pivaloyl-EG-Ad-Cl-Ph-Pivaloyl Ester EE (Compound 8b)

To a solution of EG-Ad-Cl-Phenol EE 8a (781.7 mg, 2.14 mmole) in 15 ml of CH$_2$Cl$_2$, was added Et$_3$N (1.5 ml, 10.7 mmole, 5 equiv.) slowly at room temperature under an argon atmosphere. The mixture was cooled in an ice-bath and treated with trimethylacetyl chloride (0.66 ml. 5.4 mmole, 2.5 equiv.) dropwise. White Et$_3$N.HCl precipitate dropped out of solution immediately. A small amount of 4-dimethylaminopyridine (DMAP) was added to the slurry, and the solution was stirred at room temperature overnight. The resulting dark brown slurry was then partitioned between CH$_2$Cl$_2$ and NaHCO$_3$ solution. The aqueous layer was extracted three times with CH$_2$Cl$_2$. The combined CH$_2$Cl$_2$ solution was washed with brine, dried over anhydrous Na$_2$SO$_4$ and concentrated. The crude orange oil was purified by a silica gel chromatography, eluting with 0-10% EtOAc in hexanes, to yield 872.2 mg (76.3%) of the product 8b as a yellow gum.

IR (CHCl$_3$): 3020, 2975, 2935, 2858, 1760, 1725, 1480, 1400, 1286, 1210, 1170, 1100, 720-780, 664 cm$^{-1}$.

$^1$H NMR (400 MHz, CDCl$_3$): δ 7.42 (d, J=8.2 Hz, 1H), 7.12 (dd, J=8.2, 2.1 Hz, 1H), 7.06 (d, J=2.1 Hz, 1H), 4.17 (m, 2H), 3.61 (m, 2H), 3.46 (br. s, 1H), 3.31 (s, 3H), 2.82 (br. s, 1H), 2.27 (br. s, 1H), 1.64-1.92 (m, 10H), 1.41 (s, 9H), 1.22 (s, 9H).

Example 23

Pivaloyl-EG-Ad-Cl-Phenol EE (Compound 8c)

To a yellow solution of Pivaloyl-EG-Ad-Cl-Ph-Pivaloyl ester EE 8b (849 mg, 1.59 mmole) in 7.5 ml of MeOH, was added K$_2$CO$_3$ (0.3 g, 2.2 mmole, 1.4 equiv.) at 0° C. The slurry became an orange color while stirring 25 minutes at 0° C. and 90 minutes at room temperature. The reaction mixture was concentrated by rotary evaporation. The residue was partitioned between 20% EtOAc/hex and NaHCO$_3$ solution, and extracted three times with 20% EtOAc/hex. The combined organic solution was washed by brine, dried over anhydrous Na$_2$SO$_4$ and concentrated. The crude orange gum was purified by a silica gel plug, eluting with 10-20% EtOAc in hexanes, to yield 756.9 mg (100%) of the product 8c as an orange gum.

IR (CHCl$_3$): 3544, 2975, 2935, 2858, 1726, 1575, 1488, 1283, 1170, 1095, 1064, 1046, 975 cm$^{-1}$.

$^1$H NMR (400 MHz, CDCl$_3$): δ 7.29 (d, J=8.3 Hz, 1H), 6.94-6.97 (m, 1H), 6.79-6.84 (m, 1H), 4.16 (t, J=5.2 Hz, 2H), 3.60 (t, J=5.2 Hz, 2H), 3.44 (br. s, 1H), 3.29 (s, 3H), 2.80 (br. s, 1H), 2.26 (br. s, 1H), 1.62-1.90 (m, 10H), 1.21 (s, 9H).

Example 24

Pivaloyl-EG-Ad-Cl-Ph-OEOM EE (Compound 8d)

60% NaH in mineral oil (181.7 mg, 4.5 mmole, 4 equiv.) was rinsed three times with hexanes; the resulting wet gray powder was blown to dryness by argon. After suspending the dry NaH in 6 ml of DMF, the slurry was added to a solution of pivaloyl-EG-Ad-Cl-Phenol EE 8c (510 mg, 1.14 mmole) in 2 ml of DMF at room temperature under an argon atmosphere. An extra 1 ml of DMF was used to rinse the sample vial and added to the reaction mixture. After 50 minutes of stirring, the brown slurry was treated with EtOCH$_2$Cl (0.21 ml, 2.3 mmole, 2 equiv.) dropwise. The reaction mixture was stirred for 2 hours at room temperature. The reaction was then quenched with H$_2$O carefully at 0° C. and extracted three times with 10% EtOAc in hexanes. The combined organic solution was washed with brine, dried over anhydrous Na$_2$SO$_4$, and concentrated, to yield a brownish gum. The crude product was purified by silica gel chromatography, eluting with 10-15% EtOAc in hexanes, to give 302.5 mg (52.5%) of the product 8d as a light yellow gum.

IR (CHCl$_3$): 2975, 2935, 2858, 1726, 1592, 1573, 1481, 1387, 1287, 1165, 1096, 1050, 1014, 1000, 974 cm$^{-1}$.

$^1$H NMR (400 MHz, CDCl$_3$): δ 7.35 (d, J=7.9 Hz, 1H), 7.16 (d, J=2.3 Hz, 1H), 6.90 (dd, J=8.3, 1.9 Hz, 1H), 5.30 (s, 2H), 4.17 (m, 2H), 3.79 (q, J=7.2 Hz, 2H), 3.61 (m, 2H), 3.46 (br. s, 1H), 3.31 (s, 3H), 2.83 (br. s, 1H), 2.27 (br. s, 1H), 1.58-1.92 (m, 10H), 1.23 (t, J=7.1 Hz), 1.22 (s, 9H).

Example 25

EG-Ad-Cl-Ph-OEOM EE (Compound 8e)

To a yellow solution of Pivaloyl-EG-Ad-Cl-Ph-OEOM EE 8d (RRJ-095B-181, 276.6 mg, 0.55 mmole) in 3 ml of MeOH, was added 4.37 M of MeONa in MeOH (0.19 ml, 0.82 mmole, 1.5 equiv.) at room temperature. The reaction vessel was sealed with a septum and stirred overnight. The reaction mixture was concentrated by rotary evaporation. The residue was partitioned between $CH_2Cl_2$ and $NaHCO_3$ solution, and extracted three times with $CH_2Cl_2$. The combined $CH_2Cl_2$ solution was washed by brine, dried over anhydrous $Na_2SO_4$ and concentrated. The crude product was purified by silica gel chromatography, eluting with 30-50% EtOAc in hexanes, to yield 222.1 mg (96.2%) of the product 8e as a light yellow gum.

IR ($CHCl_3$): 3580, 3460, 3000, 2980, 2930, 2858, 1590, 1572, 1480, 1387, 1290, 1240, 1118, 1100, 1062, 1050, 1014, 1000, 975 cm$^{-1}$.

$^1$H NMR (400 MHz, $CDCl_3$): δ 7.34 (d, J=8.1 Hz, 1H), 7.15 (d, J=1.7 Hz, 1H), 6.89 (dd, J=8.1, 1.7 Hz, 1H), 5.30 (s, 2H), 3.78 (q, J=7.2 Hz, 2H), 3.64-3.72 (m, 2H), 3.50-3.55 (m, 2H), 3.46 (br. s, 1H), 3.30 (s, 3H), 2.82 (br. s, 1H), 2.27 (br. s, 1H), 1.59-1.93 (m, 10H), 1.22 (t, J=7.2 Hz, 3H).

The overall yield of the above 4-step reaction sequence is approximately 38.5%.

Example 26

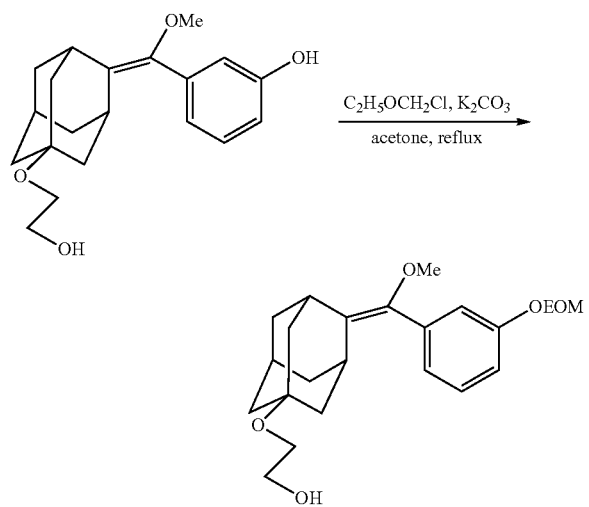

EG-Ad-Ph-OEOM EE (Compound 27)

To a solution of the EG-Ad-Phenol EE 26 (3.08 g, 9.3 mmole) in 50 ml of acetone, was added $K_2CO_3$ (5.15 g, 37.3 mmole, 4 equiv.). The resulting suspended mixture was treated with EtOCH$_2$Cl (1.72 ml, 18.6 mmole, 2 equiv.) dropwise under an argon atmosphere. The reaction mixture was heated to reflux for 4.5 hours; however, TLC showed the reaction was only about 70% complete: in addition to the product spot, there were 2 minor byproduct spots with lesser polarity. These were presumably the bis-EOM ether byproduct and the mono-EOM ether produced at the wrong hydroxyl site on the ethylene glycol side chain. An additional EtOCH$_2$Cl (1 ml, 10.8 mmole) was added and the mixture was refluxed an additional 3 hours. The reaction was cooled to room temperature and concentrated by rotary evaporation. The residue was partitioned between $CH_2Cl_2$ and $NaHCO_3$ solution. The aqueous layer was extracted three times with $CH_2Cl_2$. The combined $CH_2Cl_2$ solution was washed by brine, dried over anhydrous $Na_2SO_4$ and concentrated. The crude product was purified by silica gel chromatography, eluting with 10-20% acetone in hexanes, to yield 2.51 g (69.5%) of the product 27 as a light yellow gum.

IR ($CHCl_3$): 3590, 3460, 3000, 2980, 2930, 2858, 1600, 1578, 1480, 1440, 1355, 1283, 1235, 1170, 1100, 1020, 978, 935 cm$^{-1}$.

$^1$H NMR (400 MHz, $CDCl_3$): δ 7.24-7.31 (m, 1H), 6.97-7.02 (m, 2H), 6.92-6.97 (m, 1H), 5.23 (s, 2H), 3.75 (q, J=7 Hz, 2H), 3.65-3.72 (m, 2H), 3.50-3.56 (m, 2H), 3.47 (br. s, 1H), 3.30 (s, 3H), 2.84 (br. s, 1H), 2.27 (br. s, 1H), 1.60-1.90 (m, 10H), 1.23 (t, J=7 Hz, 3H).

Example 27

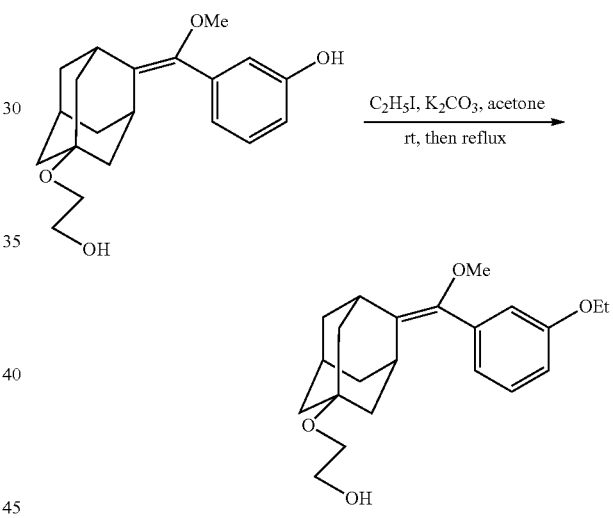

EG-Ad-Ph-OEt EE (Compound 28)

To a solution of the EG-Ad-Phenol EE 26 (3.92 g, 11.9 mmole) in 70 ml of acetone, was added $K_2CO_3$ (4.92 g, 35.6 mmole, 3 equiv.). The suspended mixture was treated with EtI (1.44 ml, 17.8 mmole, 1.5 equiv.) dropwise under an argon atmosphere. TLC after 24 hours of stirring at room temperature showed the reaction was about 70% conversion. Even though additional $K_2CO_3$ (5 g, 36.2 mmole) and EtI (2.74 ml, 33.9 mmole) were added in 2 occasions with an extra 43 of hours stirring, the reaction did not go to completion. The reaction was finally complete by heating at ~60° C. for 5 hours. The reaction mixture was concentrated by rotary evaporation. The residue was partitioned between $CH_2Cl_2$ and $NaHCO_3$ solution. The aqueous layer was extracted three times with $CH_2Cl_2$. The combined $CH_2Cl_2$ solution was washed by brine, dried over anhydrous $Na_2SO_4$ and concentrated. The crude product was purified by a silica gel chromatography, eluting with 10-25% acetone in hexanes, to yield 3.91 g (91.8%) of the product 28 as a light yellow gum.

IR (CHCl$_3$): 3590, 3460, 3005, 2985, 2930, 2858, 1575-1600, 1478, 1440, 1355, 1288, 1240, 1178, 1100, 1048, 968, 928 cm$^{-1}$.

$^1$H NMR (400 MHz, CDCl$_3$): δ 7.23-7.27 (m, 1H), 6.82-6.91 (m, 3H), 4.05 (q, J=7 Hz, 2H), 3.66-3.73 (m, 2H), 3.51-3.57 (m, 2H), 3.49 (br. s, 1H), 3.31 (s, 3H), 2.84 (br. s, 1H), 2.28 (br. s, 1H), 1.59-1.91 (m, 10H), 1.44 (t, J=7 Hz, 3H).

Example 28

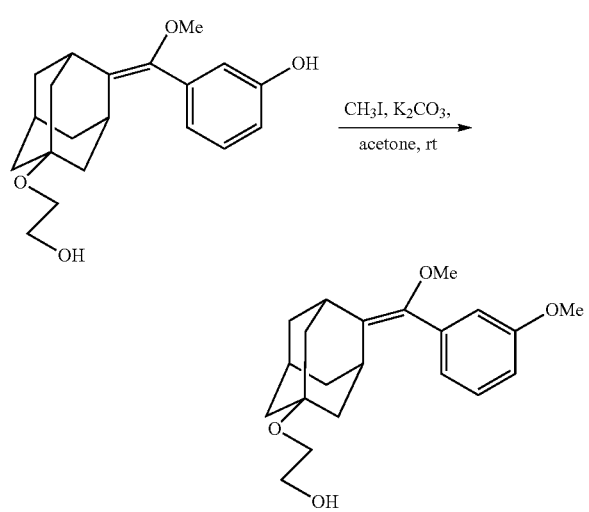

EG-Ad-Ph-OMe EE (Compound 9a)

To a solution of the EG-Ad-Phenol EE 26 (429.8 mg, 1.3 mmole) in 10 ml of acetone, was added K$_2$CO$_3$ (359.5 mg, 2.6 mmole, 2 equiv.). The suspended mixture was treated with MeI (0.12 ml, 1.95 mmole, 1.5 equiv.) dropwise under an argon atmosphere. TLC after 20.5 hours of stirring at room temperature showed the reaction was about 60% complete. Additional K$_2$CO$_3$ (300 mg, 2.2 mmole) and MeI (0.1 ml, 1.6 mmole) were added, and the reaction was stirred for an additional 23 hours. The reaction mixture was concentrated by rotary evaporation. The residue was partitioned between CH$_2$Cl$_2$ and NaHCO$_3$ solution, and extracted three times with CH$_2$Cl$_2$. The combined CH$_2$Cl$_2$ solution was washed by brine, dried over anhydrous Na$_2$SO$_4$ and concentrated. The crude product was purified by silica gel chromatography, eluting first with 10-30% EtOAc in hexanes, followed by 30% acetone in hexanes, to yield 403.5 mg (90%) of the product 9a as a light yellow gum.

IR (CHCl$_3$): 3590, 3450, 3005, 2930, 2858, 1600, 1580, 1465, 1452, 1355, 1288, 1243, 1172, 1163, 1098, 1047, 968, 886 cm$^{-1}$.

$^1$H NMR (400 MHz, CDCl$_3$): δ 7.23-7.26 (m, 1H), 6.82-6.91 (m, 3H), 3.82 (s, 3H), 3.65-3.71 (m, 2H), 3.50-3.55 (m, 2H), 3.47 (br. s, 1H), 3.30 (s, 3H), 2.83 (br. s, 1H), 2.27 (br. s, 1H), 1.59-1.90 (m, 10H).

Example 29

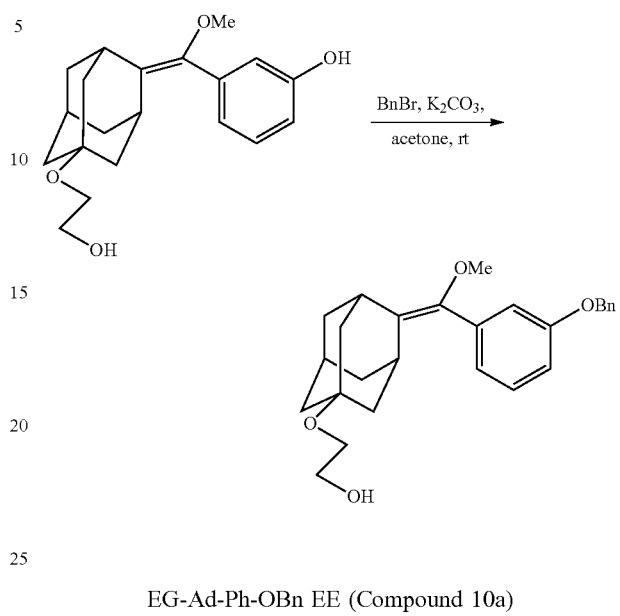

EG-Ad-Ph-OBn EE (Compound 10a)

To a solution of the EG-Ad-Phenol EE 26 (2.99 g, 9.1 mmole) in 23 ml of acetone, was added K$_2$CO$_3$ (2.5 g, 18.1 mmole, 2 equiv.). The suspended mixture was treated with BnBr (1.61 ml, 13.6 mmole, 1.5 equiv.) dropwise under an argon atmosphere. TLC after 20.5 hours of stirring at room temperature showed the reaction was complete. The reaction mixture was concentrated by rotary evaporation. The residue was partitioned between CH$_2$Cl$_2$ and NaHCO$_3$ solution and extracted three times with CH$_2$Cl$_2$. The combined CH$_2$Cl$_2$ solution was washed with brine, dried over anhydrous Na$_2$SO$_4$ and concentrated. The crude product was purified by silica gel chromatography, eluting first with 10-30% EtOAc in hexanes, followed by 25-30% acetone in hexanes, to yield 3.43 g (90%) of the product 10a as a light yellow gum.

IR (CHCl$_3$): 3590, 3450, 3005, 2930, 2858, 1598, 1578, 1453, 1376, 1355, 1288, 1240, 1175, 1163, 1098, 1047, 890, 695 cm$^{-1}$.

$^1$H NMR (400 MHz, CDCl$_3$): δ 7.21-7.47 (m, 6H), 6.87-6.96 (m, 3H), 5.08 (s, 2H), 3.64-3.72 (m, 2H), 3.52 (t, J=4.5 Hz, 2H), 3.46 (br. s, 1H), 3.28 (s, 3H), 2.80 (br. s, 1H), 2.26 (br. s, 1H), 1.55-1.91 (m, 10H).

Example 30

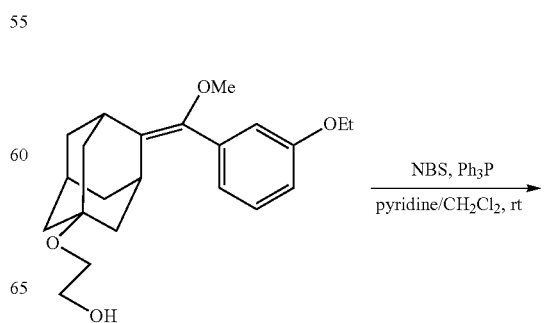

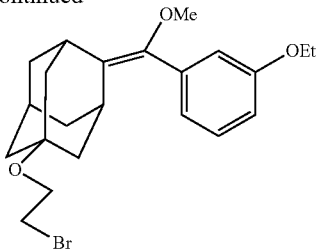

(Br-EtO)-Ad-Ph-OEt EE (Compound 29)

To a solution of triphenylphosphine (3.37 g, 12.8 mmole, 1.5 equiv.) in 36 ml of $CH_2Cl_2$, was added powdered N-bromosuccinimide (2.29 g, 12.8 mmole, 1.5 equiv.) in several portions over 7 minutes at 0° C. under an argon atmosphere. The resulting light brownish mixture was stirred at room temperature for 45 minutes. Pyridine (1.25 ml, 15.4 mmole, 1.8 equiv.) was added to the reaction mixture, the color of the mixture became dark brown immediately. A solution of EG-Ad-Ph-OEt EE 28 (3.07 g, 8.6 mmole) in 18 ml of $CH_2Cl_2$ was added slowly to the reaction mixture over 7 minutes. An extra 7 ml of $CH_2Cl_2$ was used to rinse the sample container and added to the reaction mixture. TLC after 6.5 hours of stirring showed the reaction was complete. The reaction mixture was diluted with an equal volume of hexanes (61 ml) and filtered through a coarse silica gel plug. The column was flushed with 100 ml of 10% EtOAc in hexanes; the filtrate was concentrated by rotary evaporation to yield a slurry. White precipitate was removed by filtration after overnight storage in a refrigerator. The filtrate was concentrated and purified by silica gel chromatography, eluting with 5-7% EtOAc in hexanes to give 3.01 g (83.6%) of the product 29 as a colorless oil.

IR ($CHCl_3$): 3055, 2990, 2930, 2858, 1598, 1578, 1443, 1425, 1265, 1098, 895, 703 $cm^{-1}$.

$^1H$ NMR (400 MHz, $CDCl_3$): δ 7.24-7.30 (m, 1H), 6.83-6.90 (m, 3H), 4.05 (q, J=7 Hz, 2H), 3.73 (t, J=7 Hz, 2H), 3.48 (br. s, 1H), 3.41 (dd, J=7.1, 6.5 Hz, 2H), 3.31 (s, 3H), 2.84 (br. s, 1H), 2.28 (br. s, 1H), 1.56-1.93 (m, 10H), 1.44 (t, J=7 Hz, 3H).

Example 31

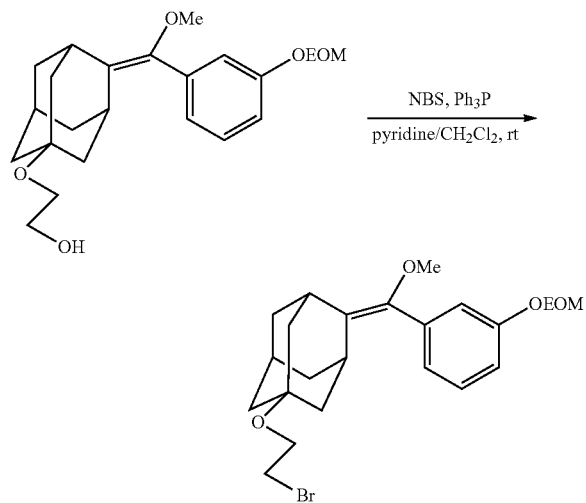

(Br-EtO)-Ad-Ph-OEOM EE (Compound 30)

The product was prepared in the same fashion as in compound 29, by reacting the EG-Ad-Ph-OEOM EE 27 (2.15 g, 5.5 mmole) with an adduct of triphenylphosphine (2.18 g, 8.3 mmole, 1.5 equiv.) and N-bromosuccinimide (1.48 g, 8.3 mmole, 1.5 equiv.) in a mixture of $CH_2Cl_2$ (41 ml) and pyridine (0.8 ml) for 4.5 hours at room temperature. After workup and silica gel purification, 1.95 g (78.1%) of 30 as a pale yellow gum was obtained.

IR ($CHCl_3$): 3000, 2980, 2930, 2855, 1599, 1578, 1483, 1440, 1270, 1098, 1083, 1020, 978 $cm^{-1}$.

$^1H$ NMR (400 MHz, $CDCl_3$): δ 7.22-7.30 (m, 1H), 6.96-7.02 (m, 2H), 6.91-6.97 (m, 1H), 5.23 (s, 2H), 3.69-3.78 (m, 4H), 3.47 (br. s, 1H), 3.40 (t, J=6.9 Hz, 2H), 3.30 (s, 3H), 2.84 (br. s, 1H), 2.27 (br. s, 1H), 1.55-1.92 (m, 10H), 1.23 (t, J=7 Hz, 3H).

Example 32

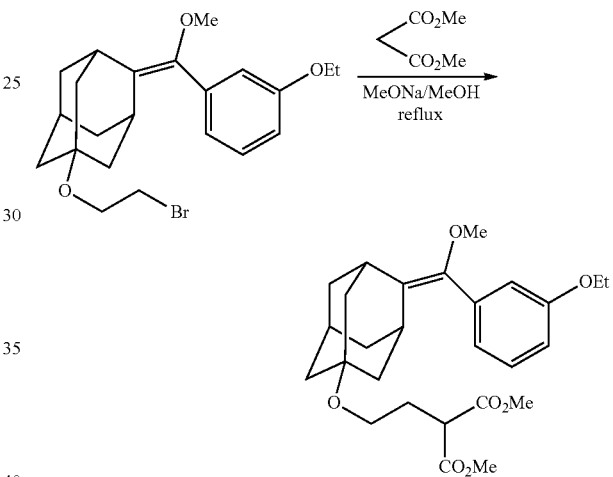

(bis-$MeO_2C$-PrO)-Ad-Ph-OEt EE (Compound 14a)

To a solution of dimethyl malonate (2.7 ml, 23.5 mmole, 6 equiv.) in 14 ml of anhydrous MeOH was added 4.37M MeONa in MeOH (5.4 ml, 23.5 mmole, 6 equiv.) dropwise at room temperature under an argon atmosphere. The reaction mixture was stirred for 40 minutes and added quickly to an immiscible solution of (Br-EtO)-Ad-Ph-OEt EE 29 (1.65 g, 3.9 mmole) in 7 ml of MeOH. An extra 4 ml of MeOH was used to rinse the dimethyl malonate container and added to the reaction mixture. The resulting yellow mixture was heated to reflux for 5 hours; TLC showed the reaction was complete. Cooled back to room temperature, the reaction mixture was concentrated by rotary evaporation. The residue was partitioned between 20% EtOAc/hex and $NaHCO_3$ solution, and extracted three times with 20% EtOAc/hex. The combined organic solution was washed with brine, dried over anhydrous $Na_2SO_4$ and concentrated. The crude product was purified by a silica gel chromatography, eluting with 10-20% EtOAc in hexanes, to yield 1.7 g (92.1%) of the product 14a as a colorless oil.

IR ($CHCl_3$): 3035, 2985, 2930, 2858, 1735, 1574-1600, 1438, 1340, 1286, 1195-1245, 1158, 1098, 1025 $cm^{-1}$.

$^1H$ NMR (400 MHz, $CDCl_3$): δ 7.22-7.28 (m, 1H), 6.81-6.90 (m, 3H), 4.05 (q, J=7.3 Hz, 2H), 3.76 (s, 3H), 3.74

(s, 3H), 3.62 (t, J=7.3 Hz, 1H), 3.46 (t, J=5.8 Hz), 3.44 (br. s, 1H), 3.29 (s, 3H), 2.80 (br. s, 1H), 2.24 (br. s, 1H), 2.10-2.18 (m, 2H), 1.57-1.92 (m, 10H), 1.43 (t, J=6.8 Hz, 3H).

Example 33

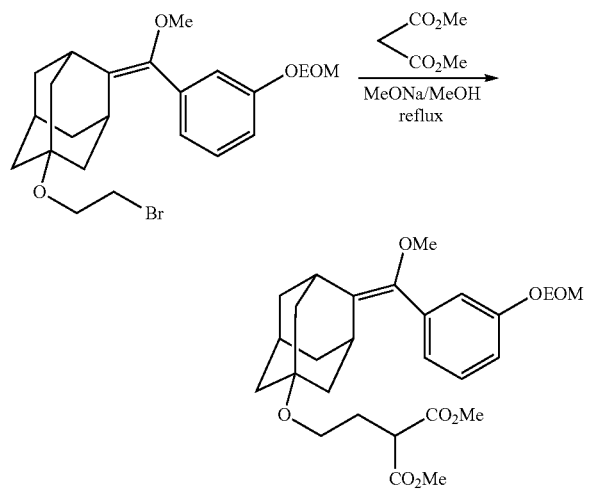

(bis-MeO₂C-PrO)-Ad-Ph-OEOM EE (Compound 11a)

The product was prepared in the same fashion as in compound 14a, by refluxing the mixture of (Br-EtO)-Ad-Ph-OEOM EE 30 (1.27 g, 2.8 mmole) and dimethyl malonate carbanion sodium salt, generated from dimethyl malonate (1.93 ml, 16.8 mmole, 6 equiv.) and 4.37 M MeONa in MeOH (3.85 ml, 16.8 mmole, 6 equiv.), in 18 ml of MeOH for 5 hours. After workup and silica gel purification, 1.21 g (85.6%) of 11a as a colorless oil was obtained.
IR (CHCl₃): 3035, 3015, 2985, 2934, 2858, 1735, 1572-1600, 1440, 1265, 1158, 1100, 1084, 1020, 994, 978 cm⁻¹.

$^1$H NMR (400 MHz, CDCl₃): δ 7.23-7.30 (m, 1H), 6.96-7.03 (m, 2H), 6.91-6.97 (m, 1H), 5.23 (s, 2H), 3.77 (s, 3H), 3.75 (q, J=7.2 Hz, 2H), 3.74 (s, 3H), 3.61 (t, J=7.2 Hz, 1H), 3.46 (t, J=5.9 Hz, 2H), 3.44 (br. s, 1H), 3.30 (s, 3H), 2.82 (br. s, 1H), 2.24 (br. s, 1H), 2.11-2.17 (m, 2H), 1.58-1.92 (m, 10H), 1.24 (t, J=7.6 Hz, 3H).

Example 34

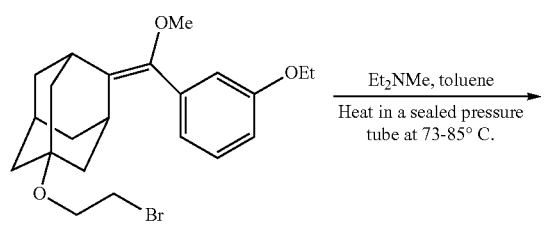

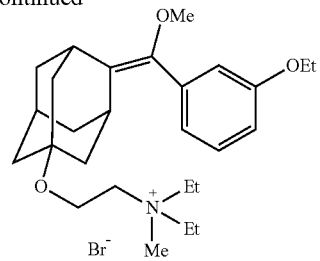

Q⁺-Amino-Ad-Ph-OEt EE (Compound 12a)

A mixture of the (Br-EtO)-Ad-Ph-OEt EE 29 (512.7 mg, 1.2 mmole) and diethylmethylamine (0.75 ml, 6.1 mmole, 5 equiv.) in 5 ml of toluene was placed in a sealed pressure tube. No reaction was detected by TLC after 71 hours of stirring at room temperature. An additional 1.5 ml of diethylmethylamine (12.2 mmole, 10 equiv.) was added, the reaction vessel was heated in an oil bath at 75-83° C. for 48 hours. TLC showed that nearly all of the starting material was converted to the polar product. The reaction mixture was concentrated and purified by silica gel chromatography, eluting with 0-10% MeOH in CH₂Cl₂, to give 560 mg (90.5%) of the product 12a as an orange gum.
IR (CHCl₃): 3620, 3380, 2992, 2932, 2858, 1597, 1578, 1430-1478, 1286, 1240, 1177, 1100, 1015, 975 cm⁻¹.

$^1$H NMR (400 MHz, CDCl₃): δ 7.22-7.33 (m, 1H), 6.80-6.90 (m, 3H), 4.01-4.09 (m, 2H), 3.81-3.93 (m, 4H), 3.60-3.75 (m, 3 or 4H?), 3.48 (br. s, 3H?), 3.27-3.35 (m, 5H?), 2.83 (br. s, 1H), 2.29 (br. s, 1H), 1.59-1.91 (m, 10H), 1.35-1.48 (m, 9H). Due to the complexity of the spectrum, and the presence of impurities, the integrals of some superimposed peaks cannot be definitively assigned.

Example 35

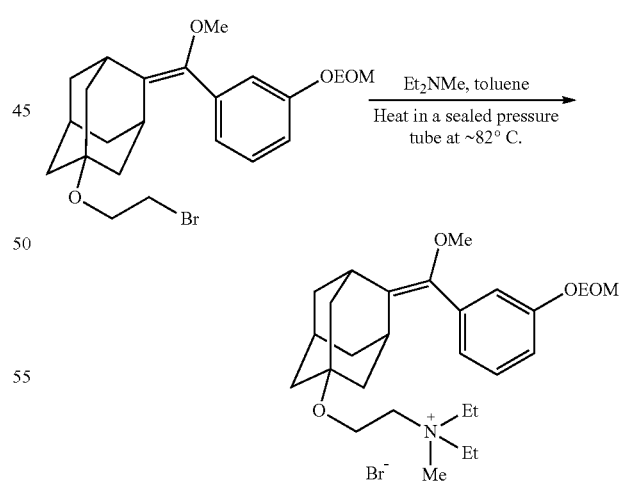

Q⁺-Amino-Ad-Ph-OEOM EE (Compound 13a)

A mixture of the (Br-EtO)-Ad-Ph-OEOM EE 30 (483.4 mg, 1.1 mmole) and diethylmethylamine (1.3 ml, 11 mmole, 10 equiv.) in 5 ml of toluene in a sealed pressure tube was heated at ~82° C. for 95 hours. The reaction mixture was concentrated and purified by silica gel chromatography, eluting with 5-20% MeOH in $CH_2Cl_2$, to give 312.5 mg (54.2%) of the product 13a as a light yellow gum.

IR ($CHCl_3$): 3680, 3380, 2930, 2858, 1600, 1580, 1460, 1393, 1236, 1160, 1100, 1080, 1019, 976 $cm^{-1}$.

$^1$H NMR (400 MHz, $CDCl_3$): δ 7.25-7.29 (m, 1H), 6.98-7.04 (m, 1H), 6.95-6.99 (m, 1H), 6.91-6.96 (m, 1H), 5.24 (s, 2H), 3.81-3.93 (m, 4H), 3.75 (q, J=7 Hz), 3.61-3.72 (m, 4H), 3.48 (br. s, 1H), 3.31 (s, 3H), 3.30 (s, 3H), 2.85 (br. s, 1H), 2.29 (br. s, 1H), 1.59-1.91 (m, 10H), 1.40 (t, J=7 Hz, 6H), 1.23 (t, J=7 Hz, 3H).

Photooxygenation of the Enol Ethers.

The general reaction was carried out by irradiation of a mixture of the Enol Ether and 20-30 drops of the sensitizer Methylene Blue stock solution (2 mg/ml MeOH) in $CHCl_3$ with a 400 W high-pressure sodium vapor lamp for 30-60 minutes below 10° C., while continuously bubbling oxygen through the solution. TLC and UV spectrum were used to monitor the reaction, i.e., from UV spectra, the maximum absorptions of the product shifted from ~257 nm to 280 nm as the reaction proceeded. After the reaction was complete, the reaction mixture was concentrated by a rotary evaporator below 20° C. and purified by silica gel chromatography, eluting with the appropriate solvent system to give the dioxetane as a yellow gum. The charged dioxetanes, such as $Q^+$-amino compounds 12-13, and bis-sodium carboxylate salts 14-15, were further purified by reverse-phase prep HPLC.

Example 36

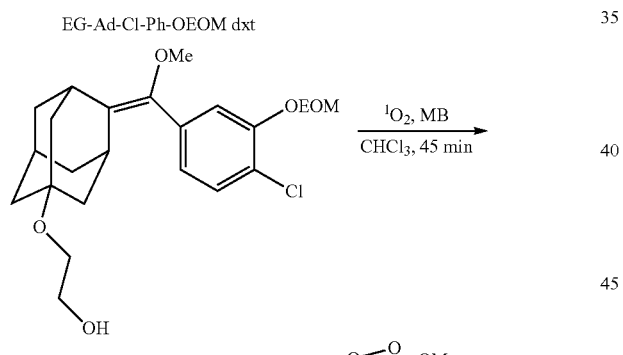

EG-Ad-Cl-Ph-OEOM dxt (Compound 8)

A Solution of EG-Ad-Cl-Ph-OEOM-EE 8e (211.3 mg, 0.5 mmole) in 10 ml of $CHCl_3$ was photooxygenated for 45 min. by the general process described above. The UV spectra showed the maximum absorptions of the product shifted from 263.5 nm to 279 nm. The crude product was purified by silica gel chromatography, eluting with 30-40% EtOAc in hexanes, to give 229.1 mg (100%) of the product 8 as an orange gum.

Example 37

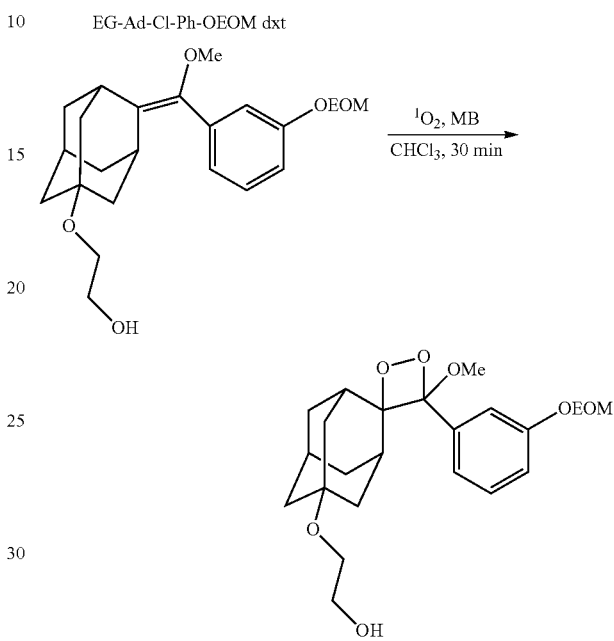

EG-Ad-Ph-OEOM dxt (Compound 31)

A solution of the EG-Ad-Ph-OEOM-EE 27 (333.7 mg, 0.86 mmole) in 12 ml of $CHCl_3$ was photooxygenated for 30 min by the general process described above. The UV spectra showed the maximum absorptions of the product shifted from 258.5 nm to 276.5 nm. The crude product was purified by silica gel chromatography, eluting with 30-40% EtOAc in hexanes, to give 316.7 mg (87.7%) of the product 31 as a yellow gum.

Example 38

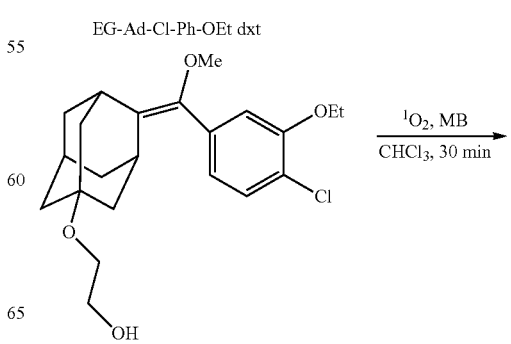

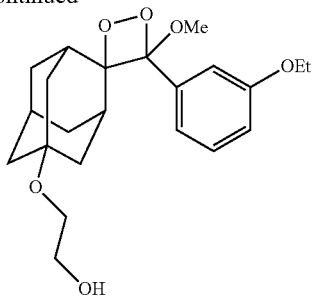

EG-Ad-Ph-OEt dxt (Compound 32)

A solution of the EG-Ad-Ph-OEt-EE 28 (306.2 mg, 0.85 mmole) in 10 ml of CHCl₃ was photooxygenated for 30 min by the general process described above. The UV spectra showed the maximum absorptions of the product shifted from 258.5 nm to 280.5 nm. The crude product was purified by silica gel chromatography, eluting with 20-30% acetone in hexanes, to give 337.1 mg (100%) of the product 32 as a yellow gum.

Example 39

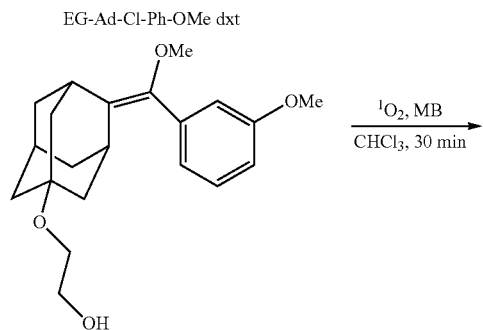

EG-Ad-Ph-OMe dxt (Compound 9)

A solution of the EG-Ad-Ph-OMe-EE 9a (289.2 mg, 0.84 mmole) in 12 ml of CHCl₃ was photooxygenated for 30 min by the general process described above. The UV spectra showed the maximum absorptions of the product shifted from 258.5 nm to 280.0 nm. The crude product was purified by silica gel chromatography, eluting with 20-30% acetone in hexanes, to give 322.3 mg (100%) of the product 9 as a yellow gum.

Example 40

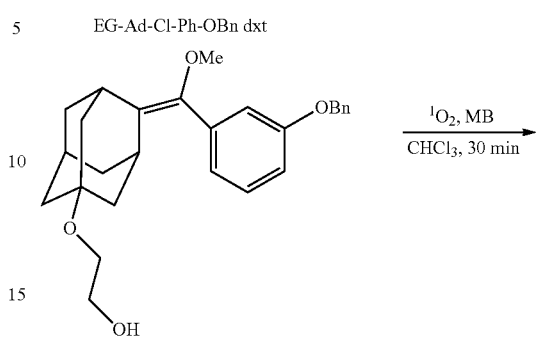

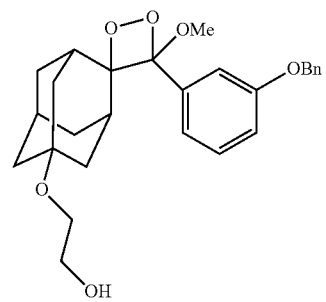

EG-Ad-Ph-OBn dxt (Compound 10)

A solution of the EG-Ad-Ph-OBn-EE 10a (568.1 mg, 1.35 mmole) in 15 ml of CHCl₃ was photooxygenated for 30 min by the general process described above. The UV spectra showed the maximum absorptions of the product shifted from 259 nm to 279 nm. The crude product was purified by silica gel chromatography, eluting with 20-30% acetone in hexanes, to give 588.9 mg (96.3%) of the product 10 as a yellow gum.

Example 41

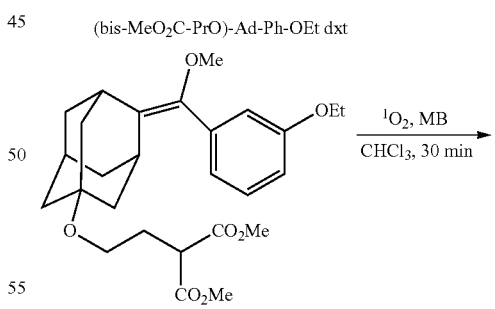

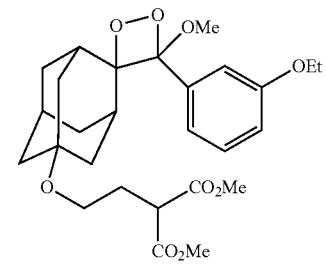

(bis-MeO₂C-PrO)-Ad-Ph-OEt dxt (Compound 14b)

A solution of the (bis-MeO₂C-PrO)-Ad-Ph-OEt EE 14a (457 mg, 0.97 mmole) in 12 ml of CHCl₃ was photooxygenated for 30 min by the general process described above. The UV spectra showed the maximum absorptions of the product shifted from 258.5 nm to 280 nm. The crude product was purified by silica gel chromatography, eluting with 20-30% acetone in hexanes, to give 525.6 mg (100%) of the product 14b as a yellow gum.

Example 42

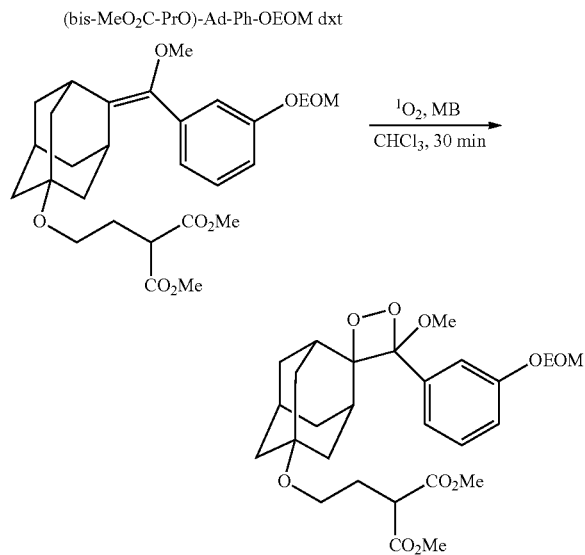

(bis-MeO₂C-PrO)-Ad-Ph-OEOM dxt (Compound H)

A solution of the (bis-MeO₂C-PrO)-Ad-Ph-OEOM EE 11a (490.2 mg, 0.98 mmole) in 12 ml of CHCl₃ was photooxygenated for 30 min by the general process described above. The UV spectra showed the maximum absorption of the product shifted from 259 nm to 276.5 nm. The crude product was purified by silica gel chromatography, eluting with 20-30% acetone in hexanes, to give 579.5 mg (100%) of the product 11 as a yellow gum.

Example 43

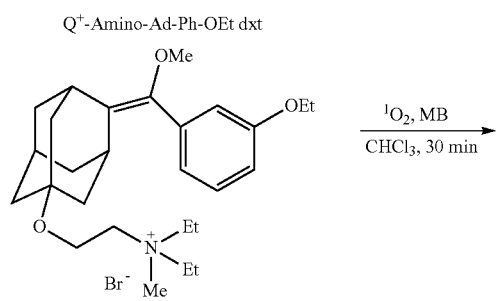

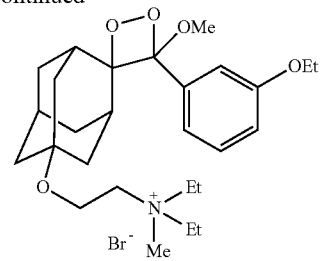

Q⁺-Amino-Ad-Ph-OEt dxt (Compound 12)

A solution of the Q⁺-Amino-Ad-Ph-OEt EE 12a (479.8 mg, 0.94 mmole) in 12 ml of CHCl₃ was photooxygenated for 30 min by the general process described above. The UV spectra showed the maximum absorptions of the product shifted from 257 nm to 280.5 nm. The reaction mixture was concentrated by a rotary evaporator at below 20° C. to form a violet gum. Analytic reverse-phase HPLC using CH₃CN-0.1% NaHCO₃ solution gradient showed the crude product had a broad peak at 14.98 minutes with a tail at 18.33 minutes. The crude product was purified by one-inch reverse-phase prep HPLC, eluting with an acetonitrile-water gradient. Those product fractions were pooled and lyophilized, to give 328.4 mg (64.6%) of 12 as a light yellow powder.

Example 44

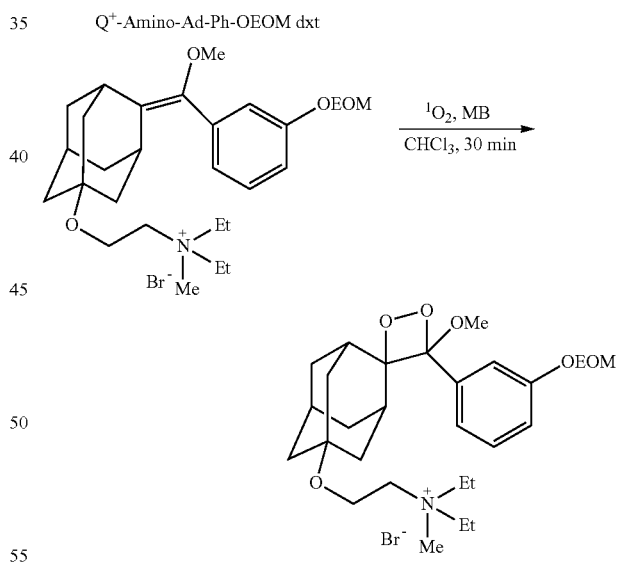

Q⁺-Amino-Ad-Ph-OEOM dxt (Compound 13)

A solution of the Q⁺-Amino-Ad-Ph-OEt EE 13a (262.6 mg, 0.49 mmole) in 12 ml of CHCl₃ was photooxygenated for 30 min by the general process described above. The UV spectra showed the maximum absorptions of the product shifted from 258 nm to 276.5 nm. The reaction mixture was concentrated by a rotary evaporator at below 20° C. to form a violet gum. The crude product was purified by one-inch reverse-phase prep HPLC, eluting with an acetonitrile-water gradient. Those product fractions were pooled and lyophilized, to give 162.2 mg (58.3%) of a light brown powder 13.

Example 45 bis-CO$_2$Na-Ad-Ph-OEt dxt

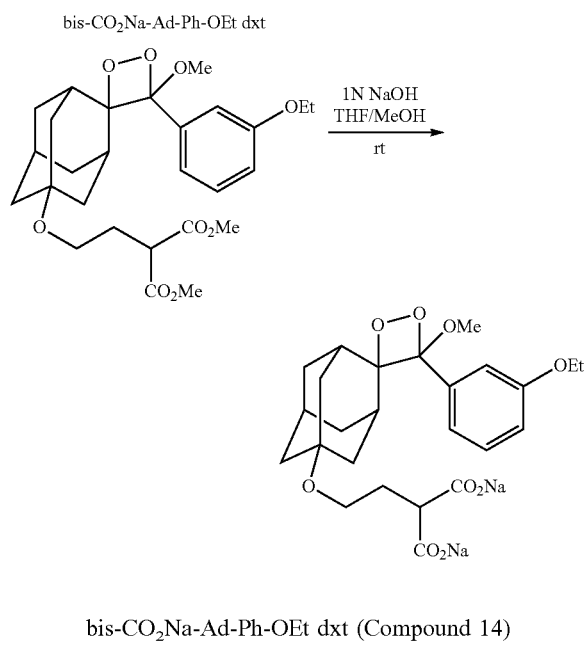

bis-CO$_2$Na-Ad-Ph-OEt dxt (Compound 14)

To a mixture of (bis-MeO$_2$C-PrO)-Ad-Ph-OEt EE 14b (446.3 mg, 0.88 mmole) in 2 ml each of THF and MeOH, was added 1N NaOH solution (3.5 ml, 3.5 mmole, 2 equiv.) at room temperature. The reaction was monitored by analytical reverse-phase HPLC, eluting with CH$_3$CN-0.1% NaHCO$_3$ solution gradient. As the reaction proceeding, the integrals of the fully saponified dioxane peaks (two dioxetane isomers) at 5.1 and 6.2 min. were increasing; the partially saponified intermediate peaks at 10.4 and 10.6 min were decreasing. After multiple additions of NaOH solution (a total of 6.5 ml, 3.7 equiv.) over 3.5 hours, the reaction was completed. Powdered NaHCO$_3$ (672 mg) was added to the reaction and the solution was diluted with 30% CH$_3$CN in water. After filtration, the filtrate was divided into two injections for one-inch reverse-phase prep HPLC purification. The column was eluted with an acetonitrile-water gradient. Those product fractions were pooled and lyophilized, to give 316.2 mg (68.7%) of 14 as an off-white powder.

Example 46 bis-CO$_2$Na-Ad-Ph-OEOM dxt

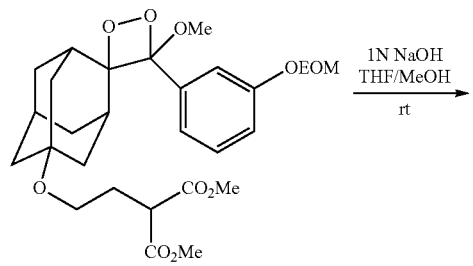

-continued

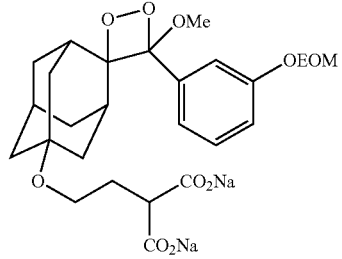

bis-CO$_2$Na-Ad-Ph-OEOM dxt (Compound 15)

The saponification of (bis-MeO$_2$C-PrO)-Ad-Ph-OEOM dxt 11 (495.6 mg, 0.93 mmole) in the mixture of 1N NaOH solution/THF/MeOH at room temperature proceeded similarly to the previous reaction of compound 14. After multiple additions of NaOH solution (a total of 5.6 ml, 5.6 mmole, 3 equiv.) over 3.5 hours, analytical reverse-phase HPLC showed that most of the partially saponified intermediate (a broad peak at 10.5 min) was converted to the desired product (two peaks at 5.6 and 6.4 min.). The reaction was quenched with 588 mg of powdered NaHCO$_3$. The crude product was purified by one-inch reverse-phase prep HPLC, eluting with an acetonitrile-water gradient. Those product fractions were pooled and lyophilized, to give 299.7 mg (58.7%) of 15 as a white powder.

Example 47

Substrate Stock Solutions

Stock solutions of all substrates were prepared at 3 mM to 14 mM in acetonitrile (most substrates), in water, or in acetonitrile/water solution, and stored at −20° C. until use. Details of the stock solutions are provided elsewhere or are known to those skilled in the art.

Example 48

Screening 1, 2 Dioxetanes for Cytochrome P450 Isozyme Activity

CYP450 assays have been developed for screening novel 1,2-dioxetane chemiluminescent substrates for CYP450 reactivity. Screening for the five major isozymes, CYP1A2, CYP2C9, CYP2C19, CYP2D6, and CYP3A4 are described, but the procedure can be used to screen reactivity of other CYP450 isozymes as well. The following is an example of two different screening assay formats. The first (Format A) is a 2-Step Endpoint assay in which the substrate is incubated with the enzyme reaction concoction during which time a phenol dioxetane product, which is stable at neutral pH, accumulates if the dioxetane is a substrate for that enzyme. With the addition of Accelerator (I or II) which increases the assay pH, the phenol dioxetane releases a hydrogen to generate the phenolate dioxetane which rapidly breaks down to an emitter at the excited state which then gives off light with decay indicating enzyme activity. Polymeric enhancer in the Accelerator improves detection sensitivity. In the second assay format (Format B), 1,2-dioxetanes having certain backbones are screened in a real time kinetic assay. In this assay format, the assay is a performed at a pH that allows for the product phenol dioxetane to break down after formation due to its lower pKa. BSA is included in the assay to enhance light emission.

Both assays formats are performed using conditions to favor enzyme activity detection including substrate concentrations predicted to be above $K_m$ and non-limiting enzyme concentrations. Assays use recombinant human (rh) CYP450 isozymes (final [5 to 20 nM]), NADPH Regeneration System (final [1×]) and Potassium Phosphate Buffer prepared in a 2× Master Mix. 50 µL of the Master Mix is added to the wells of a 96-well plate. 40 uL of water (Format A) or 0.25% fatty acid-free BSA (Format B) is added the rows of the plate containing the Master Mix. The reaction is started by addition of 10 µL of a 10× NADP+ (nicotinamide adenine dinucleotide phosphate) and Test Dioxetane (final [30 µM]) mix to all wells. For Format A, the assay is allowed to incubate for 25 minutes at 25° C., after which 100 µL of Accelerator II is injected (via luminometer) into the assay wells and is read for 1 second, with a 2 second delay. For Format B, the assay is read continuously using a luminometer, generally using 2 second integration taken at 3 minute intervals.

Assay Format A: Two-Step Endpoint Assay

Materials:

rhCytochrome P450 Isozymes:
    CYP3A4 (BD/Gentest, Cat #456202) (or other vendor)
    CYP2C19 (BD/Gentest, Cat #456259) (or other vendor)
    CYP2C9 (BD/Gentest, Cat #456258) (or other vendor)
    CYP2D6 (BD/Gentest, Cat #456217) (or other vendor)
    CYP1A2 (BD/Gentest, Cat #456203) (or other vendor)

Figure 8:
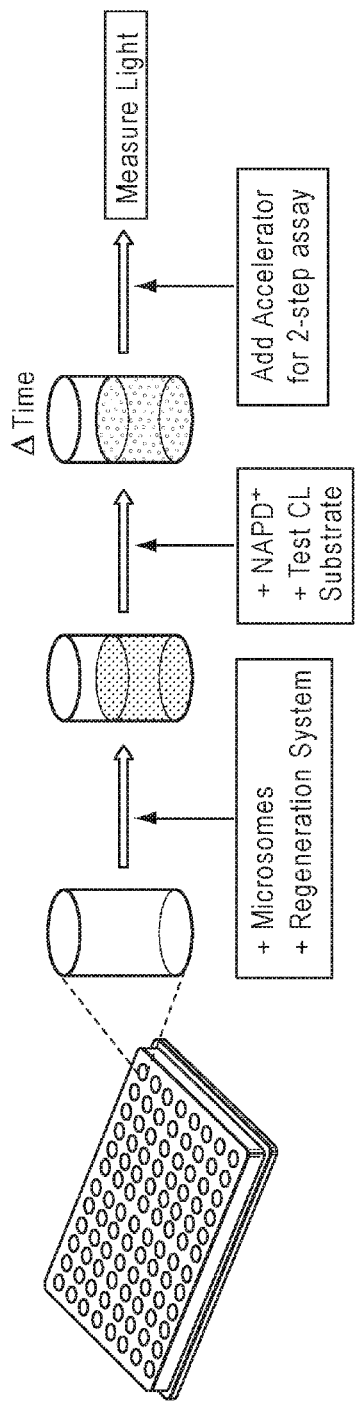
FIG. 8 shows a protocol overview of Assay Format A: Two-Step Endpoint Assay (see, Example 48). Figure is adapted from Wienkers & Heath, Nature Reviews in Drug Discovery, 2005.

200 mM Potassium Phosphate Buffer, pH 7.4
100 mM Potassium Phosphate Buffer, pH 7.4
100× NADP+
    (10 mM NADP+ in 100 mM Potassium phosphate buffer, pH 7.4)
100× Regeneration System
    (333 mM Glucose-6-phosphate, 30 Units/mL Glucose-6-phosphate dehydrogenase in 100 mM Potassium Phosphate Buffer, pH 7.4)
1,2-Dioxetane Test Substrates (in 100% Acetonitrile, water, or acetonitrile/water mixture)
96 well white microplate
Accelerator II Protocol Overview: (See, FIG. 8).

Assay Set-Up:

| 2x Master Mix | 50 µL |
|---|---|

Contains:
2× Regeneration System: from 100× stock is 333 mM Glucose-6-phosphate, 30 Units/mL Glucose-6-phosphate dehydrogenase in 100 mM Potassium Phosphate Buffer, pH 7.4
Desired P450 Isozyme

| H$_2$0 | 40 µL |
|---|---|
| 10x NADP+/Test Substrate Mix | 10 µL |

Contains:
NADP+: 100× stock is 10 mM NADP+ in 100 mM Potassium Phosphate Buffer, pH 7.4
300 µM Test 1,2-Dioxetane Substrate Assay Procedure:
1. Thaw all reagents on ice, except substrates: warm-up to RT under aluminum foil (light sensitive)
2. Prepare 2× Master Mix in 2× reaction buffer (keep on ice). (Makes enough for 125 wells).

| Isozyme | 2 concentration | Final (1X) concentration |
|---|---|---|
| CYP3A4 | 20 nM | 10 nM |
| CYP2C19 | 20 nM | 10 nM |
| CYP2C9 | 40 nM | 20 nM |
| CYP2D6 | 40 nM | 20 nM |
| CYP1A2 | 20 nM | 10 nM |

100× Regeneration System: 2× (final=1×)
Buffer: Bring to 6.250 ml (6250 µl) final volume.

| Isozyme | 2xBuffer | 1xBuffer |
|---|---|---|
| CYP3A4 | 200 mM Potassium Phosphate, pH 7.4 | 100 mM Potassium Phosphate, pH 7.4 |
| CYP2C19 | 100 mM Potassium Phosphate, pH 7.4 | 50 mM Potassium Phosphate, pH 7.4 |
| CYP2C9 | 100 mM Potassium Phosphate, pH 7.4 | 50 mM Potassium Phosphate, pH 7.4 |
| CYP2D6 | 200 mM Potassium Phosphate, pH 7.4 | 100 mM Potassium Phosphate, pH 7.4 |
| CYP1A2 | 200 mM Potassium Phosphate, pH 7.4 | 100 mM Potassium Phosphate, pH 7.4 |

3. Add 50 µL of the appropriate 2× Master Mix to the appropriate wells of the plate
4. Add 40 µL of sterile water (H$_2$O) to each well of the plate
5. Cover plate with plate sealer and let the assay wells equilibrate to 25° C. or room temperature for a few minutes while you prepare the 10×NADP+/Substrate Mixtures.
6. Prepare 10× NADP+/Substrate Mixture immediately before use (light sensitive!)

Test Substrate:

| Substrate | *Stock solution (in Acetonitrile or other) | 10x concentration | Final (1x) concentration |
|---|---|---|---|
| Test 1,2-Dioxetane | >3 mM | 300 µM | 30 µM |

100× NADP+: 10× (1× final)
H$_2$O: to final volume.
Add substrate by trituration and vortex to allow for maximum substrate solubility in the aqueous mixture.
*The final organic solvent concentration in the assay should be less than 0.1% and preferably much less.

7. Add 10 µL of 10× NADP+/Test Dioxetane to appropriate assay wells.
8. Incubate at 25° C. for 25 to 30 minutes.
9. Inject 100 µL of Accelerator II via injector on luminometer
10. Read for 2 second, with a 1 second delay Assay Format B: Real-Time Kinetic Assay Materials:

rhCytochrome P450 Isozymes:
    CYP3A4 (BD/Gentest, Cat #456202) (or other vendor)
    CYP2C19 (BD/Gentest, Cat #456259) (or other vendor)
    CYP2C9 (BD/Gentest, Cat #456258) (or other vendor)
    CYP2D6 (BD/Gentest, Cat #456217) (or other vendor)
    CYP1A2 (BD/Gentest, Cat #456203) (or other vendor)

200 mM Potassium Phosphate Buffer, pH 7.4 to pH 8
100 mM Potassium Phosphate Buffer, pH 7.4 to pH 8
100× NADP+

Figure 9:
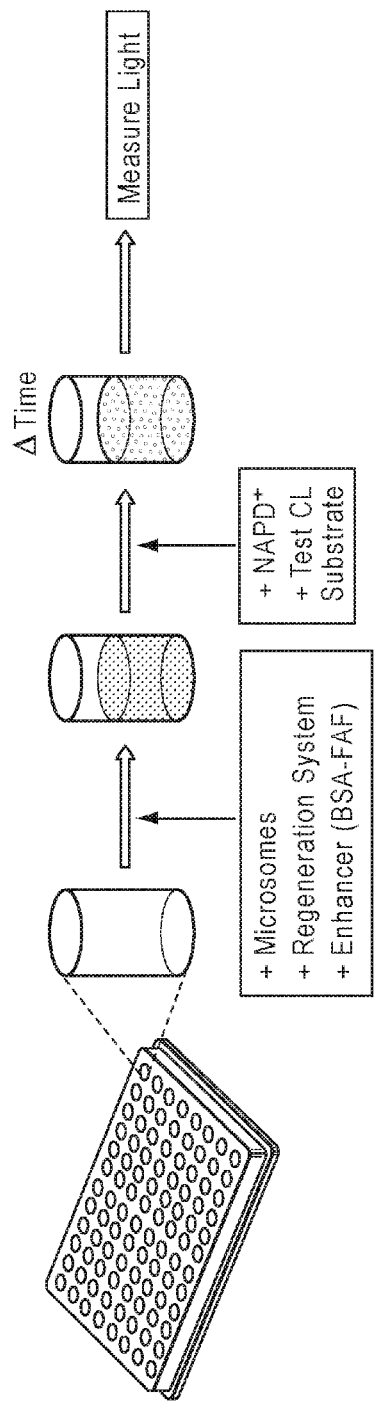
FIG. 9 shows a protocol overview of Cytochrome P450 Isozyme Activity Assay Format B: Real-Time Kinetic Assay (see, Example 48). Figure is adapted from Wienkers & Heath, Nature Reviews in Drug Discovery, 2005.

(10 mM NADP+ in 100 mM Potassium phosphate buffer, pH 7.4)
100× Regeneration System
(333 mM Glucose-6-phosphate, 30 Units/mL Glucose-6-phosphate dehydrogenase in 100 mM Potassium Phosphate Buffer, pH 7.4)
10% BSA-FAF
(Bovine Serum Albumin, fatty acid-free) in 100 mM Potassium Phosphate Buffer, pH 8
1,2-Dioxetane Test Substrates (in 100% Acetonitrile, water, or acetonitrile/water mixture)
96 well white microplate
Protocol Overview: (See, FIG. 9).
Assay Set-Up:

| 2× Master Mix | 50 µL |
|---|---|

Contains:
2× Regeneration System: from 100× stock is 333 mM Glucose-6-phosphate, 30 Units/mL Glucose-6-phosphate dehydrogenase in 100 mM Potassium Phosphate Buffer, pH 7.4
Desired P450 Isozyme

| 2.5× BSA-FAF | 40 µL |
|---|---|
| 10× NADP+/Test Substrate Mix | 10 µL |

Contains:
NADP+: 100× stock is 10 mM NADP+ in 100 mM Potassium Phosphate Buffer, pH 7.4
300 µM Test 1,2-Dioxetane Substrate
Assay Procedure:
1. Thaw all reagents on ice, except substrates: warm-up to RT under aluminum foil (light sensitive)
2. Prepare 2× Master Mix in 2× reaction buffer (keep on ice). (Makes enough for 125 wells).

| Isozyme | 2 concentration | Final (1X) concentration |
|---|---|---|
| CYP3A4 | 20 nM | 10 nM |
| CYP2C19 | 20 nM | 10 nM |
| CYP2C9 | 40 nM | 20 nM |
| CYP2D6 | 40 nM | 20 nM |
| CYP1A2 | 20 nM | 10 nM |

100× Regeneration System: 2× (final=1×)
Buffer: Bring to 6.250 ml (6250 µl) final volume.

| Isozyme | 2×Buffer | 1×Buffer |
|---|---|---|
| CYP3A4 | 200 mM Potassium Phosphate, pH 8 | 100 mM Potassium Phosphate, pH 8 |
| CYP2C19 | 100 mM Potassium Phosphate, pH 8 | 50 mM Potassium Phosphate, pH 8 |
| CYP2C9 | 100 mM Potassium Phosphate, pH 8 | 50 mM Potassium Phosphate, pH 8 |
| CYP2D6 | 200 mM Potassium Phosphate, pH 8 | 100 mM Potassium Phosphate, pH 8 |
| CYP1A2 | 200 mM Potassium Phosphate, pH 8 | 100 mM Potassium Phosphate, pH 8 |

3. Add 50 µL of 2× Master Mix to each well of the plate
4. Prepare 2.5× BSA-FAF (0.625%) in water.

| Enhancer | *Stock solution (in water) | 2.5× concentration | Final (1×) concentration |
|---|---|---|---|
| BSA-FAF | 10% | 0.625% | 0.250% |

5. Add 40 µL of 2.5× BSA-FAF (0.625%) to each well of the plate
6. Cover plate with plate sealer and let the assay wells equilibrate to 25° C. or room temperature for a few minutes while you prepare the 10×NADP+/Substrate Mixtures.
7. Prepare 10× NADP+/Substrate Mixture immediately before use (light sensitive!)
Test Substrate:

| Substrate | *Stock solution (in Acetonitrile or other) | 10× concentration | Final (1×) concentration |
|---|---|---|---|
| Test 1,2-Dioxetane | >3 mM | 300 µM | 30 µM |

100× NADP+: 10× (1× final)
H$_2$O: to final volume.
Add substrate by trituration and vortex to allow for maximum substrate solubility in the aqueous mixture.
*The final organic solvent concentration in the assay should be less than 0.1% and preferably much less.
7. Add 10 µL of 10× NADP+/Test Dioxetane to appropriate assay wells to start the reaction.
8. Immediately place in a luminometer with temperature control at 25 C.
10. Measure luminescence every 2 or 3 minutes for 30 to 90 minutes (Kinetic mode) or read at a set time after incubation (Endpoint mode). Read plate for 2 second with integration.

Example 49

Screening 1,2-Dioxetane Chemiluminescent Substrates for Isozyme Specificity

Cytochrome P450 assays have been developed to determine the isozyme specificity of novel 1,2-dioxetane chemiluminescent CYP450 substrates. In these assays, a 1,2-dioxetane substrate that has been determined to be a good substrate for a specific CYP450 isozyme is screened against individual recombinant (human or other) CYP450 isozymes. The protocol follows the 2-Step Endpoint assay format described above (Example 2, Format 1). The assay can be performed using either assay conditions that mimic an inhibition assay (Example 1) using substrate concentrations near the known or predicted K$_m$ of the substrate with its known isozyme, or at concentrations designed for more sensitive enzyme detection which is generally above the K$_m$. Assays can be performed in several different ways depending on the desired information. If one is seeking to find out if the dioxetane is a substrate for different CYP450 isozymes at the specific isozyme's preferred assay conditions, the assays should be performed using the buffer and assay conditions preferred by each specific isozyme (Format 1). If one wants to find out if the dioxetane substrate is selective for a given CYP450 isozyme at that isozyme's preferred assay conditions, the assays should be performed using only the assay conditions of the matched isozyme (Format 2). Assays use recombinant human (rh) CYP450 isozymes (final [5 or 10 nM]), NADPH Regeneration System (final

[1×]) and Potassium Phosphate Buffer prepared in a 2× Master Mix. 50 μL of the Master Mix is added to the wells of a 96-well plate. 40 μL of water is added the rows of the plate containing the Master Mix. The reaction is started by addition of 10 μL of a 10× NADP+ (nicotinamide adenine dinucleotide phosphate) and 1,2-Dioxetane Substrate (final [1 to 10 μM]) mix to assay wells. The assays are incubated for either 25 min (Format 1) or at the specific assay time (see Example 48, Format 2).

Figure 3A:
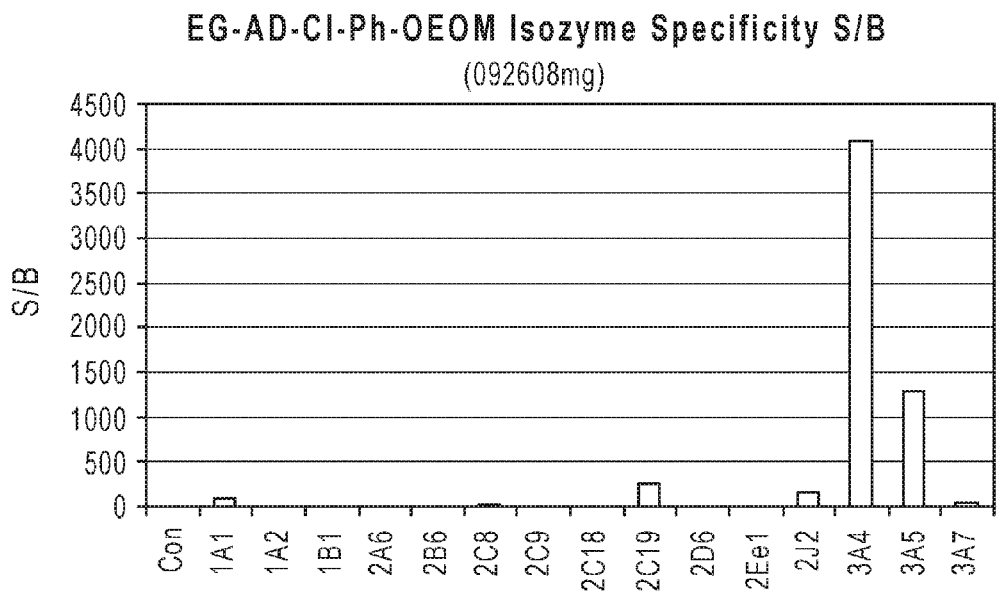
FIG. 3A and FIG. 3B compare CYP450 isozyme specificity of 1,2-dioxetane substrate EG-AD-Cl-Ph-OEOM in recombinant human microsomes (rhCYPs) and human liver microsomes.
Figure 4A:
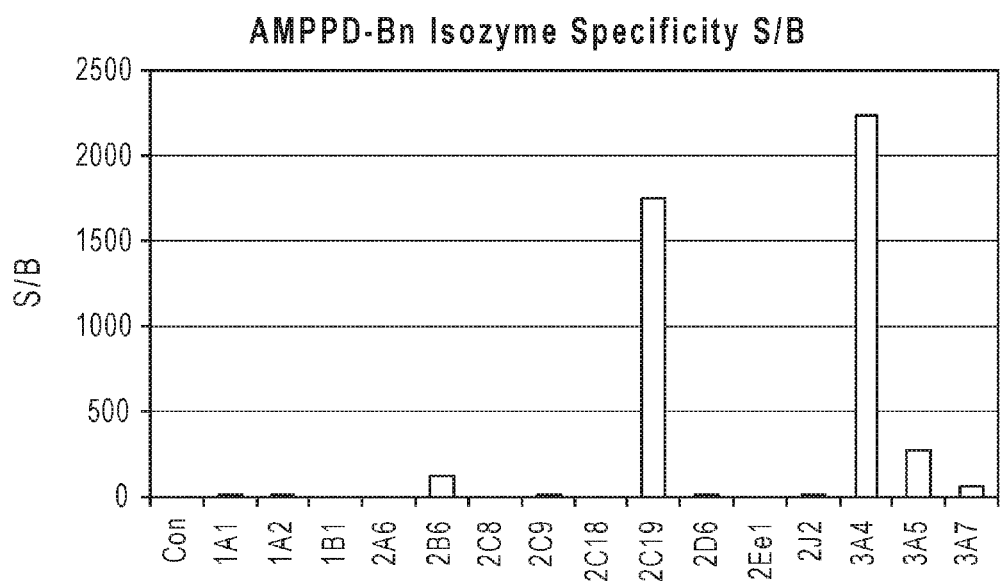
FIG. 4A and FIG. 4B compare CYP450 isozyme specificity of 1,2-dioxetane substrate AMPPD-Bn in recombinant human microsomes (rhCYPs) and human liver microsomes.
Figure 5A:
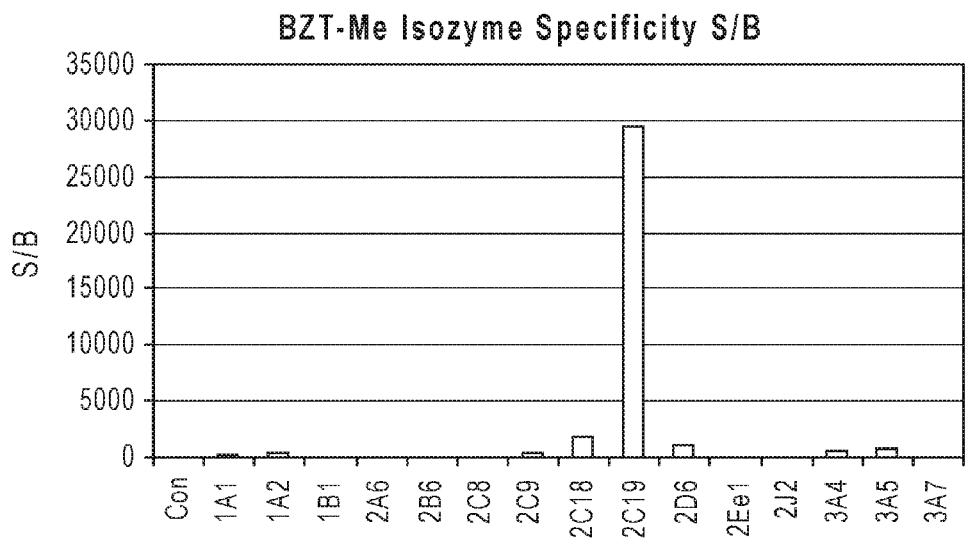
FIG. 5A and FIG. 5B compare CYP450 isozyme specificity of 1,2-dioxetane substrate BZT-Me in recombinant human microsomes (rhCYPs) and human liver microsomes.

Assay Format C: Assay Using Isozyme-Specific Conditions (See FIGS. 3A, 4A, and 5A.)

Figure 10:
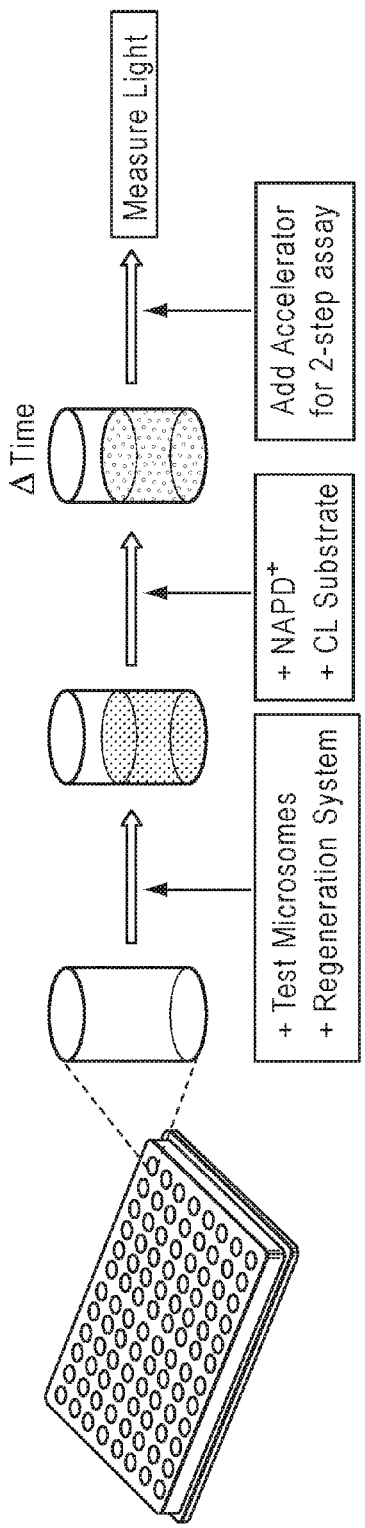
FIG. 10 shows a protocol overview of Assay Format C: Assay using Isozyme-specific conditions (see, Example 49). Figure is adapted from Wienkers & Heath, Nature Reviews in Drug Discovery, 2005.

Materials:
rhCytochrome P450 Isozymes:
 CYP3A4 (BD/Gentest, Cat #456202) (or other vendor)
 CYP2C19 (BD/Gentest, Cat #456259) (or other vendor)
 CYP2C9 (BD/Gentest, Cat #456258) (or other vendor)
 CYP2D6 (BD/Gentest, Cat #456217) (or other vendor)
 CYP1A2 (BD/Gentest, Cat #456203) (or other vendor)
 Or Other CYP450 recombinant isozymes
200 mM Potassium Phosphate Buffer, pH 7.4
100 mM Potassium Phosphate Buffer, pH 7.4
100× NADP+
 (10 mM NADP+ in 100 mM Potassium phosphate buffer, pH 7.4)
100× Regeneration System
 (333 mM Glucose-6-phosphate, 30 Units/mL Glucose-6-phosphate dehydrogenase in 100 mM Potassium Phosphate Buffer, pH 7.4)
1,2-Dioxetane Substrates (in 100% Acetonitrile, water, or acetonitrile/water mixture)
96 well white microplate
Accelerator II Protocol Overview: (See, FIG. 10).
Assay Set-Up:

| 2× Master Mix | 50 μL |
|---|---|

Contains:
2× Regeneration System: from 100× stock is 333 mM Glucose-6-phosphate, 30 Units/mL Glucose-6-phosphate dehydrogenase in 100 mM Potassium Phosphate Buffer, pH 7.4
Desired P450 Isozyme

| H$_2$0 | 40 μL |
|---|---|
| 10× NADP+/Test Substrate Mix | 10 μL |

Contains:
NADP+: 100× stock is 10 mM NADP+ in 100 mM Potassium Phosphate Buffer, pH 7.4
100 μM Known 1,2-Dioxetane Substrate Assay Procedure:
1. Thaw all reagents on ice, except substrates: warm-up to RT under aluminum foil (light sensitive)
2. Prepare 2× Master Mixes in 2× reaction buffer (keep on ice).

| Isozyme | 2 concentration | Final (1X) concentration |
|---|---|---|
| CYP3A4 | 10 nM | 5 nM |
| CYP2C19 | 10 nM | 5 nM |
| CYP2C9 | 20 nM | 10 nM |
| CYP2D6 | 20 nM | 10 nM |
| CYP1A2 | 10 nM | 5 nM |
| Other CYP | 10 nM | 5 nM |

100× Regeneration System: 2× (final=1×)
Buffer: Bring to final volume.

| Isozyme | 2xBuffer | 1xBuffer |
|---|---|---|
| CYP3A4 | 200 mM Potassium Phosphate, pH 7.4 | 100 mM Potassium Phosphate, pH 7.4 |
| CYP2C19 | 100 mM Potassium Phosphate, pH 7.4 | 50 mM Potassium Phosphate, pH 7.4 |
| CYP2C9 | 100 mM Potassium Phosphate, pH 7.4 | 50 mM Potassium Phosphate, pH 7.4 |
| CYP2D6 | 200 mM Potassium Phosphate, pH 7.4 | 100 mM Potassium Phosphate, pH 7.4 |
| CYP1A2 | 200 mM Potassium Phosphate, pH 7.4 | 100 mM Potassium Phosphate, pH 7.4 |
| Other CYP | 2x Preferred Buffer | 1x Preferred Buffer |

3. Add 50 μL of the specific 2× Master Mix to the desired wells
4. Add 40 μL of sterile water (H$_2$O) to each well of the plate
5. Cover plate with plate sealer and let the assay wells equilibrate to 25° C. or room temperature for a few minutes while you prepare the 10×NADP+/Substrate Mixture.
6. Prepare 10× NADP+/Substrate Mixture immediately before use (light sensitive!)

Test Substrate:

| Substrate | *Stock solution (in Acetonitrile or other) | 10x concentration | Final (1x) concentration |
|---|---|---|---|
| 1,2-Dioxetane Substrate | >3 mM | 100 μM | 10 μM |

100× NADP+: 10× (1× final)
H$_2$O: to final volume.
Add substrate by trituration and vortex to allow for maximum substrate solubility in the aqueous mixture.
*The final organic solvent concentration in the assay should be less than 0.1% and preferably much less.

7. Add 10 μL of 10× NADP+/Test Dioxetane to appropriate assay wells.
8. Incubate at 25° C. for 25 to 30 minutes.
9. Inject 100$_m$L of Accelerator II via injector on luminometer
10. Read for 2 second, with a 1 second delay
11. Compare relative RLUs between CYP isozyme wells to determine isozyme-specificity of the substrate.

Example 50

Assay Using Assay-Specific Conditions (Example: CYP2C19 Assay with BZT-Me) (See FIGS. 3B, 4B, and 5B.)

Materials:
rhCytochrome P450 Isozymes:
 CYP3A4 (BD/Gentest, Cat #456202) (or other vendor)
 CYP2C19 (BD/Gentest, Cat #456259) (or other vendor)
 CYP2C9 (BD/Gentest, Cat #456258) (or other vendor)

CYP2D6 (BD/Gentest, Cat #456217) (or other vendor)
CYP1A2 (BD/Gentest, Cat #456203) (or other vendor)
Or Other CYP450 recombinant isozymes
100 mM Potassium Phosphate Buffer, pH 7.4
100× NADP+
   (10 mM NADP+ in 100 mM Potassium phosphate buffer, pH 7.4)
100× Regeneration System
   (333 mM Glucose-6-phosphate, 30 Units/mL Glucose-6-phosphate dehydrogenase in 100 mM Potassium Phosphate Buffer, pH 7.4)
BZT-Me Stock Solution (in 100% Acetonitrile)
96 well white microplate
Accelerator II
Assay Set-Up:

| 2× Master Mix | 50 μL |
|---|---|

Contains:
2× Regeneration System: from 100× stock is 333 mM Glucose-6-phosphate, 30 Units/mL Glucose-6-phosphate dehydrogenase in 100 mM Potassium Phosphate Buffer, pH 7.4
Desired P450 Isozyme

| H$_2$0 | 40 μL |
|---|---|
| 10× NADP+/BZT-Me Mix | 10 μL |

Contains:
NADP+: 100× stock is 10 mM NADP+ in 100 mM Potassium Phosphate Buffer, pH 7.4
10 μM BZT-Me Assay Procedure:
1. Thaw all reagents on ice, except substrates: warm-up to RT under aluminum foil (light sensitive)
2. Prepare 2× Master Mixes in 2× reaction buffer (keep on ice).

| Isozyme | 2 concentration | Final (1X) concentration |
|---|---|---|
| CYP3A4 | 10 nM | 5 nM |
| CYP2C19 | 10 nM | 5 nM |
| CYP2C9 | 10 nM | 5 nM |
| CYP2D6 | 10 nM | 5 nM |
| CYP1A2 | 10 nM | 5 nM |
| Other CYP | 10 nM | 5 nM |

100× Regeneration System: 2× (final=1×)
CYP2C19 preferred Buffer: Bring to final volume.

| Isozyme | 2×Buffer | 1×Buffer |
|---|---|---|
| CYP2C19 | 100 mM Potassium Phosphate, pH 7.4 | 50 mM Potassium Phosphate, pH 7.4 |

3. Add 50 μL of the specific 2× Master Mix to the desired wells
4. Add 40 μL of sterile water (H$_2$O) to each well of the plate
5. Cover plate with plate sealer and let the assay wells equilibrate to 25° C. or room temperature for a few minutes while you prepare the 10×NADP+/Substrate Mixture.
6. Prepare 10× NADP+/Substrate Mixture immediately before use (light sensitive!)

Test Substrate:

| Substrate | * Stock solution (in Acetonitrile) | 10× concentration | Final (1×) concentration |
|---|---|---|---|
| BZT-Me | >3 mM | 10 μM | 1 μM |

100× NADP+: 10× (1× final)
H$_2$O: to final volume.
Add substrate by trituration and vortex to allow for maximum substrate solubility in the aqueous mixture.
*The final organic solvent concentration in the assay should be less than 0.1% and preferably much less.
7. Add 10 μL of 10× NADP+/BZT-Me to each assay well.
8. Incubate at 25° C. for 10 minutes.

| Isozyme/Substrate Pair | Incubation Time |
|---|---|
| CYP2C19/BZT-Me | 10 minutes |

9. Inject 100 μL of Accelerator II via injector on luminometer
10. Read for 2 second, with a 1 second delay
11. Compare relative RLUs between CYP isozyme wells to determine isozyme-specificity of the substrate using the CYP2C19 assay conditions.

Example 51

Figure 6B:
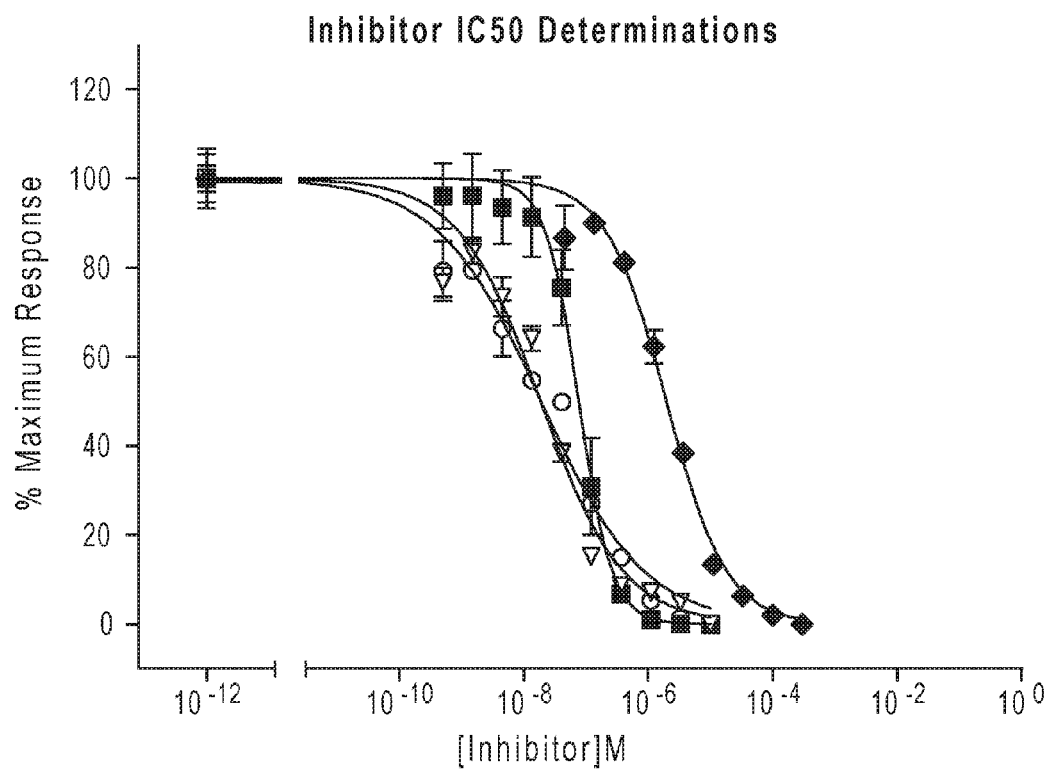
Figure 7A:
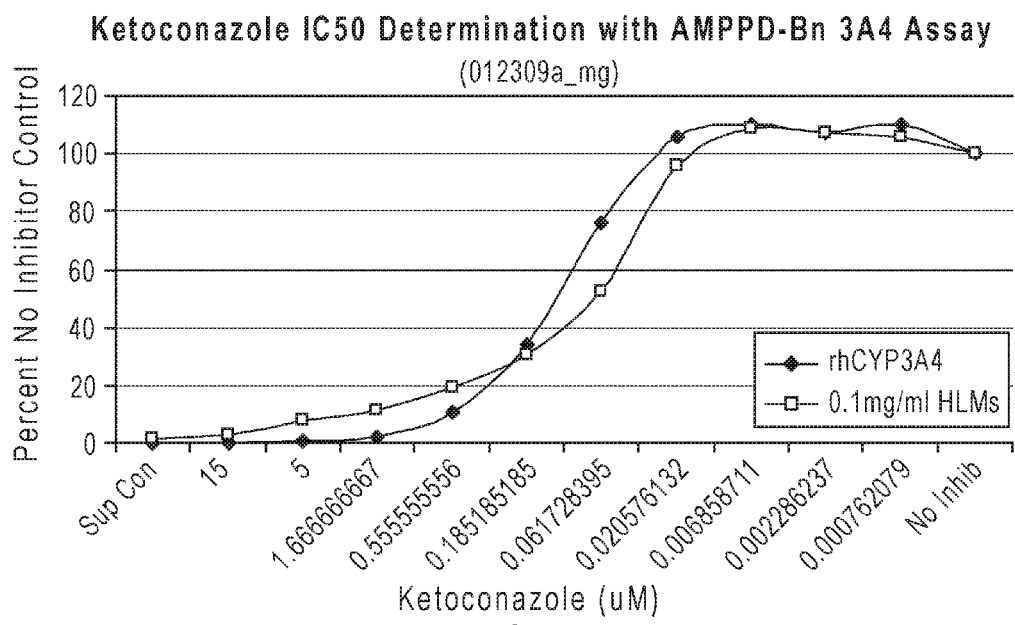
FIG. 7A and FIG. 7B show the $IC_{50}$ determination for ketoconazole in human liver microsomes.
Figure 7B:
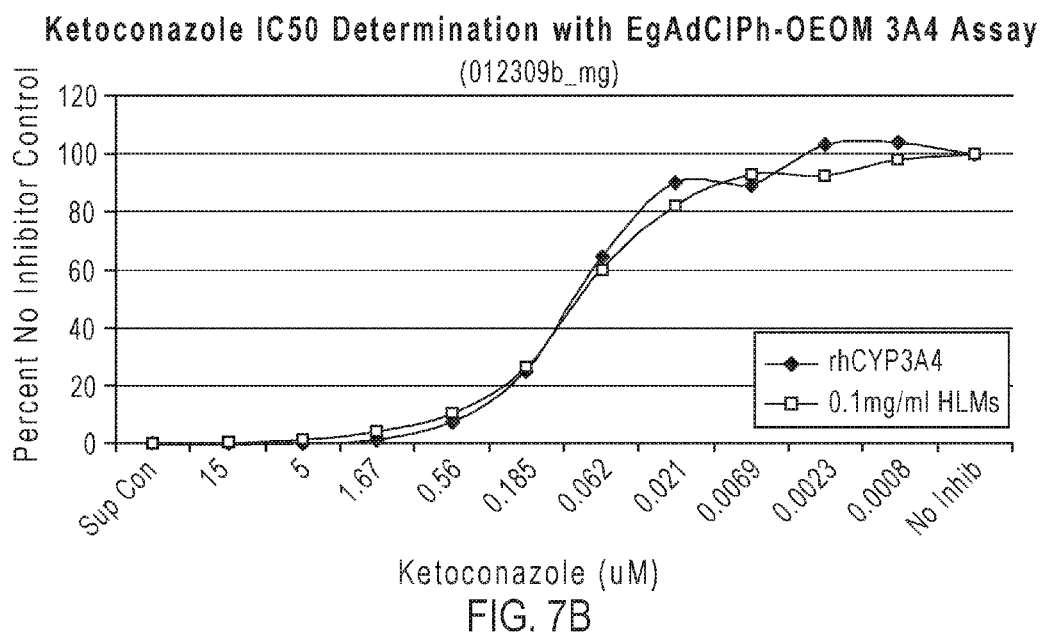

Enzyme Inhibition Assay Example: IC$_{50}$ Determination Using Novel Chemiluminescent Substrates for Specific Cytochrome P450 Isozymes
(See FIGS. 6 and 7.)

CYP450 assays that have been developed for use in a chemiluminescent format utilize novel 1,2-dioxetane chemiluminescent substrates. Five major isozymes are described with their subsequent substrate. The following is an example of an inhibition assay performed with the new substrates and reagents. CYP3A4 (final [5 nM]), Regeneration System (final [1×]) and 100 mM Potassium Phosphate Buffer are prepped as a 2.5× Master Mix. 40 uL of the Master Mix is added to the wells of a 96-well plate. 40 uL of a 2.5× dilution curve of ketoconazole (1:3 dilution, starting at 5 uM (final concentration)) is added the rows of the plate containing the Master Mix. The plate is incubated at 25 degrees Celsius for 30 minutes. After the incubation, 20 uL of a 5× NADP+ (nicotinamide adenine dinucleotide phosphate) and AMPPD-Bn (final [2 uM]) mix to all wells. Incubate for 10 minutes at 25 degrees Celsius. Inject (via luminometer) 100 uL of Accelerator II into selected wells. Read for 1 second, with a 2 second delay.

The IC50 assay can also be performed using non-rhCYP microsome enzyme sources such as human liver microsomes, bodily fluids, tissue (liver, stomach, and the like), tissue microsomal fractions, tissue extracts, cells (hepatocytes, stem cells, or other), cell extracts, tissue or cell supernatants, or other test samples. Crude samples, such as the enzyme sources mentioned above in which the enzyme is not purified, will perform more optimally using dioxetane CYP450 substrates that are isozyme-specific under the assay conditions. The assay can also be performed in 1-step (kinetic or endpoint) mode as described in Example 48.

Figure 11:
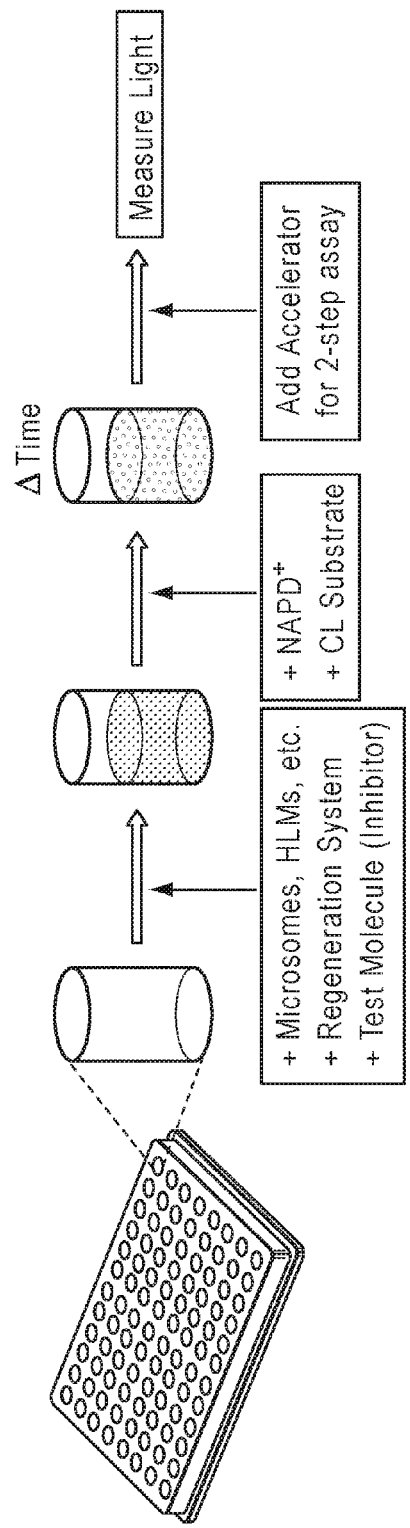
FIG. 11 shows a protocol overview of Enzyme Inhibition Assays (see, Example 51). Figure is adapted from Wienkers & Heath, Nature Reviews in Drug Discovery, 2005.

Protocol Overview: (See, FIG. 11)

| 2.5X Master Mix | 40 uL |
|---|---|

Contains:
Regeneration System: 100× stock is 333 mM Glucose-6-phosphate, 30 Units/mL Glucose-6-phosphate dehydrogenase in 100 mM Potassium Phosphate Buffer, pH 7.4
Desired Isozyme

| 2.5X Inhibitor (contains dilution of Inhibitor) | 40 uL |
|---|---|
| 25° C. Incubation for 30 minutes | |
| 5X NADP+/Substrate Mix | 20 uL |

Contains:
NADP+: 100× stock is 10 mM NADP+ in 100 mM Potassium Phosphate Buffer, pH 7.4
Substrate specific to desired isozyme
25° C. Incubation for 10-15 minute
Materials:
Cytochrome P450 Isozymes:
   CYP3A4 (BD/Gentest, Cat #456202) (or other vendor)
   CYP2C19 (BD/Gentest, Cat #456259) (or other vendor)
   CYP2C9 (BD/Gentest, Cat #456258) (or other vendor)
   CYP2D6 (BD/Gentest, Cat #456217) (or other vendor)
   CYP1A2 (BD/Gentest, Cat #456203) (or other vendor)
100 mM Potassium Phosphate Buffer, pH 7.4
50 mM Potassium Phosphate Buffer, pH 7.4
100× NADP+
   (10 mM NADP+ in 100 mM Potassium phosphate buffer, pH 7.4)
100× Regeneration System
   (333 mM Glucose-6-phosphate, 30 Units/mL Glucose-6-phosphate dehydrogenase in 100 mM Potassium Phosphate Buffer, pH 7.4)
Substrates (in 100% Acetonitrile)
   AMPPD-Bn (CYP3A4)
   BZT-Me (CYP2C9 and CYP2C19)
   Cl-BZT-EOM (CYP2D6)
   Cl-BZT-Me (CYP1A2)
96 well white microplate
Inhibitors:
   Ketoconazole (CYP3A4)
   Miconazole (CYP2C19)
   Sulfaphenazole (CYP2C9)
   Quinidine (CYP2D6)
   Furafylline (CYP1A2)
Accelerator II
Assay Procedure:
Thaw all reagents on ice, except substrates: warm-up to RT under aluminum foil (light sensitive)

1. Prepare 2.5× Master Mix (keep on ice) (makes enough for 125 wells)

| Isozyme | 2.5X concentration | Final (1X) concentration |
|---|---|---|
| CYP3A4 | 12.5 nM | 5 nM |
| CYP2C19 | 12.5 nM | 5 nM |
| CYP2C9 | 25 nM | 10 nM |
| CYP2D6 | 25 nM | 10 nM |
| CYP1A2 | 12.5 nM | 5 nM |

100× Regeneration System: 2.5× (final=1×)
Buffer: q.s. to 5 mL

| Isozyme | Buffer |
|---|---|
| CYP3A4 | 100 mM Potassium Phosphate, pH 7.4 |
| CYP2C19 | 50 mM Potassium Phosphate, pH 7.4 |
| CYP2C9 | 50 mM Potassium Phosphate, pH 7.4 |
| CYP2D6 | 100 mM Potassium Phosphate, pH 7.4 |
| CYP1A2 | 100 mM Potassium Phosphate, pH 7.4 |

2. Prepare 2.5× Inhibitor Dilutions:

| | 2.5X concentration (uM) | final concentration (uM) | Volume of 1 mM (uL) | Volume of Buffer (uL) |
|---|---|---|---|---|
| A | 12.5 | 5 | 15 | 1185 |
| B | 4.17 | 1.67 | 400 of A | 800 |
| C | 1.38 | 0.56 | 400 of B | 800 |
| D | 0.46 | 0.18 | 400 of C | 800 |
| E | 0.15 | 0.06 | 400 of D | 800 |
| F | 0.05 | 0.02 | 400 of E | 800 |
| G | 0.017 | 0.007 | 400 of F | 800 |
| H | 0.006 | 0.002 | 400 of G | 800 |
| I | 0.002 | 0.0007 | 400 of H | 800 |
| J | 0.0006 | 0.0003 | 400 of I | 800 |
| K | 0.0002 | 0.00008 | 400 of J | 800 |
| L | 0 | 0 | 400 of K | 800 |

3. Add 40 uL of 2.5× Master Mix to each well of the plate
4. Add 40 uL of 2.5× Ketoconazole curve to the appropriate wells of the plate:

| | 1 | 2 | 3 | 4 | 5 | 6 | 7 | 8 | 9 | 10 | 11 | 12 |
|---|---|---|---|---|---|---|---|---|---|---|---|---|
| A | 5 uM | 1.67 uM | 0.56 uM | 0.18 uM | 0.06 uM | 0.02 uM | 0.007 uM | 0.002 uM | 0.0007 uM | 0.0003 uM | 0.00008 uM | 0 uM |
| B | | | | | | | | | | | | |
| C | | | | | | | | | | | | |
| D | | | | | | | | | | | | |
| E | | | | | | | | | | | | |
| F | | | | | | | | | | | | |
| G | | | | | | | | | | | | |
| H | | | | | | | | | | | | |

5. Cover plate with plate sealer and incubate at 25° C. for 30 minutes
6. Prepare 5× NADP+/Substrate Mixture immediately before use (light sensitive!)
Substrate:

| Isozyme | Substrate | 5X concentration | Final (1X) concentration |
|---|---|---|---|
| CYP3A4 | AMPPD-Bn | 10 uM | 2 uM |
| CYP2C19 | BZT-Me | 5 uM | 1 uM |
| CYP2C9 | BZT-Me | 10 uM | 2 uM |

| Isozyme | Substrate | 5X concentration | Final (1X) concentration |
|---|---|---|---|
| CYP2D6 | Cl-BZT-EOM | 25 uM | 5 uM |
| CYP1A2 | Cl-BZT-Me | 6.25 uM | 1.25 uM |

100× NADP+: 5× (1× final)
Buffer: q.s. to 3 mL
7. Add 20 uL of 5× NADP+/AMPPD-Bn to each well.
8. Incubate at 25° C. for:

| Isozyme/Substrate Pair | Incubation Time |
|---|---|
| CYP3A4/AMPPD-Bn | 10 minutes |
| CYP2C19/BZT-Me | 10 minutes |
| CYP2C9/BZT-Me | 12 minutes |
| CYP2D6/Cl-BZT-EOM | 15 minutes |
| CYP1A2/Cl-BZT-Me | 15 minutes |

9. Inject 100 uL of Accelerator II via injector on luminometer
10. Read for 2 second, with a 1 second delay
11. Nonlinear Curve Fit Analysis Example 52

Figure 3B:
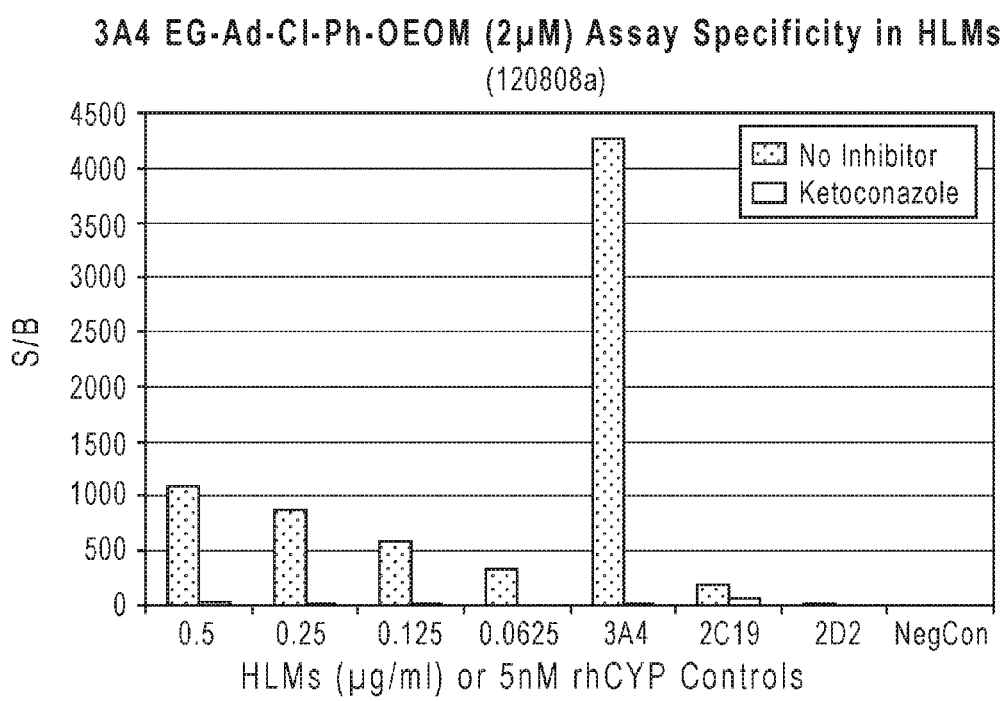
Figure 4B:
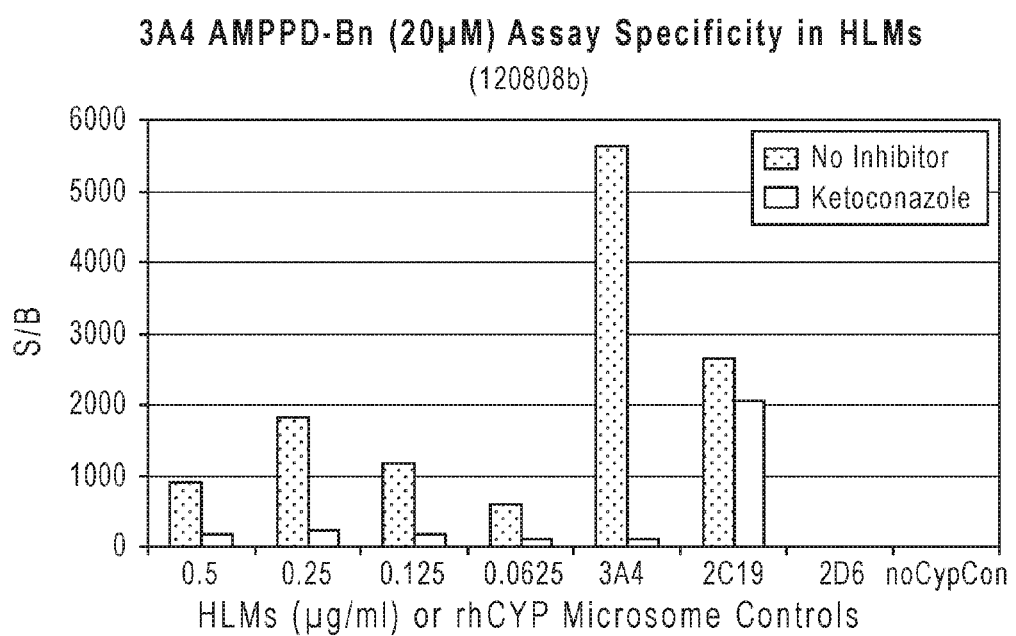
Figure 5B:
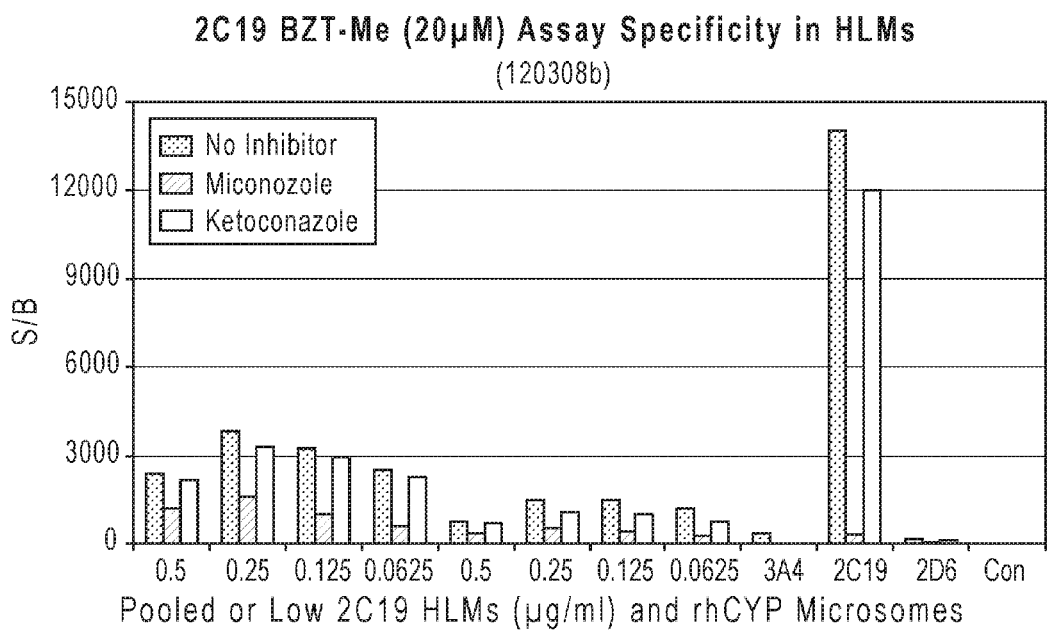

Detecting Cytochrome P450 Isozyme Activity with 1, 2 Dioxetane Chemiluminescent Substrates from Test Samples (See FIGS. 3B, 4B, and 5B.)

Chemiluminescent CYP450 assays using novel 1,2-dioxetane substrates can be used to monitor CYP450 isozyme activity from various samples including recombinant human (or other) CYP450 microsomes, bodily fluids, tissue (liver, stomach, and the like), tissue microsomal fractions, tissue extracts, cells (hepatocytes, stem cells, and the like), cell extracts, tissue or cell supernatants, organism, or other test samples. Such assays are often used for determining CYP450 isozyme induction in response to a drug, other compound, or stimulus (FDA's Draft Guidance for Industry: Drug Interaction Studies—Study Design, Data Analysis, and Implications for Dosing and Labeling" Available online at http://www.fda.gov/cder/biologics/qa.htm), but can also be used to quantify enzyme from various sources. Assays for monitoring CYP450 isozyme activity from crude samples, such as human liver microsomes (HLMs), should ideally be based on substrates that have strong isozyme or isozyme-family selectivity for the CYP450 being addressed. Monitoring isozyme activity from more pure samples, such as rhCYP450X microsomes, does not require that the substrate have the same degree of isozyme selectivity. Several novel 1, 2 dioxetane substrates including BZT-Me (7), Cl-BZT-Me (5), CDP-Star-Me (2), and CDP-Star-Et (3) show a strong specificity for 2C19 and 2C18 isozymes. Substrates EG-Ad-Cl-Ph-OEOM (8), Q+-Amino-Ad-Ph-OEt (12) and Q+-Amino-Ad-Ph-OEOM (13) show strong specificity for the CYP3A family isozymes. Substrates AMPPD-Bn (1) and CDP-Star-Bn (4) also show strong specificity for the CYP3A family isozymes, but show significant activity from CYP2C19 under CYP2C19 assay conditions. Substrates bis-CO$_2$Na-Ad-Ph-OEt dxt (14) and bis-CO$_2$Na-Ad-Ph-OEOM dxt (15) show high specificity for CYP2C8. To ensure that monitored enzyme activity is, indeed, attributed to the enzyme of interest, the isozyme-specific inhibitor negative control should always be performed.

The protocol follows the 2-Step endpoint assay format described in Example 48 (Format A). The assay can be performed using either assay conditions that mimic an inhibition assay (Example 1) using substrate concentrations near the known or predicted $K_m$ of the substrate for its known isozyme, or at concentrations above the $K_m$ for its known isozyme, provided isozyme selectivity is maintained at the higher concentrations. Alternatively, the assay can be performed as in Example 48 (Format B) in 1-step mode. Substrate solubility should also be taken into consideration when working at higher substrate concentrations. Assays use an NADPH Regeneration System (final [1×]) and Potassium Phosphate Buffer prepared in a 2.5× Master Mix. 40 uL of the Master Mix is added to the wells of a 96-well plate. Dilutions of the test sample (microsomal preparation, extract, supernatant, and the like) can be prepared. 40 uL of the test sample is added to the rows of the plate containing the Master Mix. The reaction is started by addition of 20 μL of a 5× NADP+ (nicotinamide adenine dinucleotide phosphate) and 1,2-Dioxetane Substrate (final [1 to 30 μM]) mix to assay wells. The assays are incubated for either 10 to 25 min before addition of Accelerator and reading of luminescent signal on a luminometer. For relative quantification, samples can be compared to a standard curve of known enzyme concentration, bearing in mind that recombinant enzyme can not fully compare to native enzyme.

The enzyme detection or induction assay can also be performed in 1-step (kinetic or endpoint) mode as described in Example 48 when using an appropriate substrate, such as CDP-Star-Bn or EG-Ad-Cl-Ph-OEOM to detect CYP3A4.

Example

Monitoring CYP3A4 Enzyme Activity Using AMPPD-Bn Substrate

Figure 12:
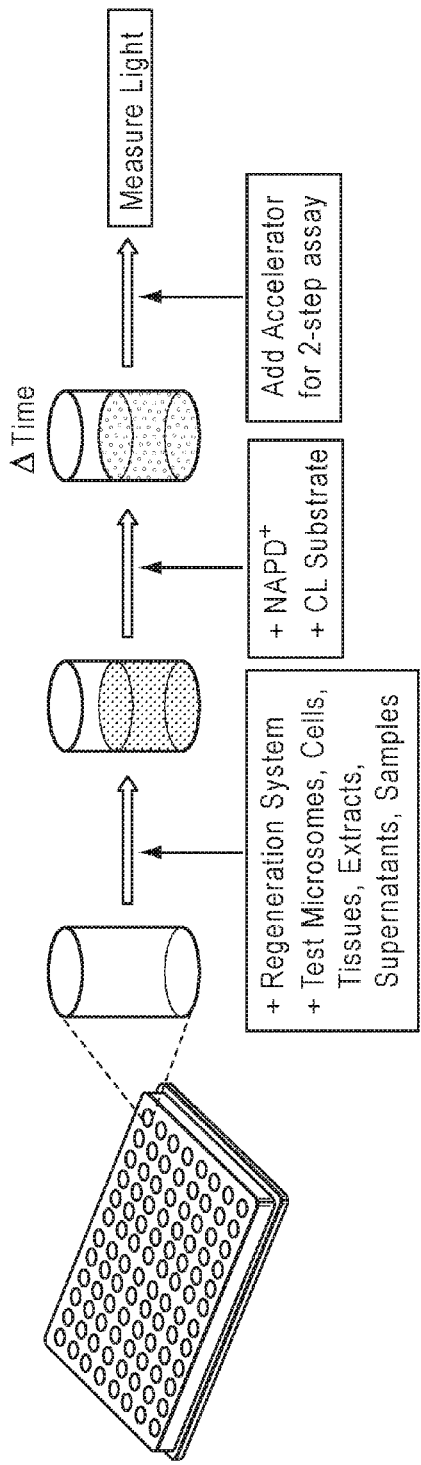
FIG. 12 shows a protocol overview of an assay for monitoring CYP3A4 enzyme activity using AMPPD-Bn substrate (see, Example 52). Figure is adapted from Wienkers & Heath, Nature Reviews in Drug Discovery, 2005.

Materials:
200 mM Potassium Phosphate Buffer, pH 7.4
100× NADP+
  (10 mM NADP+ in 100 mM Potassium phosphate buffer, pH 7.4)
100× Regeneration System
  (333 mM Glucose-6-phosphate, 30 Units/mL Glucose-6-phosphate dehydrogenase in 100 mM Potassium Phosphate Buffer, pH 7.4)
AMPPD-Bn Stock Solution (in 100% Acetonitrile)
Inhibitors:
  Ketoconazole (CYP3A)
  Miconazole (CYP2C19)
96 well white microplate
Accelerator II
Recommended:
rhCytochrome P450 Isozyme for building standard curve and controls for inhibitor selectivity/specificity:
  CYP3A4 (BD/Gentest, Cat #456202) (or other vendor)
  CYP2C19 (BD/Gentest, Cat #456259) (or other vendor)
Protocol Overview: (See, FIG. 12).
Assay Set-Up:

| 2.5x Master Mix | 40 μL |
|---|---|

Contains:
2.5× Regeneration System: from 100× stock is 333 mM Glucose-6-phosphate, 30 Units/mL Glucose-6-phosphate dehydrogenase in 100 mM Potassium Phosphate Buffer, pH 7.4

| Test Sample (can contain enzyme) | 40 µL |
|---|---|

5× NADP+/AMPPD-Bn Mix
20 µL
Contains:
NADP+: 100× stock is 10 mM NADP+ in 100 mM Potassium Phosphate Buffer, pH 7.4
100 µM AMPPD-Bn Assay Procedure:
1. Thaw all reagents on ice, except substrates: warm-up to RT under aluminum foil (light sensitive)
2. Prepare 2.5× Master Mixes in 1× reaction buffer (keep on ice).
100× Regeneration System: 2.5× (final=1×)
CYP3A4 preferred Buffer: Bring to final volume.

| Isozyme | 2×Buffer | 1×Buffer |
|---|---|---|
| CYP3A4 | 200 mM Potassium Phosphate, pH 7.4 | 100 mM Potassium Phosphate, pH 7.4 |

3. Prepare 2.5× Master Mixes containing inhibitor in 1× reaction buffer (keep on ice).
100× Regeneration System: 2.5× (final=1×)
2.5× Miconazole or Ketoconazole (1-2 µM final)
CYP3A4 preferred Buffer: Bring to final volume.
4. Add 40 µl of the specific 2.5× Master Mix to the wells
5. Add 40 µl of the specific 2.5× Master Mix containing inhibitor to the wells
6. Prepare serial dilutions, as desired, of your test sample (microsomal fraction, supernatant, extract, and the like.) in 1× buffer. Make the dilutions to be 2.5× the final desired concentration (if known).
7. Prepare serial dilutions of rhCYP3A4 in buffer if using a standard curve.
8. Add 40 µL of the test sample(s) to the assay wells containing the master mix.
9. Add 40 µL of the rhCYP3A4 serial dilution samples to the assay wells if you are running a standard curve.
10. Cover plate with plate sealer and let the assay wells equilibrate to 25° C. or room temperature for a few minutes while you prepare the 5× NADP+/Substrate Mixture.
11. Prepare 5× NADP+/Substrate Mixture immediately before use (light sensitive!)
Test Substrate:

| Substrate | *Stock solution (in Acetonitrile) | 5× concentration | Final (1×) concentration |
|---|---|---|---|
| AMPPD-Bn | >3 mM | 100 µM | 20 µM |

100× NADP+: 10× (1× final)
H₂O: to final volume.
Add substrate by trituration and vortex to allow for maximum substrate solubility in the aqueous mixture.
*The final organic solvent concentration in the assay should be less than 0.1% and preferably much less.
12. Add 20 µL of 5× NADP+/AMPPD-Bn to each assay well.
13. Incubate at 25° C. for 30 minutes (enzyme turnover will have reached steady-state).

| Isozyme/Substrate Pair | Incubation Time |
|---|---|
| CYP3A4/AMPPD-Bn | 25 minutes |

14. Inject 100 µL of Accelerator II via injector on luminometer
15. Read for 2 second, with a 1 second delay
16. Compare samples with versus without inhibitor.
17. Compare relative RLUs between CYP isozyme wells to standard curve of rhCYP3A4 for quantification.

Example 53

Screening Molecules, Mixtures of Molecules, or Library of Molecules for Cytochrome P450 Inhibition or Activation.

In Drug Discovery, it is desirable to know if a molecule, compound, or drug lead inhibits or activates CYP450 enzymes of interest as such effects can lead to adverse patient side affects referred to as drug-drug interactions (DDIs). Some CYP450 enzymes are, themselves, potential drug targets for various indications, such that a researcher may want to screen for CYP450 enzyme inhibitors or activators in order to find drug leads for that indication. For these reasons, researchers can screen molecules, mixtures of molecules (such as plant extracts), or molecule libraries to determine if a molecule affects CYP450 activity.

Cytochrome P450 assays that have been developed for use in a chemiluminescent format utilize novel 1,2-dioxetane chemiluminescent substrates. Five major isozymes are described with their subsequent substrate. The following is an example of an inhibition assay performed with the new substrates and reagents. CYP450 (rh or HLMs), Regeneration System (final [1×]) and 100 mM Potassium Phosphate Buffer are prepped as a 2.5× Master Mix. 40 µL of the Master Mix is added to the wells of a 96-well plate. 40 µL of a 2.5× drug, drug-candidate, or other test compound(s) is added to the rows of the plate containing the Master Mix. The plate is incubated at 25° C. for 30 minutes. After the incubation, 20 µL of a 5× NADP+ (nicotinamide adenine dinucleotide phosphate) and 1,2-dioxetane substrate mix to all wells. Incubate for 10-15 minutes at 25 degrees Celsius. Inject (via luminometer) 100 uL of Accelerator II into selected wells. Read for 1 second, with a 2 second delay. Number of replicas and test compounds addressed is user-specified.

These assays can also be performed using non-rhCYP microsome enzyme sources such as human liver microsomes, bodily fluids, tissue (liver, stomach, and the like), tissue microsomal fractions, tissue extracts, cells (hepatocytes, stem cells, or other), cell extracts, tissue or cell supernatants, organism, or other test samples. Assays using crude samples, such as the enzyme sources mentioned above, will perform more optimally using dioxetane CYP450 substrates that are isozyme-specific under the assay conditions.

The enzyme activity (activation, inhibition or affector) assay can also be performed in 1-step (kinetic or endpoint) mode as described in Example 48 (Format B) when using an appropriate substrate, such as CDP-Star-Bn or EG-Ad-Cl-Ph-OEOM to detect CYP3A4.

Figure 13:
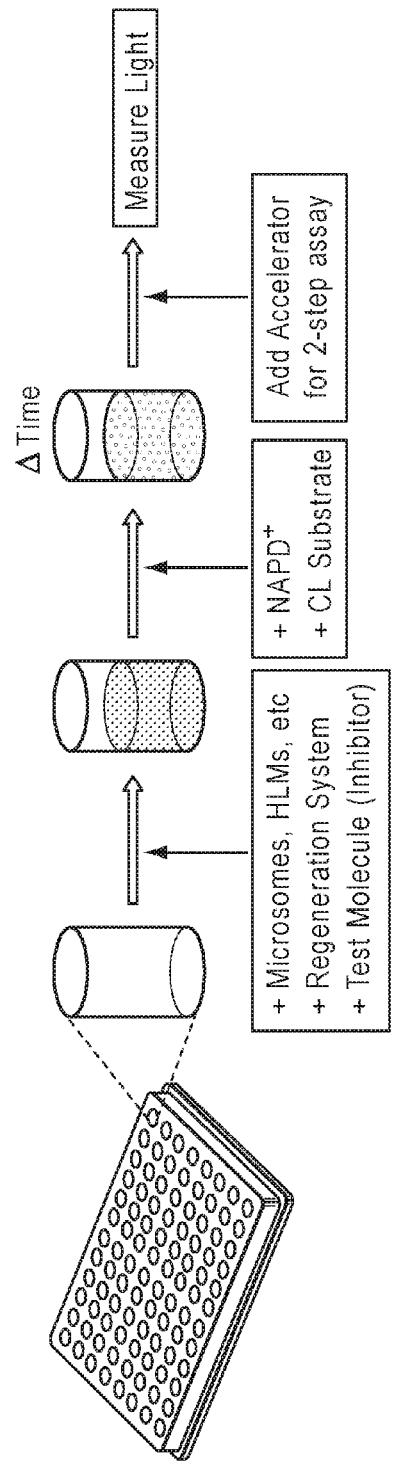
FIG. 13 shows a protocol overview of an assay for screening molecules for cytochrome P450 inhibition or activation (see, Example 53). Figure is adapted from Wienkers & Heath, Nature Reviews in Drug Discovery, 2005.

Protocol Overview: (See, FIG. 13).

| 2.5× Master Mix | 40 µL |
|---|---|

Contains:

Regeneration System: 100× stock is 333 mM Glucose-6-phosphate, 30 Units/mL Glucose-6-phosphate dehydrogenase in 100 mM Potassium Phosphate Buffer, pH 7.4

Desired Isozyme

| | |
|---|---|
| 2.5× Test Compound (contains dilution of Inhibitor) | 40 μL |
| 25° C. Incubation for 30 minutes | |
| 5×NADP+/Substrate Mix | 20 μL |

Contains:

NADP+: 100× stock is 10 mM NADP+ in 100 mM Potassium Phosphate Buffer, pH 7.4

Substrate specific to desired isozyme

25° C. Incubation for 10-15 minutes

Materials:

Cytochrome P450 Isozymes:
  CYP3A4 (BD/Gentest, Cat #456202) (or other vendor)
  CYP2C19 (BD/Gentest, Cat #456259) (or other vendor)
  CYP2C9 (BD/Gentest, Cat #456258) (or other vendor)
  CYP2D6 (BD/Gentest, Cat #456217) (or other vendor)
  CYP1A2 (BD/Gentest, Cat #456203) (or other vendor)

100 mM Potassium Phosphate Buffer, pH 7.4

50 mM Potassium Phosphate Buffer, pH 7.4

100× NADP+
  (10 mM NADP+ in 100 mM Potassium phosphate buffer, pH 7.4)

100× Regeneration System
  (333 mM Glucose-6-phosphate, 30 Units/mL Glucose-6-phosphate dehydrogenase in 100 mM Potassium Phosphate Buffer, pH 7.4)

Substrates (in 100% Acetonitrile)
  AMPPD-Bn (CYP3A4)
  BZT-Me (CYP2C9 and CYP2C19)
  Cl-BZT-EOM (CYP2D6)
  Cl-BZT-Me (CYP1A2)

96 well white microplate

Inhibitors for positive controls:
  Ketoconazole (CYP3A4)
  Miconazole (CYP2C19)
  Sulfaphenazole (CYP2C9)
  Quinidine (CYP2D6)
  Furafylline (CYP1A2)

Accelerator II

Assay Procedure:

1. Thaw all reagents on ice, except substrates: warm-up to RT under aluminum foil (light sensitive)
2. Prepare 2.5× Master Mix (keep on ice) (makes enough for 125 wells)

| Isozyme | 2.5× concentration | Final (1×) concentration |
|---|---|---|
| CYP3A4 | 12.5 nM | 5 nM |
| CYP2C19 | 12.5 nM | 5 nM |
| CYP2C9 | 25 nM | 10 nM |
| CYP2D6 | 25 nM | 10 nM |
| CYP1A2 | 12.5 nM | 5 nM |

100× Regeneration System: 2.5× (final=1×)
Buffer: q.s. to 5 mL

| Isozyme | Buffer |
|---|---|
| CYP3A4 | 100 mM Potassium Phosphate, pH 7.4 |
| CYP2C19 | 50 mM Potassium Phosphate, pH 7.4 |
| CYP2C9 | 50 mM Potassium Phosphate, pH 7.4 |
| CYP2D6 | 100 mM Potassium Phosphate, pH 7.4 |
| CYP1A2 | 100 mM Potassium Phosphate, pH 7.4 |

3. Add 40 μL of 2.5× Master Mix to each well of the plate
4. Prepare 2.5× positive controls and test compound(s) in buffer:
5. Add 40 μL of 2.5× inhibitors (positive controls) to the appropriate wells of the plate.
6. Add 40 μL of water (negative controls) to the appropriate wells of the plate
7. Add 40 μL of 2.5× test compound(s) to the appropriate wells of the plate
8. Cover plate with plate sealer and incubate at 25° C. for 30 minutes
9. Prepare 5× NADP+/Substrate Mixture immediately before use (light sensitive!)
Substrate:

| Isozyme | Substrate | 5× concentration | Final (1×) concentration |
|---|---|---|---|
| CYP3A4 | AMPPD-Bn | 10 uM | 2 uM |
| CYP2C19 | BZT-Me | 5 uM | 1 uM |
| CYP2C9 | BZT-Me | 10 uM | 2 uM |
| CYP2D6 | Cl-BZT-EOM | 25 uM | 5 uM |
| CYP1A2 | Cl-BZT-Me | 6.25 uM | 1.25 uM |

100× NADP+: 5× (1× final)
Buffer: q.s. to final volume
10. Add 20 μL of 5× NADP+/Substrate to each well.
11. Incubate at 25° C. for:

| Isozyme/Substrate Pair | Incubation Time |
|---|---|
| CYP3A4/AMPPD-Bn | 10 minutes |
| CYP2C19/BZT-Me | 10 minutes |
| CYP2C9/BZT-Me | 12 minutes |
| CYP2D6/Cl-BZT-EOM | 15 minutes |
| CYP1A2/Cl-BZT-Me | 15 minutes |

12. Inject 100 μL of Accelerator II via injector on luminometer
13. Read for 2 second, with a 1 second delay
14. Analyze data according to percent enzyme activity based on negative control (100% activity) values.

Example 54

Screening Molecules, Mixtures of Molecules, or Library of Molecules for Cytochrome P450 Induction or Reduction In drug discovery, it is desirable to know if a molecule, compound, or drug lead leads to increased or decreased CYP450 enzyme levels. Such effects can lead to adverse patient side affects referred to as drug-drug interactions (DDIs) to due increased or decreased drug clearance. For this reason, researchers can screen molecules, mixtures of molecules (such as plant extracts), or molecule libraries to determine if a molecule affects CYP450 enzyme levels.

Assays can be performed as in Example 52. These assays can also be performed using non-rhCYP microsome enzyme sources such as human liver microsomes, bodily fluids, tissue (liver, stomach, and the like), tissue microsomal fractions, tissue extracts, cells (hepatocytes, stem cells, or other), cell extracts, tissue or cell supernatants, or organism. Assays using crude samples, such as the enzyme sources mentioned above, will perform more optimally using dioxetane CYP450 substrates that are isozyme-specific under the assay conditions.

The enzyme induction (or reduction) assay can also be performed in 1-step (kinetic or endpoint) mode as described in Example 48 (Format B) when using an appropriate substrate, such as CDP-Star-Bn or EG-Ad-Cl-Ph-OEOM to detect CYP3A4.

Figure 14:
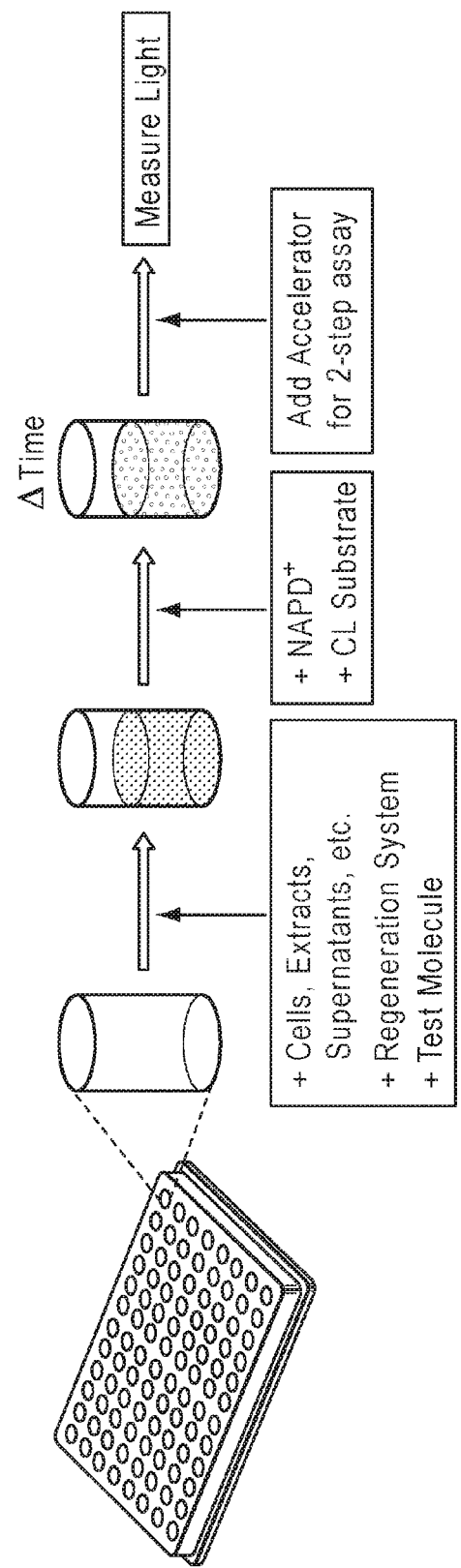
FIG. 14 shows a protocol overview of an enzyme induction (or reduction) assay (see, Example 54). Figure is adapted from Wienkers & Heath, Nature Reviews in Drug Discovery, 2005.

Protocol Overview: (See, FIG. 14).

While the present teachings are described in conjunction with various embodiments, it is not intended that the present teachings be limited to such embodiments. On the contrary, the present teachings encompass various alternatives, modifications, and equivalents, as will be appreciated by those of skill in the art.

We claim:

1. An assay for the detection of the presence of an oxidative enzyme in an aqueous sample, comprising:
   1) adding to the aqueous sample a dioxetane of formula (I) to form a mixture,

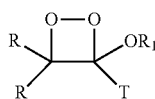
(I)

where both R groups together form a spiroadamantyl group bound to the dioxetane ring, which can be unsubstituted or substituted at either head carbon or both with an electron-withdrawing group or electron donating group, and
wherein $R_1$ is an aryl group, or an alkyl group of 1-20 carbon atoms, which can be optionally substituted with 1 or more halogen atoms, and
wherein T is an aryl or heteroaryl ring selected from formula (a) or (b) capable of emitting light upon oxidative enzyme activated decomposition of the dioxetane (I):

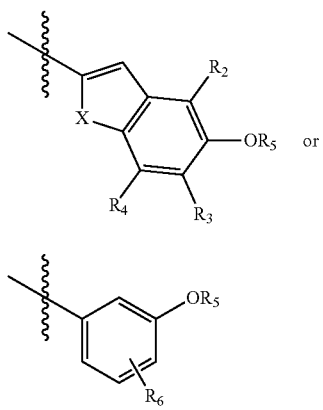

wherein $R_2$, $R_3$, $R_4$, and $R_6$ can be independently H, or an electroactive group, which can be electron-withdrawing or electron-donating, and wherein $R_5$ is a group that can be removed upon activation by an oxidative enzyme comprising an alkyl group of 1-20 carbon atoms, an arylmethylene group (—$CH_2Ar$), or a benzyl (—$CH_2Phe$);
and wherein X is selected from the group consisting of S, N, and O
with the proviso that the dioxetane is not

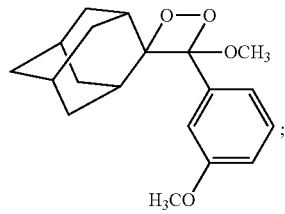 [SMILES: COc1cccc(C2(OC)OOC23C2CC4CC(C2)CC3C4)c1]

2) adding an oxygen source to the mixture; and
3) detecting a change in chemiluminescent signal emitted from the mixture which is indicative of the presence of the oxidative enzyme in the sample.

2. The assay of claim 1, wherein the assay is selected from:
   an assay for the detection of the change in oxidative enzyme activity in an enzyme inhibition or enzyme activation assay;
   an assay for the detection of the presence of an oxidative enzyme in an enzyme induction or enzyme detection assay;
   an assay for the detection of the presence of a CYP450 enzyme including a CYP450 isozyme;
   an assay for detecting the change in CYP450 enzyme activity in an enzyme inhibition or enzyme activation assay; and
   an assay for the detection of the presence of a CYP450 enzyme in an enzyme induction or enzyme detection assay.

3. The assay of claim 1, wherein $R_2$, $R_3$, $R_4$, and $R_6$ are selected from the group consisting of halo (F, Cl, Br, I), trialkylammonium (—$NR_3^+$), trialkylphosphonium (—$PR_3^+$), alkylamido (—NHCOR, (—NRCOR), arylamido (—NHCOAr, NRCOAr, NArCOAr), arylcarbamoyl (—NHCOOAr, —NRCOOAr), alkylcarbamoyl (—NHCOOR, NRCOOR), cyano (—CN), nitro (—$NO_2$), ester (—COOR, COOAr), alkyl- or arylsulfonamido (—$NHSO_2R$, —$NHSO_2Ar$), trifluoromethyl (—$CF_3$), alkyl (—R), aryl (—Ar), trialkyl-, triaryl- or alkylarylsilyl (—$SiR_3$, —$SiAr_3$, —$SiArR_2$), alkyl- or arylamidosulfonyl (—$SO_2NHCOR$, —$SO_2NHCOAr$), alkyl- or arylsulfonyl (—$SO_2R$, —$SO_2Ar$), alkyl- or arylthioethers (—SR, —SAr), alkoxy (—OR), or aryloxy (—OAr) substituents.

4. The assay of claim 1, wherein $R_2$ comprises chloro.

5. The assay of claim 1, wherein $R_6$ comprises chloro.

6. The assay of claim 1, the dioxetane comprising one of the structures below selected from:

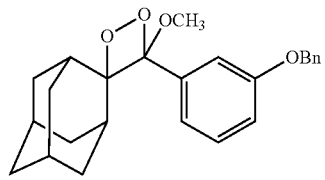

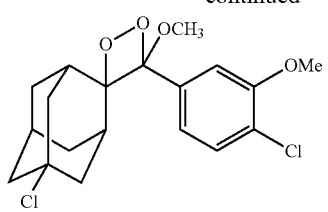
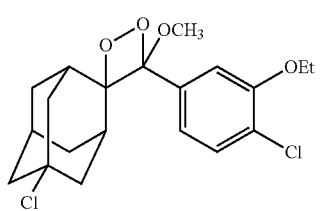
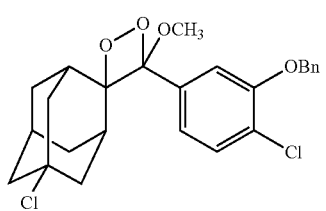
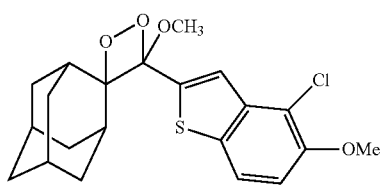
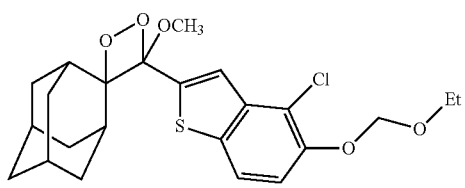
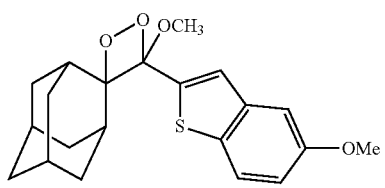
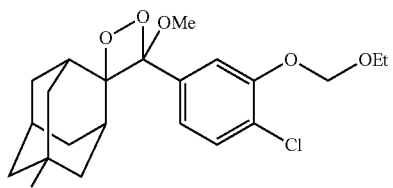
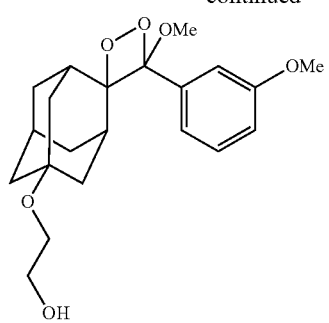
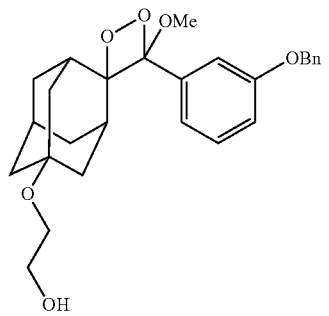
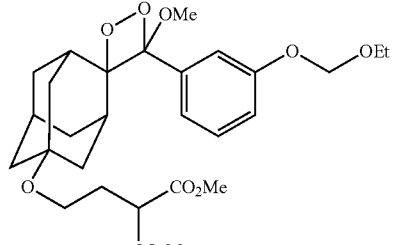
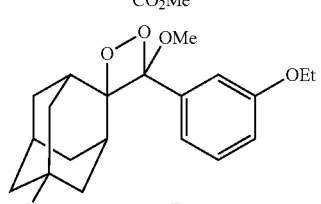
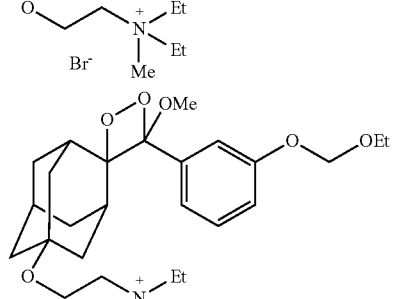
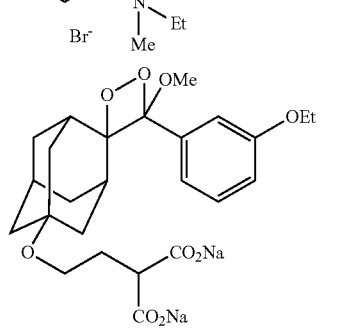

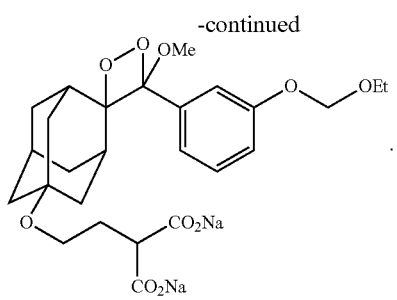

7. The assay of any one of claims 1-6 comprising one of the following:
- (i) the dioxetane of claim 1 (1: AMPPD-Bn), and cytochrome 3A;
- (ii) the dioxetane of claim 1 (1: AMPPD-Bn), and cytochrome 2C19;
- (iii) the dioxetane of claim 1 (2: CDP-Star-Me), and cytochrome 2C19;
- (iv) the dioxetane of claim 1 (3: CDP-Star-Et), and cytochrome 2C19;
- (v) the dioxetane of claim 1 (4: CDP-Star-Bn), and cytochrome 3A;
- (vi) the dioxetane of claim 1 (5: Cl-BZT-Me), and cytochrome 2C19;
- (vii) the dioxetane of claim 1 (5: Cl-BZT-Me), and cytochrome 1A2;
- (viii) the dioxetane of claim 1 (6: Cl-BZT-EOM), and cytochrome 2C19;
- (ix) the dioxetane of claim 1 (6: Cl-BZT-EOM), and cytochrome 3A5;
- (x) the dioxetane of claim 1 (6: Cl-BZT-EOM), and cytochrome 2D6;
- (xi) the dioxetane of claim 1 (7: BZT-Me), and cytochrome 2C19;
- (xii) the dioxetane of claim 1 (7: BZT-Me), and cytochrome 2C9;
- (xiii) the dioxetane of claim 1 (8: EG-Ad-Cl-Ph-OEOM), and cytochrome 3A;
- (xiv) the dioxetane of claim 1 (9: EG-Ad-Ph-OMe), and cytochrome 2C19;
- (xv) the dioxetane of claim 1 (10: EG-Ad-Ph-OBn), and cytochrome 3A;
- (xvi) the dioxetane of claim 1 (11: bisCO2Me-Ad-Ph-OEOM), and cytochrome 3A;
- (xvii) the dioxetane of claim 1 (12: Q+-Ad-Ph-OEt), and cytochrome 3A;
- (xviii) the dioxetane of claim 1 (13: Q+-Ad-Ph-OEOM), and cytochrome 3A;
- (xix) the dioxetane of claim 1 (14: bisCO2Na-Ad-Ph-OEt), and cytochrome 2C8; or
- (xx) the dioxetane of claim 1 (15: bisCO2Na-Ad-Ph-OEOM), and cytochrome 2C8.

8. The assay of claim 1, conducted using a solid matrix.

9. The assay of claim 1, carried out in the further presence of a water-soluble enhancing substance that increases specific light energy production above that produced in its absence.

10. The assay of claim 9, wherein said water-soluble enhancing substance is serum albumin.

11. The assay of claim 9, wherein said water-soluble enhancing substance comprises fatty acid free serum albumin.

12. The assay of claim 9, wherein said water-soluble enhancing substance comprises a polymeric quaternary onium salt.

13. The assay of claim 9, wherein said water-soluble enhancing substance comprises a phosphonium, sulfonium or ammonium polymeric quaternary salt.

14. The assay of claim 13, wherein said the polymeric quaternary onium salt comprises poly(vinylbenzyltrimethylammonium chloride) (TMQ), poly(vinylbenzyltributylammonium chloride) (TBQ), poly(vinylbenzyltributylphosphonium chloride), poly(vinylbenzyltrioctyl phosphonium chloride), or poly(vinylbenzyldimethylbenzylammonium chloride) (BDMQ).

15. The assay of claim 9, wherein said enhancing substance comprises a positively charged polymeric quaternary onium salt and a dye capable of forming a ternary complex with the negatively charged product of said 1,2-dioxetane compound (I) produced following enzyme-catalyzed decomposition of said 1,2-dioxetane compound, whereby energy transfer occurs between said negatively charged product and dye, and light energy is emitted by the dye.

16. The assay of claim 15, wherein the dye comprises fluorescein.

17. The assay of claim 15, wherein the dye comprises sulforhodamine.

18. The assay of claim 1, wherein the aqueous sample is a recombinant human or other CYP450 microsomes, bodily fluids, tissue sample, liver sample, stomach sample, tissue microsomal fractions, tissue extracts, crude samples, human liver microsomes, cells, hepatocytes, stem cells, cell extracts, tissue or cell supernatants, or organisms.

19. The assay of claim 1, further comprising adding a drug, an other compound, or a stimulus to the assay and determining CYP450 isozyme induction in response to the drug, the other compound, or the stimulus.

20. The assay of claim 1, wherein the oxygen source is a nicotinamide adenine dinucleotide phosphate (NADP+) regenerating system.

21. The assay of claim 1, wherein the oxidative enzyme is a CYP450 enzyme and wherein the identification further comprises identifying the CYP450 isozyme composition.

22. The assay of claim 21, wherein the CYP450 enzyme is from a microorganism, a plants, an animal, a mammal or a human.

23. The assay of claim 21, wherein the CYP450 isozyme is CYP1A2, CYP2C9, CYP2C19, CYP2D6, or CYP3A4.

* * * * *

UNITED STATES PATENT AND TRADEMARK OFFICE
CERTIFICATE OF CORRECTION

PATENT NO. : 9,856,508 B2
APPLICATION NO. : 15/345098
DATED : January 2, 2018
INVENTOR(S) : Juo et al.

Page 1 of 1

It is certified that error appears in the above-identified patent and that said Letters Patent is hereby corrected as shown below:

On the Title Page

The Related U.S. Application Data should read:
Division of application No. 14/694,758, filed on Apr. 23, 2015, now Patent No. 9,518,285, which is a continuation of application No. 13/254,154, filed as application No. PCT/US2010/025791 on Mar. 1, 2010, now Patent No. 9,067,910, which claims priority to U.S. Provisional application No. 61/156,836, filed on Mar. 2, 2009.

Signed and Sealed this
Third Day of July, 2018

Andrei Iancu
*Director of the United States Patent and Trademark Office*